(12) United States Patent
Tohnishi et al.

(10) Patent No.: US 6,603,044 B1
(45) Date of Patent: Aug. 5, 2003

(54) PHTHALAMIDE DERIVATIVES, OR SALT THEREOF AGROHORTICULTURAL INSECTICIDE, AND METHOD FOR USING THE SAME

(75) Inventors: Masanori Tohnishi, Sakai (JP); Hayami Nakao, Kawachinagano (JP); Eiji Kohno, Habikino (JP); Tateki Nishida, Tondabayashi (JP); Takashi Furuya, Izumisano (JP); Toshiaki Shimizu, Kawachinagano (JP); Akira Seo, Hashimoto (JP); Kazuyuki Sakata, Kawachinagano (JP); Shinsuke Fujioka, Kawachinagano (JP); Hideo Kanno, Ibaraki (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 09/449,420

(22) Filed: Nov. 29, 1999

(30) Foreign Application Priority Data

Nov. 30, 1998 (JP) .......................................... 10-340379
Aug. 20, 1999 (JP) .......................................... 11-234329

(51) Int. Cl.$^7$ ..................... C07C 233/64; C07C 233/65; C07C 233/76
(52) U.S. Cl. .................. 564/154; 546/291; 546/292; 548/171; 548/187; 549/366; 549/441; 558/50; 560/13; 514/346; 514/367; 514/369; 514/452; 514/465; 514/562; 514/618
(58) Field of Search .......................... 564/154; 514/346, 514/367, 369, 452, 465, 562, 618; 546/291, 292; 548/171, 187; 549/366, 441; 558/50; 560/13

(56) References Cited

U.S. PATENT DOCUMENTS 4,732,845 A    3/1988  Keiji et al.

FOREIGN PATENT DOCUMENTS

| DE | 119428 | 9/1984 |
|---|---|---|
| DE | 3802175 | 8/1989 |
| EP | 0 325983 | 8/1989 |
| EP | 0365149 A2 | 4/1990 |
| EP | 0394126 A1 | 10/1990 |
| EP | 0410726 A1 | 1/1991 |
| JP | 59 163353 | 9/1984 |
| JP | 61 180753 | 8/1986 |

OTHER PUBLICATIONS

Yokoyama: "Silver Halide Color Photographic Senstive Material" Patent Abstracts of Japan, No. 03198049 (JP–A–3–198049), 1991.

Chemical Abstracts: vol. 124, No. 6, No. 56894r, XP002095523, 1996.

Chemical Abstract: vol. 91, No. 9, No. 74313e, XP002095528, 1979.

Chemical Abstract: vol. 68, No. 3, No. 12654h, XP002095529, 1968.

Chemical Abstract: vol. 70, No. 15, No. 68102k, XP002095530, 1969.

Boyd, et al: Synthesisi and Reactions of Cyclic Isoimidium Salts, J.C.S. Perkin I, pp. 1338–1350, 1978.

Chemical Abstracts: vol. 123, No. 26, No. 343359e, XP002095524, 1995.

Chemical Abstract: vol. 120, No. 21, NO. 269853f, XP002095525, 1994.

Chemical Abstracts: vol. 113, No. 19, No. 171822a, XP002095526, 1990.

Chemical Abstract: vol. 109, No. 5, No. 37397c, XP002095527, 1988.

Nippon Kayaku Patent Abstr–Japan V.011, No.003 C395 Japan Aug. 13, 1986.

Primary Examiner—Brian Davis
(74) Attorney, Agent, or Firm—Paul E. White, Jr.; Manelli Denison & Selter PLLC

(57) ABSTRACT

The present invention provides a phthalamide derivative of the formula (I):

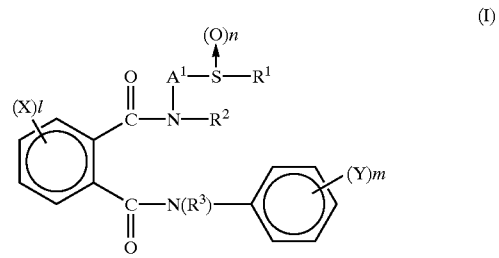

wherein $A^1$ is (substituted) $C_1$–$C_8$ alkylene, (substituted) $C_3$–$C_8$ alkenylene, (substituted) $C_3$–$C_8$ alkynylene, etc., $R^1$ is H, (halo) $C_3$–$C_6$ cycloalkyl, (substituted) phenyl, (substituted) heterocycle, —$A^2$—$R^4$, etc., $R^2$ and $R^3$ are H, $C_3$–$C_6$ cycloalkyl, —$A^2$—$R^4$, etc., $A^2$ is —C(=O)—, —C(=S)— or —C(=NR$^5$)—, $R^4$ is H, alkyl, (substituted) phenyl, (substituted) heterocycle, etc., X and Y are halogen, cyano, nitro, (halo) $C_1$–$C_6$ alkyl, (halo) $C_1$–$C_6$ alkoxy, etc., l is 0–4, m is 0–5, n is 0–2; and an agrohorticultural insecticide containing said compound as active ingredient and exhibiting an excellent insecticidal effect.

9 Claims, No Drawings

PHTHALAMIDE DERIVATIVES, OR SALT THEREOF AGROHORTICULTURAL INSECTICIDE, AND METHOD FOR USING THE SAME

BACKGROUND OF THE INVENTION

1. Field of the Invention

The present invention relates to a phthalamide derivative or salt thereof, an agrohorticultural insecticide containing said compound as an active ingredient thereof, and a method for using the agrohorticultural agent.

2. Related Art

JP-A-61-180753 discloses some of the phthalamide derivatives of the present invention. However, in that patent application specification, there is neither disclosed nor suggested about usefulness of said derivatives as an agrohorticultural insecticide. Further, although similar compounds are disclosed in JP-A-59-163353 and J. C. S. Perkin I, 1338–1350 (1978), etc., there is made no mention nor suggestion in these publications about usefulness of those compounds as an agrohorticultural insecticide.

SUMMARY OF THE INVENTION

The present inventors have conducted extensive studies with the aim of developing a novel agrohorticultural agent. As a result, it has been found that the phthalamide derivatives of the present invention represented by general formula (I), which are novel compounds not found in literature, can be put to a novel use as an agrohorticultural insecticide comprising not only these novel compounds but also some known compounds disclosed in prior art. Based on this finding, the present invention has been accomplished.

DETAILED DESCRIPTION OF THE INVENTION

The present invention relates to phthalamide derivatives represented by the following general formula (I) or salt thereof, an agrohorticultural insecticide containing, as active ingredients thereof, the phthalamide derivative represented by the general formula (I) or salt thereof and some known compounds, and a method for using the same:

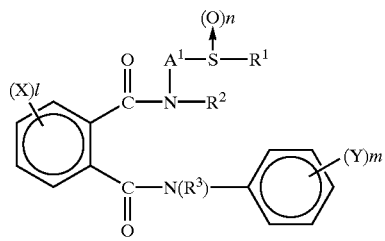

(I)

wherein $A^1$ represents $C_1$–$C_8$ alkylene group, substituted $C_1$–$C_8$ alkylene group having at least one, same or different substituents selected from the group consisting of halogen atom, cyano group, nitro group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, hydroxy $C_1$–$C_6$ alkyl group, $C_1$–$C_6$ alkoxy $C_1$–$C_6$ alkyl group, $C_1$–$C_6$ alkylthio $C_1$–$C_6$ alkyl group, $C_1$–$C_6$ alkoxycarbonyl group, phenyl group and substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, $C_3$–$C_8$ alkenylene group, substituted $C_3$–$C_8$ alkenylene group having at least one, same or different substituents selected from the group consisting of halogen atom, cyano group, nitro group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, $C_1$–$C_6$ alkylthio $C_1$–$C_6$ alkyl group, $C_1$–$C_6$ alkoxycarbonyl group, phenyl group and substituted phenyl group having at least one, same or different substituents selected from the group consisting of halogen atom, cyano group, nitro group, $C_1$–$C_6$ alkyl group, halo $C_1$–$C_6$ alkyl group, halo $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, $C_3$–$C_8$ alkynylene group, or substituted $C_3$–$C_8$ alkynylene group having at least one, same or different substituents selected from the group consisting of halogen atom, cyano group, nitro group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, $C_1$–$C_6$ alkylthio $C_1$–$C_6$ alkyl group, $C_1$–$C_6$ alkoxycarbonyl group, phenyl group and substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, further, an arbitrary saturated carbon atom in said $C_1$–$C_8$ alkylene group, substituted $C_1$–$C_8$ alkylene group, $C_3$–$C_8$ alkenylene group, substituted $C_3$–$C_8$ alkenylene group, $C_3$–$C_8$ alkynylene group and substituted $C_3$–$C_8$ alkynylene group may be substituted with a $C_2$–$C_5$ alkylene group to form a $C_3$–$C_6$ cycloalkane ring, and arbitrary two carbon atoms in said $C_1$–$C_8$ alkylene group, substituted $C_1$–$C_8$ alkylene group, $C_3$–$C_8$ alkenylene group and substituted $C_3$–$C_8$ alkenylene group may be taken conjointly with an alkylene group or an alkenylene group to form a $C_3$–$C_6$ cycloalkane ring or $C_3$–$C_6$ cycloalkene ring;

$R^1$ represents hydrogen atom, mercapto group, $C_1$–$C_6$ alkylthio group, halo $C_1$–$C_6$ alkylthio group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^2$—$R^4$ [wherein $A^2$ represents —C(=O)—, —C(=S)—, or —C(=$NR^5$)— (in which $R^5$ represents hydrogen atom, $C_1$–$C_6$ alkyl group, $C_1$–$C_6$ alkoxy group, mono $C_1$–$C_6$ alkylamino group, di $C_1$–$C_6$ alkylamino group in which $C_1$–$C_6$ alkyl groups may be same or different, $C_1$–$C_6$ alkoxycarbonyl group, phenyl group or substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group),
$C_1$–$C_8$ alkylene group, halo $C_1$–$C_8$ alkylene group, $C_3$–$C_6$ alkenylene group, halo $C_3$–$C_6$ alkenylene group, $C_3$–$C_6$ alkynylene group or halo $C_3$–$C_6$ alkynylene group; and
(1) in cases where $A^2$ represents —C(=O)—, —C(=S)— or —C(=$NR^5$)— wherein $R^5$ is as defined above, $R^4$ represents hydrogen atom, $C_1$–$C_6$ alkyl group, halo $C_1$–$C_6$ alkyl group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$Z^1$—$R^6$ wherein $Z^1$ represents —O—, —S— or —N($R^7$)— (wherein $R^7$ represents hydrogen atom, $C_1$–$C_6$ alkyl group, $C_1$–$C_6$ alkylcarbonyl group, halo $C_1$–$C_6$ alkylcarbonyl group or $C_1$–$C_6$ alkoxycarbonyl group), and $R^6$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenyl $C_1$–$C_4$ alkyl group, substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, and
(2) in cases where $A^2$ represents $C_1$–$C_8$ alkylene group, halo $C_1$–$C_8$ alkylene group, $C_3$–$C_6$ alkenylene group, halo $C_3$–$C_6$ alkenylene group, $C_3$–$C_6$ alkynylene group or halo $C_3$–$C_6$ alkynylene group, $R^4$ represents hydrogen atom, halogen atom, cyano group, nitro group, $C_3$–$C_6$ cycloalkyl group, halo $C_3$–$C_6$ cycloalkyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$Z^2$—$R^8$ wherein $Z^2$ represents —O—, —S—, —SO—, —$SO_2$—, —$N(R^9)$— (wherein $R^9$ represents hydrogen atom, $C_1$–$C_6$ alkyl group, $C_1$–$C_6$ alkylcarbonyl group, halo $C_1$–$C_6$ alkylcarbonyl group, $C_1$–$C_6$ alkoxycarbonyl group, phenylcarbonyl group, or substituted phenylcarbonyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group), —C(=O)— or —C(=$NOR^{10}$)— (wherein $R^{10}$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_1$–$C_6$ alkynyl group, $C_3$–$C_6$ cycloalkyl group, phenyl $C_1$–$C_4$ alkyl group or substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group) and $R^8$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, $C_1$–$C_6$ alkylcarbonyl group, halo $C_1$–$C_6$ alkylcarbonyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenyl $C_1$–$C_4$ alkyl group, substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group], or alternatively, $R^1$ may be combined with $A^1$ to form a 5- to 8-membered ring which may be intercepted by 1 or 2, same or different oxygen atoms, sulfur atoms or nitrogen atoms;

$R^2$ and $R^3$ which may be same or different, represent hydrogen atom, $C_3$–$C_6$ cycloalkyl group or —$A^2$—$R^4$ wherein $A^2$ and $R^4$ are as defined above; or alternatively, $R^2$ may be combined with $A^1$ or $R^1$ to form a 5- to 7-membered ring which may be intercepted by 1 or 2, same or different oxygen atoms, sulfur atoms or nitrogen atoms;

X which may be same or different, represents halogen atom, cyano group, nitro group, $C_3$–$C_6$ cycloalkyl group, halo $C_3$–$C_6$ cycloalkyl group, $C_1$–$C_6$ alkoxycarbonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^3$—$R^{11}$ [wherein $A^3$ represents —O—, —S—, —SO—, —$SO_2$—, —C(=O)—, —C(=$NOR^{12}$)— (in which $R^{12}$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, $C_3$–$C_6$ cycloalkyl group, phenyl $C_1$–$C_4$ alkyl group or substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group), $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group; and (1) in cases where $A^3$ represents —O—, —S—, —SO— or —SO$_2$—, $R^{11}$ represents halo $C_3$–$C_6$ cycloalkyl group, halo $C_3$–$C_6$ cycloalkenyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^4$—$R^{13}$ (wherein $A^4$ represents $C_1$–$C_6$ alkylene group, halo $C_1$–$C_6$ alkylene group, $C_3$–$C_6$ alkenylene group, halo $C_3$–$C_6$ alkenylene group, $C_3$–$C_6$ alkynylene group or halo $C_3$–$C_6$ alkynylene group, and $R^{13}$ represents hydrogen atom, halogen atom, $C_3$–$C_6$ cycloalkyl group, halo $C_3$–$C_6$ cycloalkyl group, $C_1$–$C_6$ alkoxycarbonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^5$—$R^{14}$ (wherein $A^5$ represents —O—, —S—, —SO—, —SO$_2$ or —C(=O)—, and $R^{14}$ represents $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group)), and (2) in cases where $A^3$ represents —C(=O)— or —C(=NOR$^{12}$)— wherein $R^{12}$ is as defined above, $R^{11}$ represents hydrogen atom, $C_1$–$C_6$ alkyl group, halo $C_1$–$C_6$ alkyl group, $C_2$–$C_6$ alkenyl group, halo $C_2$–$C_6$ alkenyl group, $C_3$–$C_6$ cycloalkyl group, halo $C_3$–$C_6$ cycloalkyl group, $C_1$–$C_6$ alkoxy group, $C_1$–$C_6$ alkylthio group, mono $C_1$–$C_6$ alkylamino group, di $C_1$–$C_6$ alkylamino group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylamino group, substituted phenylamino group having on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, and (3) in cases where $A^3$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group, $R^{11}$ represents hydrogen atom, hydroxy group, halogen atom, $C_3$–$C_6$ cycloalkyl group, halo $C_3$–$C_6$ cycloalkyl group, $C_1$–$C_6$ alkoxycarbonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^6$—$R^{15}$ (wherein $A^6$ represents —O—, —S—, —SO— or —$SO_2$—, and $R^{15}$ represents $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^7$—$R^{16}$ (wherein $A^7$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group, and $R^{16}$ represents hydrogen atom, halogen atom, $C_3$–$C_6$ cycloalkyl group, halo $C_3$–$C_6$ cycloalkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, cl–$C_6$ alkylsulfonyl group, halo $C_1$–$C_6$ alkylsulfonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenoxy group, substituted phenoxy group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group))]; and l represents an integer of 0 to 4; and alternatively, X may be taken conjointly with the adjacent carbon atom on the phenyl ring to form a fused ring, and said fused ring may have at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group; and Y may be same or different and represents halogen atom, cyano group, nitro group, halo $C_3$–$C_6$ cycloalkyl group, tri $C_1$–$C_6$ alkylsilyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^3$—$R^{11}$ wherein $A^3$ and $R^{11}$ are as defined above; and m represents an integer of 0 to 5; and Y may be taken conjointly with an adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, and substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group; and n represents an integer of 0 to 2;

provided that when X, $R^2$ and $R^3$ simultaneously represent hydrogen atom, m represents an integer of 2, Y of the 2-position represents fluorine atom and Y of the 3-position represents chlorine atom, then $A^1$ is not propylene group, $R^1$ is not methyl group and n is not an integer of 0.

In the definition of the general formula (I) representing the phthalamide derivative of the present invention, the term "halogen atom" means chlorine atom, bromine atom, iodine atom or fluorine atom; the term "$C_1$–$C_6$ alkyl", means a straight or branched chain alkyl group having 1 to 6 carbon atoms such as methyl, ethyl, n-propyl, i-propyl, n-butyl, i-butyl, s-butyl, t-butyl, n-pentyl, n-hexyl and the like; the term "halo $C_1$–$C_6$ alkyl" means a straight or branched chain alkyl group having 1 to 6 carbon atoms which may be substituted with at least one, same or different halogen atoms; the term "$C_1$–C8 alkylene" means a straight or branched chain alkylene group having 1 to 8 carbon atoms such as methylene, ethylene, propylene, trimethylene, dimethylmethylene, tetramethylene, isobutylene, dimethylethylene, octamethylene and the like; the term "a 5- to 8- or 5- to 7-membered ring which may be intercepted by 1 to 2, same or different oxygen atoms, sulfur atoms or nitrogen atoms formed by $R^1$ with $A^1$, or $R^2$ with $A^1$ or $R^{1}$" means, for example, perhydrothiazine ring, thiazolidine ring, thiazetidine ring, dihydrothiazine ring, thiazoline ring, perhydroxathiazine ring, dihydroxathiazine ring, dithiazine ring, perhydrodithiazine ring, and the like.

The term "heterocyclic group" means 5- to 6-membered heterocyclic group having one or more same or different hetero atoms selected from oxygen atoms, sulfur atoms or nitrogen atoms such as pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, trithiazolyl group, pyrazolyl group, and the like. As the "fused ring", there can be exemplified naphthalene, tetrahydronaphthalene, indene, indane, quinoline, quinazoline, indole, indoline, coumarone, isocoumarone, benzodioxane, benzodioxole, benzofuran, dihydrobenzofuran, benzothiophene, dihydrobenzothiophene, benzoxazole, benzothiazole, benzimidazole, indazole, and the like.

As a salt of a phthalamide derivative represented by the general formula (I) of the present invention, there can be exemplified inorganic acid salt such as hydrochlorate, sulfate, nitrate, phosphate and the like; organic acid salt such as acetate, fumarate, maleate, oxalate, methanesulfonate, benzenesulfonate, p-toluenesulfonate and the like; and salt of metallic ion such as sodium ion, potassium ion, calcium ion and the like.

Some of the phthalamide derivatives represented by the general formula (I) of the present invention contain an asymmetric carbon atom or an asymmetric center in the structural formula thereof, and in some cases there can exist two optical isomers. The present invention includes all these optical isomers and all the mixtures consisting of arbitrary proportions of these optical isomers.

Preferable examples of each substituent of the phthalamide derivative of general formula (I) or salt thereof of the present invention are $A^1$ is a straight or branched $C_1$–$C_8$ alkylene group; $R^1$ is $C_1$–$C_6$ alkyl group or halo $C_1$–$C_6$ alkyl group; each of $R^2$ and $R^3$ is hydrogen atom or $C_1$–$C_6$ alkyl group; X is halogen atom, nitro group, $C_1$–$C_6$ alkyl group, halo $C_1$–$C_6$ alkyl group or halo $C_1$–$C_6$ alkoxy group; and Y is halogen atom, $C_1$–$C_6$ alkyl group, halo $C_1$–$C_6$ alkyl group or halo $C_1$–$C_6$ alkoxy group.

The phthalamide derivatives of the present invention represented by the general formula (I) can be produced, for example, by the production processes mentioned below.

Production process 1

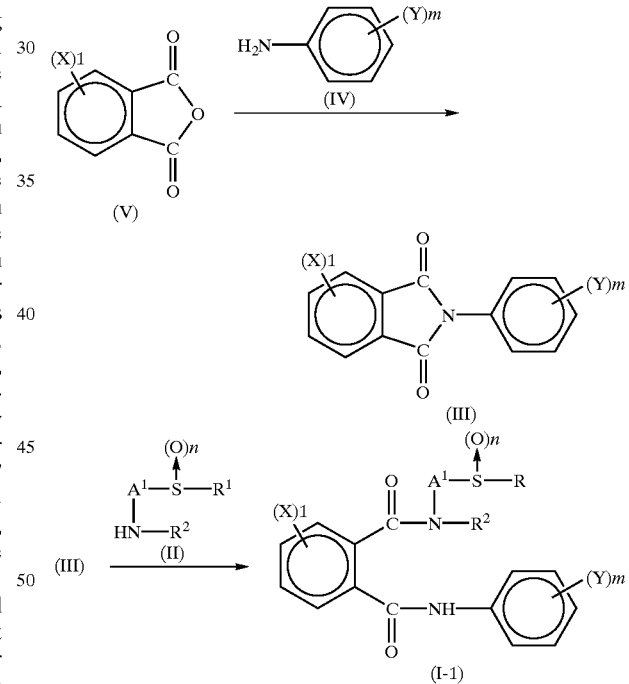

wherein $R^1$, $R^2$, $A^1$, X, Y, l, m and n are as defined above.

A phthalic anhydride derivative of the general formula (V) is reacted with an aniline of the general formula (IV) in the presence of an inert solvent to obtain a phthalimide derivative of the general formula (III). The phthalimide derivative (III) is reacted with an amine of the general formula (II) after or without being isolated, whereby a phthalamide derivative of the general formula (I-1) can be produced.

(1) General Formula (V)→General Formula (III)

As the inert solvent used in this reaction, any solvent may be used so long as it does not markedly inhibit the progress of the reaction. There can be exemplified aromatic hydrocarbons such as benzene, toluene, xylene, etc.; halogenated hydrocarbons such as dichloromethane, chloroform, carbon tetrachloride, etc., chlorinated aromatic hydrocarbons such as chlorobenzene, dichlorobenzene, etc.; acyclic or cyclic ethers such as diethyl ether, dioxane, tetrahydrofuran, etc., esters such as ethyl acetate, etc.; amides such as dimethylformamide, dimethylacetamide, etc.; acids such as acetic acid, etc.; dimethyl sulfoxide; and 1,3-dimethyl-2-imidazolidinone. These inert solvents may be used alone or as a mixture thereof.

Since the reaction is an equimolar reaction, it is sufficient that the reactants are used in equimolar amounts, though either of them may be used in excess. If necessary, the reaction may be carried out under dehydrating conditions.

As to the reaction temperature, the reaction can be carried out in a temperature range of room temperature to the reflux temperature of the inert solvent used. Although the reaction time is varied depending on the scale of reaction, the reaction temperature, etc., it may be properly chosen in a range of several minutes to 48 hours.

After completion of the reaction, the desired compound is isolated from the reaction solution containing the desired compound by a conventional method, and if necessary, purified by recrystallization, column chromatography, etc., whereby the desired compound can be produced. The desired compound can be subjected to the subsequent reaction without isolation from the reaction solution.

The phthalic anhydride derivative of the general formula (V) can be produced by the process described in J. Org. Chem., 52, 129 (1987), J. Am. Chem. Soc., 51, 1865 (1929), J. Am. Chem. Soc., 63, 1542 (1941), etc. The aniline of the general formula (IV) can be produced by the process described in J. Org. Chem., 29, 1 (1964), Angew. Chem. Int. Ed. Engl., 24, 871 (1985), Synthesis, 1984, 667, Bulletin of the Chemical Society of Japan, 1973, 2351, DE-2606982, JP-A-1-90163, etc.

(2) General Formula (III)→General Formula (I-1)

In this reaction, there can be used the inert solvents exemplified above as the inert solvent used in the reaction (1).

Since the reaction is an equimolar reaction, it is sufficient that the reactants are used in equimolar amounts, though the amine of the general formula (II) may be used in excess.

As to the reaction temperature, the reaction can be carried out in a temperature range of room temperature to the reflux temperature of the inert solvent used. Although the reaction time is varied depending on the scale of reaction, the reaction temperature, etc., it may be properly chosen in a range of several minutes to 48 hours.

After completion of the reaction, the desired compound is isolated from the reaction solution containing the desired compound by a conventional method, and if necessary, purified by recrystallization, column chromatography, etc., whereby the desired compound can be produced.

Production process 2

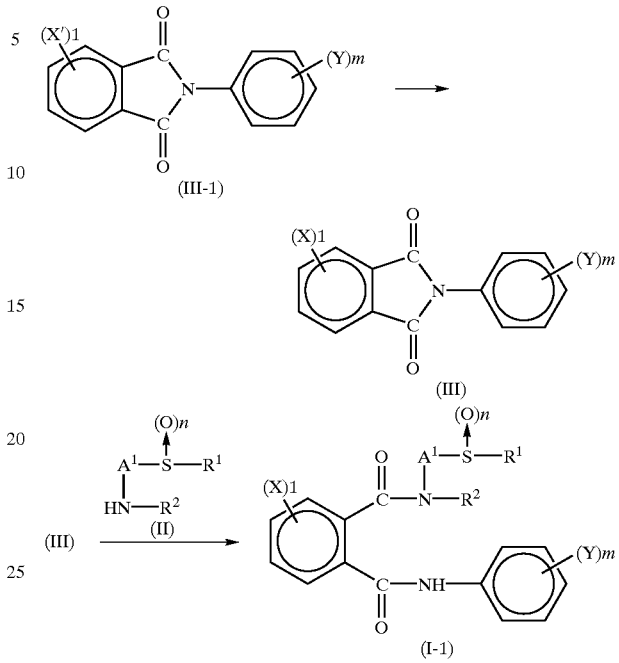

wherein $R^1$, $R^2$, $A^1$, X, Y, l, m and n are as defined above, X' is a halogen atom or a nitro group, provided that X is other than a hydrogen atom or a nitro group.

A phthalimide derivative of the general formula (III-1) is reacted with a reactant corresponding to X in the presence of an inert solvent to obtain a phthalimide derivative of the general formula (III). The phthalimide derivative (III) is reacted with an amine of the general formula (II) after or without being isolated, whereby a phthalamide derivative of the general formula (I-1) can be produced.

(1) General Formula (III-1)→General Formula (III)

This reaction can be carried out according to the methods described in J. Org. Chem., 42, 3415 (1977), Tetrahedron, 25, 5921 (1969), Synthesis, 1984, 667, Chem. Lett., 1973, 471, J. Org. Chem., 39, 3318 (1974), J. Org. Chem., 39, 3327 (1974), etc.

(2) General Formula (III)→General Formula (I-1)

This reaction can be carried out according to production process 1-(2).

Production process 3

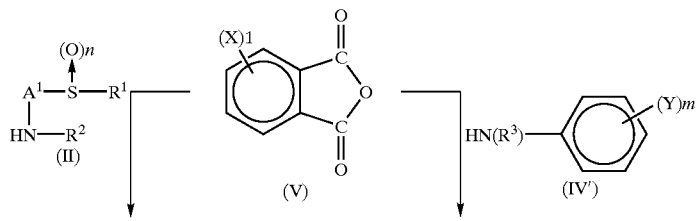

-continued

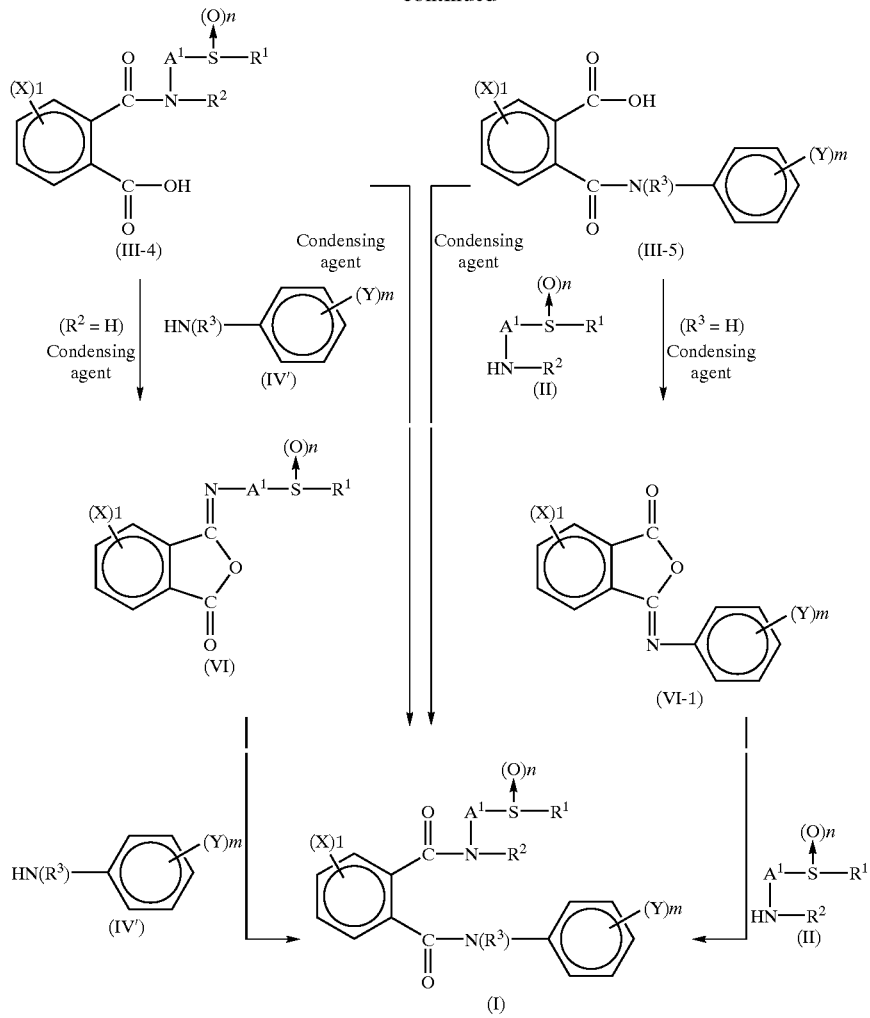

wherein $R^1, R^2, R^3, A^1, X, Y, l, m$ and $n$ are as defined above.

A phthalic anhydride derivative of the general formula (V) is reacted with an amine of the general formula (II) in the presence of an inert solvent to obtain a phthalamic acid of the general formula (III-4). The phthalamic acid (III-4) is treated as follows after or without isolation. When $R^2$ of the phthalamic acid (III-4) is a hydrogen atom, the phthalamic acid (III-4) is condensed into a compound of the general formula (VI) in the presence of a condensing agent, and the compound (VI) is reacted with an aniline of the general formula (IV') in the presence of an inert solvent after or without being isolated. When $R^2$ of the phthalamic acid (III-4) is other than a hydrogen atom, the phthalamic acid (III-4) is condensed with an aniline of the general formula (IV) in the presence of a condensing agent. Thus, a phthalamide derivative of the general formula (I) can be produced.

Alternatively, a phthalic anhydride derivative of the general formula (V) is reacted with an aniline of the general formula (IV') in the presence of an inert solvent to obtain a phthalamic acid of the general formula (III-5). The phthalamic acid (III-5) is treated as follows after or without isolation. When $R^3$ of the phthalamic acid (III-5) is a hydrogen atom, the phthalamic acid (III-5) is condensed into a compound of the general formula (VI-1) in the presence of a condensing agent, and the compound (VI-1) is reacted with an amine of the general formula (II) in the presence of an inert solvent after or without being isolated. When $R^3$ of the phthalamic acid (III-5) is other than a hydrogen atom, the phthalamic acid (III-5) is condensed with an amine of the general formula (II) in the presence of a condensing agent. Thus, a phthalamide derivative of the general formula (I) can be produced.

(1) General formula (V) or general formula (VI-1)→General Formula (III-4) or General Formula (I), respectively The desired compound can be produced by this reaction in the same manner as in production process 1-(2).

(2) General Formula (III-4) or General Formula (III-5) →General Formula (VI) or General Formula (VI-1), respectively The desired compound can be produced by this reaction according to the method described in J. Med. Chem., 10, 982 (1967).

(3) General Formula (VI) or General Formula (V)→General Formula (I) or General Formula (VII-5), respectively The desired compound can be produced by this reaction in the same manner as in production process 1-(2).

(4) General Formula (III-4) or General Formula (III-5) →General Formula (I)

The desired compound can be produced by reacting the phthalamic acid derivative of the general formula (III-4) or the general formula (III-5) with the aniline of the general formula (IV') or the amine of the general formula (II), respectively, in the presence of a condensing agent and an inert solvent. If necessary, the reaction can be carried out in the presence of a base.

The inert solvent used in the reaction includes, for example, tetrahydrofuran, diethyl ether, dioxane, chloroform and dichloromethane. As the condensing agent used in the reaction, any condensing agent may be used so long as it is used in usual amide synthesis. The condensing agent includes, for example, Mukaiyama reagent (e.g. 2-chloro-N-methylpyridinium iodide), 1,3-dicyclohexylcarbodiimide (DCC), carbonyldiimidazole (CDI) and diethyl phosphorocyanidate (DEPC). The amount of the condensing agent used may be properly chosen in a range of 1 mole to excess moles per mole of the phthalamic acid derivative of the general formula (III-4) or the general formula (III-5).

As the base usable in the reaction, there can be exemplified organic bases such as triethylamine, pyridine, etc. and inorganic bases such as potassium carbonate, etc. The amount of the base used may be properly chosen in a range of 1 mole to excess moles per mole of the phthalamic acid derivative of the general formula (III-4) or the general formula (III-5).

As to the reaction temperature, the reaction can be carried out in a temperature range of 0° C. to the boiling point of the inert solvent used. Although the reaction time is varied depending on the scale of reaction, the reaction temperature, etc., it ranges from several minutes to 48 hours.

After completion of the reaction, the desired compound is isolated from the reaction solution containing the desired compound by a conventional method, and if necessary, purified by recrystallization, column chromatography, etc., whereby the desired compound can be produced.

Production Process 4

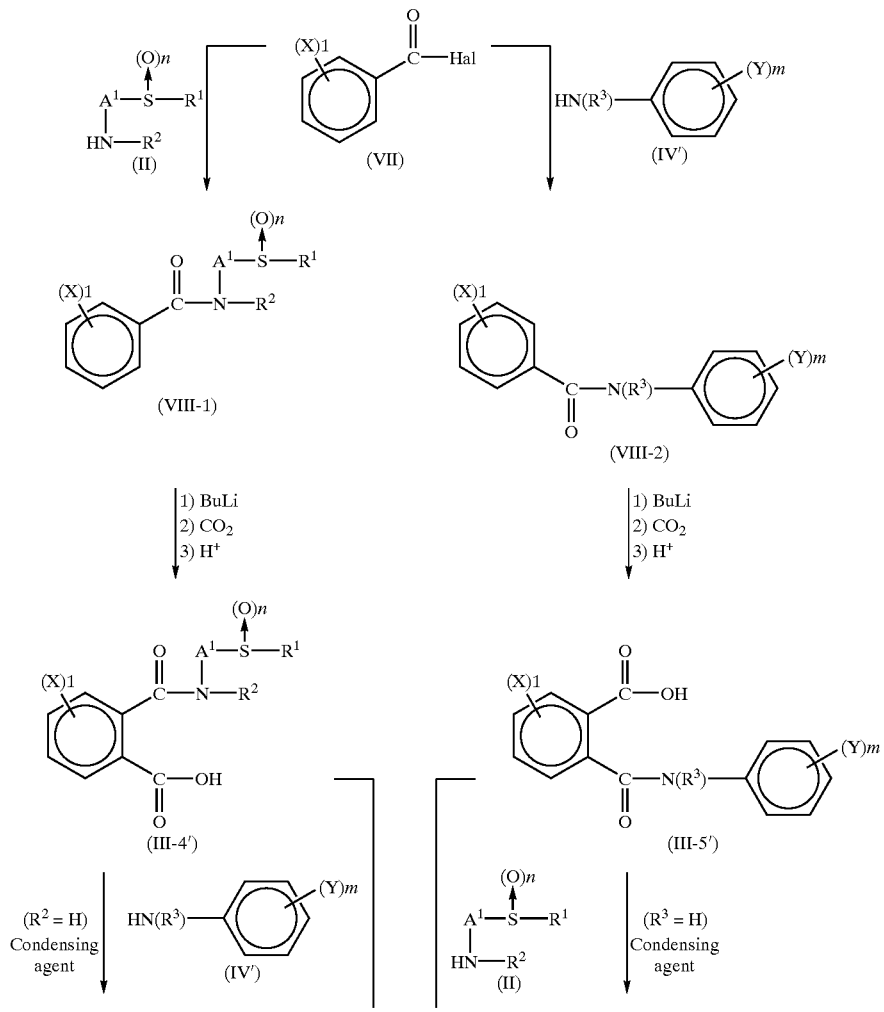

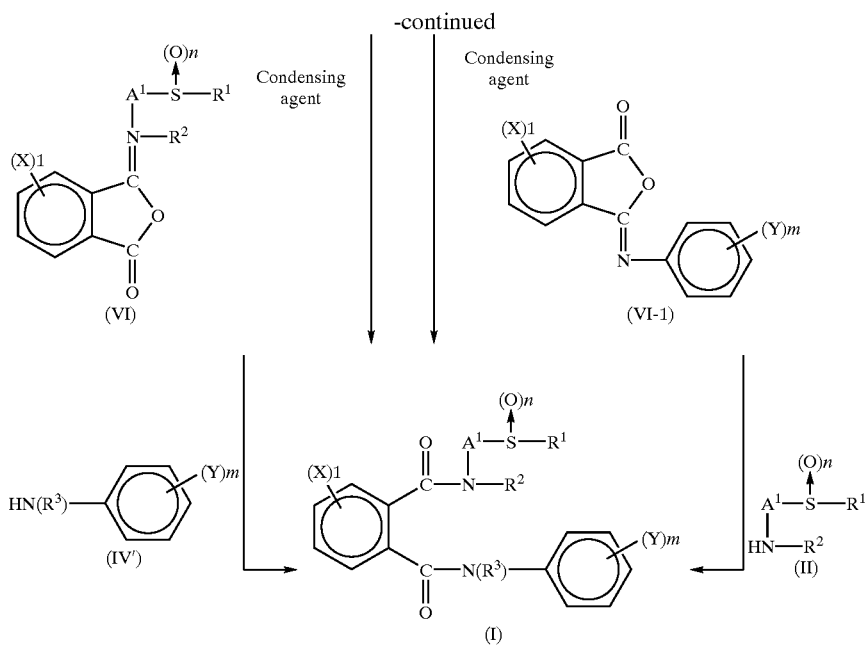

wherein $R^1$, $R^2$, $A^1$, X, Y, l, m and n are as defined above, and Hal is halogen atom.

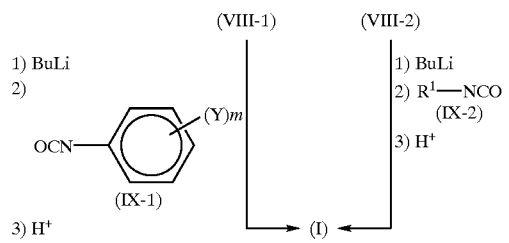

wherein $R^1$, Y and m are as defined above.

A benzoyl halide of the general formula (VII) is reacted with an amine derivative of the general formula (II) or (IV') in the presence of an inert solvent to obtain a benzamide of the general formula (VIII-1) or (VIII-2). The benzamide (VIII-1) or (VIII-2) is ortho-metallized with a metallic reagent such as butyllithium or the like and then directly reacted with an isocyanate of the general formula (IX-1) or (IX-2). Alternatively, the benzamide (VIII-1) or (VIII-2) is reacted with carbon dioxide to obtain a phthalamic acid of the general formula (III-4') or (III-5') and then treated in the same manner as in Production process 3-(1) to (4). Thus, a phthalamide derivative of the general formula (I) can be produced.

(1) General Formula (VII)→General Formula (VIII-1) or General Formula (VIII-2)

The desired compound can be produced according to the description of J. Org. Chem. 32, 3069 (1967), etc.

(2) General Formula (VIII-1) or General Formula (VIII-2) →General Formula (I)

The desired compound can be produced by converting a benzamide of the general formula (VIII-1) or (VIII-2) into an ortho-lithio compound according to the description of J. Org. Chem. 29, 853 (1964) and then reacted with an isocyanate of the general formula (IX-1) or (IX-2) at a temperature of −80° C. to room temperature, whereby the desired compound can be produced.

(3) General Formula (VIII-1) or General Formula (VIII-2) →General Formula (III-4') or General Formula (III-5'), respectively The desired compound can be produced by the same conversion into an ortho-lithio compound as in (2), followed by introduction of carbon dioxide at a temperature of −80° C. to room temperature.

After completion of the reaction, the desired compound is isolated from the reaction solution by the conventional method and, if necessary, purified by recrystallization, column chromatography, etc., whereby the desired compound can be produced.

(4) General Formula (III-4') or General Formula (III-5') →General Formula (I)

The desired compound can be produced by the same procedure as in production process 3-(1) to (4).

Production process 5

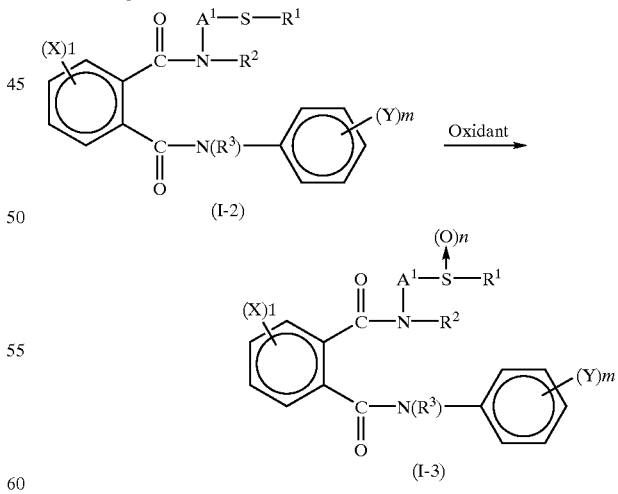

wherein $R^1$, $R^2$, $R^3$, $A^1$, X, Y, l, m and n are as defined above, provided that n cannot be an integer of 0.

A phthalamide derivative of the general formula (I-2) is reacted with an oxidant in the presence of an inert solvent, whereby a phthalamide derivative of the general formula (I-3) can be produced.

As the inert solvent used in this reaction, there can be exemplified halogenated hydrocarbons such as dichloromethane, chloroform, etc., aromatic hydrocarbon such as toluene, xylene, etc., acids such as acetic acid, etc., and alcohols such as methanol, ethanol, propanol, etc.

As the oxidant, there can be exemplified m-chloroperbenzoic acid, peracetic acid, potassium metaperiodate, potassium hydrogen persulfate (Oxon), hydrogen peroxide, etc. The amount of the oxidant may be properly selected in the range of 0.5 to 3 equivalents per equivalent of the phthalic acid diamide derivative of the general formula (I-2).

As to the reaction temperature, the reaction can be carried out in a temperature range of −50° C. to the boiling temperature zone of the inert solvent used. Though the reaction time is varied depending on the reaction temperature and scale of the reaction, it is in the range of several minutes to 24 hours.

After completion of the reaction, the desired compound is isolated from the reaction solution containing the desired compound by a conventional method and, if necessary, purified by recrystallization, column chromatography, etc., whereby the desired compound can be produced.

Next, typical phthalamide derivatives of the general formula (I) are exemplified in Tables 1, 2 and 3. The present invention is by no means limited by these examples.

General formula (I)

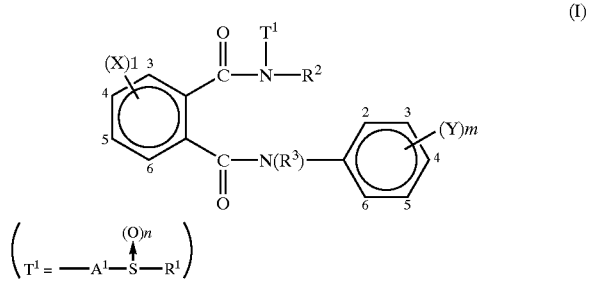

TABLE 1

($R^2=R^3=H$)

| No | $T^1$ | $(X)_1$ | $(Y)_m$ | Property mp (° C.) |
|---|---|---|---|---|
| 1 | $CH(CH_3)CH_2SCH_3$ | 3-I | $2\text{-}CH_3\text{-}4\text{-}C_2F_5$ | 179–180 |
| 2 | $CH(CH_3)CH_2S\text{-}i\text{-}C_3H_7$ | 3-I | $2\text{-}CH_3\text{-}4\text{-}C_2F_5$ | Paste |
| 3 | $CH(CH_3)CH_2SCH_3$ | 3-I | $2\text{-}CH_3\text{-}4\text{-}OCF_3$ | 147 |
| 4 | $CH(CH_3)CH_2SCH_3$ | 3-I | $2\text{-}CH_3\text{-}4\text{-}OCHF_2$ | 107 |
| 5 | $CH(CH_3)CH_2S\text{-}i\text{-}C_3H_7$ | 3-I | $2\text{-}CH_3\text{-}4\text{-}OCF_3$ | 126 |
| 6 | $CH(CH_3)CH_2SCH_3$ | 3-I | $2\text{-}CH_3\text{-}4\text{-}i\text{-}C_3F_7$ | 197–199 |
| 7 | $CH(CH_3)CH_2SCH_3$ | 3-I | $2\text{-}Cl\text{-}4\text{-}C_2F_5$ | 143 |
| 8 | $CH(CH_3)CH_2SCH_3$ | 3-I | $4\text{-}OCF_3$ | 171–178 |
| 9 | $CH(CH_3)CH_2SCH_3$ | 3-I | $2\text{-}CH_3\text{-}4\text{-}Cl$ | 179 |
| 10 | $CH(CH_3)CH_2SCH_3$ | 3-F | $2\text{-}CH_3\text{-}4\text{-}i\text{-}C_3F_7$ | 146–154 |
| 11 | $CH(CH_3)CH_2SCH_3$ | 3-F | $2\text{-}CH_3\text{-}4\text{-}C_2F_5$ | 140 |
| 12 | $CH(CH_3)CH_2SCH_3$ | 3-F | $2\text{-}CH_3\text{-}4\text{-}OCF_3$ | 122–130 |
| 13 | $CH(CH_3)CH_2SCH_3$ | 3-F | $2\text{-}CH_3\text{-}4\text{-}OCHF_2$ | 149–154 |
| 14 | $CH(CH_3)CH_2SCH_3$ | H | $2\text{-}CH_3\text{-}4\text{-}C_2F_5$ | 139–146 |
| 15 | $CH(CH_3)CH_2SCH_3$ | H | $2\text{-}CH_3\text{-}4\text{-}OCF_3$ | 140–144 |
| 16 | $CH(CH_3)CH_2SCH_3$ | H | $2\text{-}CH_3\text{-}4\text{-}i\text{-}C_3F_7$ | 139–145 |
| 17 | $CH(CH_3)CH_2SPh$ | 3-I | $2\text{-}CH_3\text{-}4\text{-}C_2F_5$ | Paste |
| 18 | $CH(CH_3)CH_2SPh$ | 3-I | $2\text{-}CH_3\text{-}4\text{-}OCF_3$ | Paste |
| 19 | $CH(CH_3)CH_2SPh$ | 3-I | $2\text{-}CH_3\text{-}4\text{-}i\text{-}C_3F_7$ | Paste |
| 20 | $CH(CH_3)CH_2SPh$ | 3-I | $2\text{-}C_2H_5\text{-}4\text{-}C_2F_5$ | Paste |
| 21 | $CH(CH_3)CH_2SC_2H_5$ | 3-I | $2\text{-}CH_3\text{-}4\text{-}C_2F_5$ | Paste |
| 22 | $CH(CH_3)CH_2SC_2H_5$ | 3-I | $2\text{-}CH_3\text{-}4\text{-}i\text{-}C_3F_7$ | 107 |
| 23 | $CH(CH_3)CH_2SC_2H_5$ | 3-I | $2\text{-}CH_3\text{-}4\text{-}OCF_3$ | 143 |
| 24 | $CH(CH_3)CH_2SC_2H_5$ | 3-I | $2\text{-}CH_3\text{-}4\text{-}Cl$ | 161–166 |
| 25 | $CH(CH_3)CH_2SC_2H_5$ | 3-F | $2\text{-}CH_3\text{-}4\text{-}i\text{-}C_3F_7$ | 142 |
| 26 | $CH(CH_3)CH_2SC_2H_5$ | 3-F | $2\text{-}CH_3\text{-}4\text{-}C_2F_5$ | Paste |
| 27 | $CH(CH_3)CH_2SC_2H_5$ | 3-F | $2\text{-}CH_3\text{-}4\text{-}OCF_3$ | 142–147 |
| 28 | $CH(CH_3)CH_2SOCH_3$ | 3-I | $2\text{-}CH_3\text{-}4\text{-}C_2F_5$ | 94 |
| 29 | $CH(CH_3)CH_2SO_2CH_3$ | 3-I | $2\text{-}CH_3\text{-}4\text{-}C_2F_5$ | 100 |
| 30 | $CH(CH_3)CH_2SOCH_3$ | 3-I | $2\text{-}CH_3\text{-}4\text{-}i\text{-}C_3F_7$ | 82 |
| 31 | $CH(CH_3)CH_2SO_2CH_3$ | 3-I | $2\text{-}CH_3\text{-}4\text{-}i\text{-}C_3F_7$ | 134 |
| 32 | $CH(CH_3)CH_2SCH_3$ | 3-I | $2\text{-}CH_3\text{-}4\text{-}SCF_3$ | 194–195 |
| 33 | $CH(CH_3)CH_2S\text{-}i\text{-}C_4H_9$ | 3-I | $2\text{-}CH_3\text{-}4\text{-}i\text{-}C_3F_7$ | 164–172 |
| 34 | $CH(CH_3)CH_2S\text{-}i\text{-}C_4H_9$ | 3-I | $2\text{-}CH_3\text{-}4\text{-}C_2F_5$ | 159–160 |
| 35 | $CH(CH_3)CH_2S\text{-}i\text{-}C_4H_9$ | 3-I | $2\text{-}CH_3\text{-}4\text{-}OCF_3$ | 155–159 |
| 36 | $CH(CH_2SCH_3)_2$ | 3-I | $2\text{-}CH_3\text{-}4\text{-}C_2F_5$ | 145 |
| 37 | $CH(CH_3)CH_2SCH_3$ | 3,4-$Cl_2$ | $2\text{-}CH_3\text{-}4\text{-}OCF_3$ | 197–199 |
| 38 | $CH(CH_3)CH_2SCH_3$ | 5,6-$Cl_2$ | $2\text{-}CH_3\text{-}4\text{-}OCF_3$ | 213–214 |
| 39 | $CH(CH_3)CH_2SCH_3$ | 3,4-$Cl_2$ | $2\text{-}CH_3\text{-}4\text{-}C_2F_5$ | 221–222 |
| 40 | $CH(CH_3)CH_2SCH_3$ | 5,6-$Cl_2$ | $2\text{-}CH_3\text{-}4\text{-}C_2F_5$ | 199–200 |
| 41 | $CH(CH_3)CH_2SCH_3$ | 3,4-$Cl_2$ | $2\text{-}CH_3\text{-}4\text{-}i\text{-}C_3F_7$ | 215–216 |
| 42 | $CH(CH_3)CH_2SCH_3$ | 5,6-$Cl_2$ | $2\text{-}CH_3\text{-}4\text{-}i\text{-}C_3F_7$ | 220–221 |
| 43 | $CH(CH_3)CH_2SCH_3$ | 4-Cl | $2\text{-}CH_3\text{-}4\text{-}C_2F_5$ | 178–179 |
| 44 | $CH(CH_3)CH_2SCH_3$ | 3,4-$F_2$ | $2\text{-}CH_3\text{-}4\text{-}OCF_3$ | 175–176 |
| 45 | $CH(CH_3)CH_2SCH_3$ | 4,5-$F_2$ | $2\text{-}CH_3\text{-}4\text{-}OCF_3$ | 118–120 |
| 46 | $CH(CH_3)CH_2SCH_3$ | 3-I | $2\text{-}CH_3\text{-}4\text{-}OC\text{—}(C_2H_5)\text{=}C(CF_3)_2$ | 196–197 |

TABLE 1-continued ($R^2=R^3=H$)

| No | $T^1$ | $(X)l$ | $(Y)m$ | Property mp (° C.) |
|---|---|---|---|---|
| 47 | $CH(CH_3)CH_2SCH_3$ | 3-I | 2-Cl-4-$OCF_2$—CHFO-5 | 198 |
| 48 | $CH(CH_3)CH_2SCH_3$ | 3-I | 2-Cl-4-OCHF-$CF_2$O-5 | 192 |
| 49 | $CH(CH_3)CH_2SCH_3$ | 3-I | 2-$OCH_3$-4-$C_2F_5$ | 170 |
| 50 | $CH(CH_3)CH_2SCH_3$ | 3-I | 2-$C_2H_5$-4-$C_2F_5$ | 125 |
| 51 | $(CH_2)_2SCH_3$ | 6-I | 2-$CH_3$-4-$OCF_3$ | 130–133 |
| 52 | $(CH_2)_2SCH_3$ | 3-I | 2-$CH_3$-4-$OCF_3$ | 145–150 |
| 53 | $(CH_2)_2SCH_3$ | 3-I | 2-$CH_3$-4-$C_2F_5$ | Amorphous |
| 54 | $(CH_2)_2SCH_3$ | 3-I | 2-$CH_3$-4-i-$C_3F_7$ | Amorphous |
| 55 | $(CH_2)_3SCH_3$ | 3-I | 2-$CH_3$-4-$OCF_3$ | 144–147 |
| 56 | $(CH_2)_3SCH_3$ | 3-I | 2-$CH_3$-4-$C_2F_5$ | 165–168 |
| 57 | $(CH_2)_3SCH_3$ | 3-I | 2-$CH_3$-4-i-$C_3F_7$ | 156–159 |
| 58 | $(CH_2)_2$S-i-$C_3H_7$ | 3-I | 2-$CH_3$-4-$OCF_3$ | 189–192 |
| 59 | $(CH_2)_2$S-i-$C_3H_7$ | 3-I | 2-$CH_3$-4-$C_2F_5$ | 153–155 |
| 60 | $(CH_2)_2$S-i-$C_3H_7$ | 3-I | 2-$CH_3$-4-i-$C_3F_7$ | 158–160 |
| 61 | $CH(CH_3)CH_2$S-2-Pyi | 3-I | 2-$CH_3$-4-$C_2F_5$ | Amorphous |
| 62 | $CH(CH_3)CH_2$S-2-Pyi | 3-I | 2-$CH_3$-4-i-$C_3F_7$ | 140–142 |
| 63 | $CH(CH_3)CH_2$S-n-$C_4H_9$ | 3-I | 2-$CH_3$-4-$OCF_3$ | 137–139 |
| 64 | $CH(CH_3)CH_2$S-n-$C_4H_9$ | 3-I | 2-$CH_3$-4-$C_2F_5$ | Amorphous |
| 65 | $CH(CH_3)CH_2SCH_3$ | 3-I | 2-Cl-4-i-$C_3F_7$ | 190 |
| 66 | $CH(CH_3)CH_2SCH_3$ | 3-I | 2-$C_2H_5$-4-i-$C_3F_7$ | 205 |
| 67 | $CH(CH_2SCH_3)_2$ | 3-I | 2-$CH_3$-4-i-$C_3F_7$ | 181 |
| 68 | $CH(CH_2SCH_3)_2$ | 3-I | 2-$CH_3$-4-$OCF_2CHF_2$ | 169–176 |
| 69 | $CH(CH_2SCH_3)_2$ | 3-I | 2-$CH_3$-4-$OCF_3$ | 131–139 |
| 70 | $CH(CH_2SCH_3)_2$ | 3-I | 2-$CH_3$-4-$OCHF_2$ | 142 |
| 71 | $(CH_2)_2SC_2H_5$ | 3-I | 2-$CH_3$-4-$OCF_3$ | 157–161 |
| 72 | $(CH_2)_2SC_2H_5$ | 3-I | 2-$CH_3$-4-$C_2F_5$ | 152–155 |
| 73 | $(CH_2)_2SC_2H_5$ | 3-I | 2-$CH_3$-4-i-$C_3F_7$ | 159–162 |
| 74 | $CH(CH_3)CH_2$S-2-Pyi | 3-I | 2-$CH_3$-4-$OCF_3$ | 203 |
| 75 | $CH(CH_3)CH_2$SO-2-Pyi | 3-I | 2-$CH_3$-4-$C_2F_5$ | 110–111 |
| 76 | $CH(CH_3)CH_2SO_2$-2-Pyi | 3-I | 2-$CH_3$-4-i-$C_3F_7$ | 99–100 |
| 77 | $CH(CH_3)CH_2$S-n-$C_6H_{13}$ | 3-I | 2-$CH_3$-4-$OCF_3$ | Amorphous |
| 78 | $CH(CH_3)CH_2$S-n-$C_6H_{13}$ | 3-I | 2-$CH_3$-4-i-$C_3F_7$ | 152–153 |
| 79 | $CH(CH_3)CH_2SCH_3$ | 3-Br | 2-$CH_3$-4-i-$C_3F_7$ | 201–202 |
| 80 | $CH(CH_3)CH_2SCH_3$ | 3-Br | 2-$CH_3$-4-$OCF_3$ | 195 |
| 81 | $CH(CH_3)CH_2SCH_3$ | 3-Br | 2-$CH_3$-4-$C_2F_5$ | 194–195 |
| 82 | $CH(CH_3)CH_2$S-c-$C_6H_{11}$ | 3-I | 2-$CH_3$-4-$OCF_3$ | 166–167 |
| 83 | $CH(CH_3)CH_2$S-t-$C_4H_9$ | 3-I | 2-$CH_3$-4-$OCF_3$ | 188–189 |
| 84 | $CH(CH_3)CH_2$S-t-$C_4H_9$ | 3-I | 2-$CH_3$-4-$C_2F_5$ | 183–184 |
| 85 | $CH(CH_3)CH_2$S-c-$C_6H_{11}$ | 3-I | 2-$CH_3$-4-$C_2F_5$ | 102–103 |
| 86 | $CH(CH_3)CH_2$S-c-$C_6H_{11}$ | 3-I | 2-$CH_3$-4-i-$C_3F_7$ | 95–96 |
| 87 | $CH(CH_3)CH_2SOCH_3$ | 3-Br | 2-$CH_3$-4-$OCF_3$ | 212–213 |
| 88 | $CH(CH_3)CH_2SO_2CH_3$ | 3-Br | 2-$CH_3$-4-$OCF_3$ | 93 |
| 89 | $CH(Ph)CH_2SCH_3$ | 3-I | 2-$CH_3$-4-i-$C_3F_7$ | 168–170 |
| 90 | $CH(Ph)CH_2SCH_3$ | 3-I | 2-$CH_3$-4-$C_2F_5$ | 157–159 |
| 91 | $CH(Ph)CH_2SCH_3$ | 3-I | 2-$CH_3$-4-$OCF_3$ | 178–180 |
| 92 | $CH(CH_3)(CH_2)_3SCH_3$ | 3-I | 2-$CH_3$-4-i-$C_3F_7$ | 160–161 |
| 93 | $CH(CH_3)(CH_2)_3SCH_3$ | 3-I | 2-$CH_3$-4-$C_2F_5$ | 147–149 |
| 94 | $CH(CH_3)(CH_2)_3SCH_3$ | 3-I | 2-$CH_3$-4-$OCF_3$ | 183–185 |
| 95 | $CH(CH_3)CH_2SOCH_3$ | 3-Br | 2-$CH_3$-4-$C_2F_5$ | 90 |
| 96 | $CH(CH_3)CH_2SO_2CH_3$ | 3-Br | 2-$CH_3$-4-$C_2F_5$ | 95 |
| 97 | $CH(CH_3)CH_2SO_2CH_3$ | 3-Br | 2-$CH_3$-4-i-$C_3F_7$ | 153–155 |
| 98 | $CH(CH_3)CH_2SCH_3$ | 3-Cl | 2-$CH_3$-4-$OCF_3$ | 188–189 |
| 99 | $CH(CH_3)CH_2SCH_3$ | 3-Cl | 2-$CH_3$-4-i-$C_3F_7$ | 202–203 |
| 100 | $CH(CH_3)CH_2SO_2CH_3$ | 3-Cl | 2-$CH_3$-4-$OCF_3$ | 104–105 |
| 101 | $CH(CH_3)CH_2SO_2CH_3$ | 3-Cl | 2-$CH_3$-4-i-$C_3F_7$ | 155–156 |
| 102 | $CH(CH_3)CH_2SO_2CH_3$ | 3-I | 2-Cl-4-$OCHFCF_2$O-5 | 198 |
| 103 | $CH(CH_3)CH_2SO_2CH_3$ | 3-I | 2-Cl-4-$OCF_2$CHFO-5 | 195 |
| 104 | $CH(CH_3)CH_2SCH_3$ | 3-$NO_2$ | 2-$CH_3$-4-$OCF_3$ | 181 |
| 105 | $CH(CH_3)CH_2SCH_3$ | 3-$NO_2$ | 2-$CH_3$-4-$C_2F_5$ | 190–193 |
| 106 | $CH(CH_3)CH_2SCH_3$ | 3-$NO_2$ | 2-$CH_3$-4-i-$C_3F_7$ | 219 |
| 107 | $CH(CH_3)CH_2SCH_3$ | 4-I | 2-$CH_3$-4-$OCF_3$ | 179 |
| 108 | $CH(CH_3)CH_2SCH_3$ | 4-I | 2-$CH_3$-4-$C_2F_5$ | 204 |
| 109 | $CH(CH_3)CH_2SCH_3$ | 4-I | 2-$CH_3$-4-i-$C_3F_7$ | 169–176 |
| 110 | $CH(CH_3)CH_2SCH_3$ | 5-I | 2-$CH_3$-4-$OCF_3$ | 127–128 |
| 111 | $CH(CH_3)CH_2SCH_3$ | 5-I | 2-$CH_3$-4-$C_2F_5$ | 143 |
| 112 | $CH(CH_3)CH_2SCH_3$ | 5-I | 2-$CH_3$-4-i-$C_3F_7$ | 189 |
| 113 | $CH(CH_3)CH_2SCH_3$ | 3-Cl | 2-$CH_3$-4-$C_2F_5$ | 189–190 |
| 114 | $CH(CH_3)CH_2SO_2CH_3$ | 3-Cl | 2-$CH_3$-4-$C_2F_5$ | 84–87 |
| 115 | $CH(CH_3)CH_2SCH_3$ | 6-Cl | 2-$CH_3$-4-$C_2F_5$ | 102–103 |
| 116 | $CH(CH_3)CH_2SO_2CH_3$ | 6-Cl | 2-$CH_3$-4-$C_2F_5$ | 233–234 |
| 117 | $CH(CH_3)CH_2$S-t-$C_4H_9$ | 3-I | 2-$CH_3$-4-i-$C_3F_7$ | 252–256 |
| 118 | $CH(CH_3)CH_2SO_2$-2-Pyi | 3-I | 2-$CH_3$-4-$C_2F_5$ | 95–100 |
| 119 | $CH(CH_3)CH_2SO_2$-2-Pyi | 3-I | 2-$CH_3$-4-$OCF_3$ | 92–93 |
| 120 | $CH(C_2H_5)CH_2SCH_3$ | 3-I | 2-$CH_3$-4-i-$C_3F_7$ | 190 |

TABLE 1-continued ($R^2=R^3=H$)

| No | $T^1$ | $(X)_l$ | $(Y)_m$ | Property mp (° C.) |
|---|---|---|---|---|
| 121 | $C(CH_3)_2CH_2SCH_3$ | 3-I | $2\text{-}CH_3\text{-}4\text{-}C_2F_5$ | 194–196 |
| 122 | $C(CH_3)_2CH_2SCH_3$ | 3-I | $2\text{-}CH_3\text{-}4\text{-}i\text{-}C_3F_7$ | 205–206 |
| 123 | $C(CH_3)_2CH_2SO_2CH_3$ | 3-I | $2\text{-}CH_3\text{-}4\text{-}C_2F_5$ | 88–90 |
| 124 | $C(CH_3)_2CH_2SO_2CH_3$ | 3-1 | $2\text{-}CH_3\text{-}4\text{-}i\text{-}C_3F_7$ | 88–90 |
| 125 | $C(CH_3)_2CH_2SOCH_3$ | 3-I | $2\text{-}CH_3\text{-}4\text{-}C_2F_5$ | 74–76 |
| 126 | $C(CH_3)_2CH_2SOCH_3$ | 3-I | $2\text{-}CH_3\text{-}4\text{-}i\text{-}C_3F_7$ | 90–95 |
| 127 | $CH(C_2H_5)(CH_2)_2SCH_3$ | 3-I | $2\text{-}CH_3\text{-}4\text{-}C_2F_5$ | 170 |
| 128 | $CH(C_2H_5)(CH_2)_2SCH_3$ | 3-I | $2\text{-}CH_3\text{-}4\text{-}OCF_3$ | 175 |
| 129 | $CH(CH_3)CH_2SCH_3$ | $3\text{-}SCF_3$ | $2\text{-}CH_3\text{-}4\text{-}C_2F_5$ | 201–203 |
| 130 | $CH(CH_3)CH_2SCH_3$ | $3\text{-}SCF_3$ | $2\text{-}CH_3\text{-}4\text{-}i\text{-}C_3F_7$ | 176–178 |
| 131 | $CH(CH_3)CH_2SCH_3$ | $3\text{-}SOCF_3$ | $2\text{-}CH_3\text{-}4\text{-}C_2F_5$ | 183–185 |
| 132 | $CH(CH_3)CH_2SCH_3$ | $3\text{-}SOCF_3$ | $2\text{-}CH_3\text{-}4\text{-}i\text{-}C_3F_7$ | 154 |
| 133 | $CH(CH_3)(CH_2)_3SOCH_3$ | 3-I | $2\text{-}CH_3\text{-}4\text{-}C_2F_5$ | 135 |
| 134 | $CH(CH_3)(CH_2)_3SO_2CH_3$ | 3-I | $2\text{-}CH_3\text{-}4\text{-}C_2F_5$ | 163 |
| 135 | $CH(CH_3)(CH_2)_3SOCH_3$ | 3-I | $2\text{-}CH_3\text{-}4\text{-}i\text{-}C_3F_7$ | 172–175 |
| 136 | $CH(CH_3)(CH_2)_3SO_2CH_3$ | 3-I | $2\text{-}CH_3\text{-}4\text{-}i\text{-}C_3F_7$ | 204 |
| 137 | $CH(Ph)CH_2SOCH_3$ | 3-I | $2\text{-}CH_3\text{-}4\text{-}i\text{-}C_3F_7$ | 142 |
| 138 | $CH(Ph)CH_2SO_2CH_3$ | 3-I | $2\text{-}CH_3\text{-}4\text{-}i\text{-}C_3F_7$ | 203 |
| 139 | $CH(CH_3)CH_2SO_2\text{-}t\text{-}C_4H_9$ | 3-I | $2\text{-}CH_3\text{-}4\text{-}OCF_3$ | 90–92 |
| 140 | $C(CH_3)_2CH_2SCH_3$ | 3-I | $2\text{-}CH_3\text{-}4\text{-}OCF_3$ | 172–173 |
| 141 | $C(CH_3)_2CH_2SOCH_3$ | 3-I | $2\text{-}CH_3\text{-}4\text{-}OCF_3$ | 146–147 |
| 142 | $C(CH_3)_2CH_2SO_2CH_3$ | 3-I | $2\text{-}CH_3\text{-}4\text{-}OCF_3$ | 86–88 |
| 143 | $CH(CH_3)CH_2SOCH_3$ | 3-Cl | $2\text{-}CH_3\text{-}4\text{-}OCF_3$ | 199–200 |
| 144 | $CH(CH_3)CH_2SOCH_3$ | 3-Cl | $2\text{-}CH_3\text{-}4\text{-}C_2F_5$ | 152–155 |
| 145 | $CH(CH_3)CH_2SCH_3$ | 3-I | $2\text{-}CH_3\text{-}4\text{-}s\text{-}C_4F_9$ | 120 |
| 146 | $CH(CH_3)CH_2SCH_3$ | 3-I | $2\text{-}CH_3\text{-}4\text{-}i\text{-}C_3F_7\text{-}5\text{-}F$ | 210 |
| 147 | $CH(CH_3)CH_2SCH_3$ | 3-Cl-4-F | $2\text{-}CH_3\text{-}4\text{-}OCF_3$ | 188–190 |
| 148 | $CH(CH_3)CH_2SCH_3$ | 3-Cl-4-F | $2\text{-}CH_3\text{-}4\text{-}C_2F_6$ | 203–204 |
| 149 | $CH(CH_3)CH_2SCH_3$ | 3-Cl-4-F | $2\text{-}CH_3\text{-}4\text{-}i\text{-}C_3F_7$ | 226–227 |
| 150 | $CH(CH_3)(CH_2)_3SCH_3$ | 3-Cl | $2\text{-}CH_3\text{-}4\text{-}C_2F_5$ | 124 |
| 151 | $CH(CH_3)(CH_2)_3SCH_3$ | 6-Cl | $2\text{-}CH_3\text{-}4\text{-}C_2F_5$ | Paste |
| 152 | $CH(CH_3)(CH_2)_3SOCH_3$ | 3-Cl | $2\text{-}CH_3\text{-}4\text{-}C_2F_5$ | 150 |
| 153 | $CH(CH_3)(CH_2)_3SO_2CH_3$ | 3-Cl | $2\text{-}CH_3\text{-}4\text{-}C_2F_5$ | 117 |
| 154 | $CH(CH_3)(CH_2)_3SCH_3$ | 3-Cl | $2\text{-}CH_3\text{-}4\text{-}i\text{-}C_3F_7$ | 125 |
| 155 | $CH(CH_3)(CH_2)_3SCH_3$ | 6-Cl | $2\text{-}CH_3\text{-}4\text{-}i\text{-}C_3F_7$ | Paste |
| 156 | $CH(CH_3)(CH_2)_3SO_2CH_3$ | 3-Cl | $2\text{-}CH_3\text{-}4\text{-}i\text{-}C_3F_7$ | 115 |
| 157 | $CH(CH_3)CH_2SCH_3$ | 3-I | $2\text{-}CH_3\text{-}4\text{-}CF_3$ | 187 |
| 158 | $CH(CH_3)CH_2SCH_3$ | $3\text{-}OCH_2\text{—}O\text{-}4$ | $2\text{-}CH_3\text{-}4\text{-}C_2F_5$ | 110 |
| 159 | $CH(CH_3)(CH_2)_2SCH_3$ | 3-Cl | $2\text{-}CH_3\text{-}4\text{-}i\text{-}C_3F_7$ | 167–169 |
| 160 | $CH(CH_3)(CH_2)_2SCH_3$ | 3-Cl | $2\text{-}CH_3\text{-}4\text{-}C_2F_5$ | 169–171 |
| 161 | $CH(CH_3)(CH_2)_2SCH_3$ | 3-Cl | $2\text{-}CH_3\text{-}4\text{-}OCF_3$ | 183–184 |
| 162 | $CH(CH_3)(CH_2)_2SCH_3$ | 3-I | $2\text{-}CH_3\text{-}4\text{-}i\text{-}C_3F_7$ | 192–194 |
| 163 | $CH(CH_3)(CH_2)_2SCH_3$ | 3-I | $2\text{-}CH_3\text{-}4\text{-}C_2F_5$ | 200–201 |
| 164 | $CH(CH_3)(CH_2)_2SCH_3$ | 3-I | $2\text{-}CH_3\text{-}4\text{-}OCF_3$ | 193–194 |
| 165 | $CH(CH_3)CH(CH_3)SCH_3$ | 3-I | $2\text{-}CH_3\text{-}4\text{-}i\text{-}C_3F_7$ | 120 |
| 166 | $CH(CH_3)CH(CH_3)SO_2CH_3$ | 3-I | $2\text{-}CH_3\text{-}4\text{-}i\text{-}C_3F_7$ | 130 |
| 167 | $CH(CH_3)CH(CH_3)SC_2H_5$ | 3-I | $2\text{-}CH_3\text{-}4\text{-}i\text{-}C_3F_7$ | 105 |
| 168 | $CH(CH_3)CH(CH_3)SO_2C_2H_5$ | 3-I | $2\text{-}CH_3\text{-}4\text{-}i\text{-}C_3F_7$ | 105 |
| 169 | $C(CH_3)_2CH_2SCH_3$ | 3-Cl | $2\text{-}CH_3\text{-}4\text{-}i\text{-}C_3F_7$ | 199–200 |
| 170 | $C(CH_3)_2CH_2SCH_3$ | 3-Br | $2\text{-}CH_3\text{-}4\text{-}i\text{-}C_3F_7$ | 200–201 |
| 171 | $C(CH_3)_2CH_2SO_2CH_3$ | 3-Cl | $2\text{-}CH_3\text{-}4\text{-}i\text{-}C_3F_7$ | 86 |
| 172 | $C(CH_3)_2CH_2SOCH_3$ | 3-Cl | $2\text{-}CH_3\text{-}4\text{-}i\text{-}C_3F_7$ | 90 |
| 173 | $CH(CH_3)(CH_2)_4SCH_3$ | 3-I | $2\text{-}CH_3\text{-}4\text{-}C_2F_5$ | 156 |
| 174 | $CH(CH_3)(CH_2)_4SCH_3$ | 3-I | $2\text{-}CH_3\text{-}4\text{-}i\text{-}C_3F_7$ | 174 |
| 175 | $CH(CH_3)(CH_2)_4SC_2H_5$ | 3-I | $2\text{-}CH_3\text{-}4\text{-}C_2F_5$ | 147 |
| 176 | $CH(CH_3)(CH_2)_4SC_2H_5$ | 3-I | $2\text{-}CH_3\text{-}4\text{-}i\text{-}C_3F_7$ | 168 |
| 177 | $CH(CH_3)(CH_2)_4SOC_2H_5$ | 3-I | $2\text{-}CH_3\text{-}4\text{-}C_2F_5$ | 115 |
| 178 | $CH(CH_3)(CH_2)_4SOC_2H_5$ | 3-I | $2\text{-}CH_3\text{-}4\text{-}i\text{-}C_3F_7$ | 120 |
| 179 | $CH(CH_3)(CH_2)_4SO_2C_2H_5$ | 3-I | $2\text{-}CH_3\text{-}4\text{-}C_2F_5$ | 131 |
| 180 | $CH(CH_3)(CH_2)_4SO_2C_2H_5$ | 3-I | $2\text{-}CH_3\text{-}4\text{-}i\text{-}C_3F_7$ | 145 |
| 181 | $C(CH_3)_2CH_2SO_2CH_3$ | 3-Br | $2\text{-}CH_3\text{-}4\text{-}i\text{-}C_3F_7$ | 90–93 |
| 182 | $C(CH_3)_2CH_2SOCH_3$ | 3-Br | $2\text{-}CH_3\text{-}4\text{-}i\text{-}C_3F_7$ | 212–213 |
| 183 | $C(CH_3)_2CH_2SC_2H_5$ | 3-I | $2\text{-}CH_3\text{-}4\text{-}i\text{-}C_3F_7$ | 160–162 |
| 184 | $C(CH_3)_2CH_2SOC_2H_5$ | 3-I | $2\text{-}CH_3\text{-}4\text{-}i\text{-}C_3F_7$ | 78–82 |
| 185 | $C(CH_3)_2CH_2SC_2H_5$ | 3-Cl | $2\text{-}CH_3\text{-}4\text{-}i\text{-}C_3F_7$ | 132–134 |
| 186 | $C(CH_3)_2CH_2SO_2C_2H_5$ | 3-Cl | $2\text{-}CH_3\text{-}4\text{-}i\text{-}C_3F_7$ | 68 |
| 187 | $C(CH_3)_2CH_2SC_2H_5$ | 3-Br | $2\text{-}CH_3\text{-}4\text{-}i\text{-}C_3F_7$ | 169–170 |
| 188 | $CH(CH_3)CH_2S(CH_2)_2SCH_3$ | 3-I | $2\text{-}CH_3\text{-}4\text{-}i\text{-}C_3F_7$ | 169–171 |
| 189 | $CH(CH_3)CH_2S(CH_2)_2SCH_3$ | 3-I | $2\text{-}CH_3\text{-}4\text{-}C_2F_5$ | 135–137 |
| 190 | $CH(CH_3)CH_2S(CH_2)_2SCH_3$ | 3-I | $2\text{-}CH_3\text{-}4\text{-}OCF_3$ | 159–161 |
| 191 | $CH(CH_3)CH_2SCH_3$ | $3\text{-}SO_2\text{—}CH_3$ | $2\text{-}CH_3\text{-}4\text{-}i\text{-}C_3F_7$ | 205–206 |

TABLE 1-continued ($R^2=R^3=H$)

| No | $T^1$ | $(X)l$ | $(Y)m$ | Property mp (° C.) |
|---|---|---|---|---|
| 192 | $CH(CH_3)CH_2SCH_3$ | 6-$SO_2$—$CH_3$ | 2-$CH_3$-4-i-$C_3F_7$ | 210–212 |
| 193 | $CH(CH_3)CH_2SOCH_3$ | 3,4—$Cl_2$ | 2-$CH_3$-4-$OCF_3$ | 198–201 |
| 194 | $CH(CH_3)CH_2SO_2CH_3$ | 3,4—$Cl_2$ | 2-$CH_3$-4-$OCF_3$ | 165–167 |
| 195 | $CH(CH_3)(CH_2)_2SOCH_3$ | 3-I | 2-$CH_3$-4-i-$C_3F_7$ | 123–125 |
| 196 | $CH(CH_3)(CH_2)_2SO_2CH_3$ | 3-I | 2-$CH_3$-4-i-$C_3F_7$ | 128–130 |
| 197 | $CH(CH_3)(CH_2)_4SO_2CH_3$ | 3-I | 2-$CH_3$-4-$C_2F_5$ | 145 |
| 198 | $CH(CH_3)(CH_2)_4SO_2CH_3$ | 3-I | 2-$CH_3$-4-i-$C_3F_7$ | 160 |
| 199 | $CH(CH_3)(CH_2)_3SC_2H_5$ | 3-I | 2-$CH_3$-4-$C_2F_5$ | 143 |
| 200 | $CH(CH_3)(CH_2)_3SO_2C_2H_5$ | 3-I | 2-$CH_3$-4-$C_2F_5$ | 117 |
| 201 | $CH(CH_3)(CH_2)_3SC_2H_5$ | 3-I | 2-$CH_3$-4-i-$C_3F_7$ | 150 |
| 202 | $CH(CH_3)(CH_2)_3SOC_2H_5$ | 3-I | 2-$CH_3$-4-i-$C_3F_7$ | 106 |
| 203 | $CH(CH_3)(CH_2)_3SO_2C_2H_5$ | 3-I | 2-$CH_3$-4-i-$C_3F_7$ | 117 |
| 204 | $Q^1$ | 3-I | 2-$CH_3$-4-i-$C_3F_7$ | 202 |
| 205 | $Q^2$ | 3-I | 2-$CH_3$-4-i-$C_3F_7$ | 249 |
| 206 | $CH(CH_3)CH_2SCH_2CH=CH_2$ | 3-I | 2-$CH_3$-4-i-$C_3F_7$ | 168–175 |
| 207 | $CH_2CH(CH_3)SC_2H_5$ | 3-I | 2-$CH_3$-4-i-$C_3F_7$ | 150 |
| 208 | $CH_2CH(CH_3)SO_2C_2H_5$ | 3-I | 2-$CH_3$-4-i-$C_3F_7$ | 130 |
| 209 | $CH_2CH(CH_3)SC_2H_5$ | 6-1 | 2-$CH_3$-4-i-$C_3F_7$ | 155 |
| 210 | $CH(CH_3)CH_2SCH_3$ | 3-$OCF_3$ | 2-$CH_3$-4-i-$C_3F_7$ | 184–185 |
| 211 | $CH(CH_3)(CH_2)_2SOCH_3$ | 3-Cl | 2-$CH_3$-4-i-$C_3F_7$ | Amorphous |
| 212 | $CH(CH_3)(CH_2)_2SO_2CH_3$ | 3-Cl | 2-$CH_3$-4-i-$C_3F_7$ | 108–111 |
| 213 | $CH(CH_3)(CH_2)_3SC_2H_5$ | 3-Br | 2-$CH_3$-4-i-$C_3F_7$ | 151 |
| 214 | $CH(CH_3)(CH_2)_3SOC_2H_5$ | 3-Br | 2-$CH_3$-4-i-$C_3F_7$ | 159 |
| 215 | $CH(CH_3)(CH_2)_3SO_2C_2H_5$ | 3-Br | 2-$CH_3$-4-i-$C_3F_7$ | 150 |
| 216 | (S)—C* $H(CH_3)CH_2SCH_3$ | 3-I | 2-$CH_3$-4-i-$C_3F_7$ | 212–214 |
| 217 | (R)-C* $H(CH_3)CH_2SCH_3$ | 3-I | 2-$CH_3$-4-i-$C_3F_7$ | 214–216 |
| 218 | $C(CH_3)_2CH_2SOC_2H_5$ | 3-Br | 2-$CH_3$-4-i-$C_3F_7$ | 107–110 |
| 219 | $C(CH_3)_2CH_2S$-n-$C_3H_7$ | 3-I | 2-$CH_3$-4-i-$C_3F_7$ | 169–170 |
| 220 | $C(CH_3)_2CH_2SO$-n-$C_3H_7$ | 3-I | 2-$CH_3$-4-i-$C_3F_7$ | 88–90 |
| 221 | $C(CH_3)_2CH_2SO_2$-n-$C_3H_7$ | 3-I | 2-$CH_3$-4-i-$C_3F_7$ | 88–90 |
| 222 | $CH(CH_3)CH_2SCH_3$ | 3-Cl-4—$OCH_3$ | 2-$CH_3$-4-i-$C_3F_7$ | 122–125 |
| 223 | $CH(CH_3)CH_2SCH_3$ | 3-$NO_2$ | 2-$CH_3$-4—$OCF_2CHFCF_3$ | 218 |
| 224 | $CH(CH_3)CH_2SCH_3$ | 3-$NO_2$ | 2-$CH_3$-4-O-(3-Cl-5-$CF_3$-2-Pyi | 188 |
| 225 | $C(CH_3)_2CH_2SCH_3$ | 3-I | 2-Cl-4-$OCF_3$ | 166 |
| 226 | $C(CH_3)_2CH_2SO_2CH_3$ | 3-I | 2-Cl-4-$OCF_3$ | 141 |
| 227 | $C(CH_3)_2CH_2SCH_3$ | 3-Br | 2-Cl-4-$OCF_3$ | 160 |
| 228 | $C(CH_3)_2CH_2SO_2CH_3$ | 3-Br | 2-Cl-4-$OCF_3$ | 133 |
| 229 | $C(CH_3)_2(CH_2)_3SCH_3$ | 3-I | 2-$CH_3$-4-i-$C_3F_7$ | 164 |
| 230 | $C(CH_3)_2(CH_2)_2SCH_3$ | 3-I | 2-$CH_3$-4-i-$C_3F_7$ | 108 |
| 231 | $C(CH_3)_2(CH_2)_2CH(CH_3)$—$SCH_3$ | 3-I | 2-$CH_3$-4-i-$C_3F_7$ | 151 |
| 232 | $C(CH_3)_2CH_2SOCH_3$ | 3-Br | 2-Cl-4-$OCF_3$ | 132 |
| 233 | $CH(CH_3)CH_2SCH_3$ | 3-I | 2-Cl-4-$OCF_3$ | 172 |
| 234 | $CH(CH_3)CH_2SO_2CH_3$ | 3-I | 2-Cl-4-$OCF_3$ | 168 |
| 235 | $C(CH_3)_2CH_2SC_3H_7$-n | 3-Br | 2-$CH_3$-4-i-$C_3F_7$ | 162–163 |
| 236 | $C(CH_3)_2CH_2SC_3H_7$-n | 3-Cl | 2-$CH_3$-4-i-$C_3F_7$ | 149–150 |
| 237 | $C(CH_3)_2CH_2SO_2C_3H_7$-n | 3-Br | 2-$CH_3$-4-i-$C_3F_7$ | 176–180 |
| 238 | $C(CH_3)_2CH_2SO_2C_3H_7$-n | 3-Cl | 2-$CH_3$-4-i-$C_3F_7$ | 202–203 |
| 239 | $CH_2CH(CH_3)SCH_3$ | 3-I | 2-$CH_3$-4-i-$C_3F_7$ | 200 |
| 240 | $CH_2CH(CH_3)SO_2CH_3$ | 3-I | 2-$CH_3$-4-i-$C_3F_7$ | 130 |
| 241 | $CH(CH_3)CH_2SO_2CH_3$ | 3-$OCF_3$ | 2-$CH_3$-4-i-$C_3F_7$ | 226–228 |
| 242 | $C(CH_3)_2CH_2SC_2H_5$ | 3-I | 2-Cl-4-$OCF_3$ | 163 |
| 243 | $CH(CH_3)CH_2SOCH_3$ | 3,4-$Cl_2$ | 2-$CH_3$-4-i-$C_3F_7$ | 138–139 |
| 244 | $CH(CH_3)CH_2SO_2CH_3$ | 3 4-$Cl_2$ | 2-$CH_3$-4-i-$C_3F_7$ | 146–148 |
| 245 | $CH(CH_3)CH_2SCH_3$ | 3-$CF_3$ | 2-$CH_3$-4-i-$C_3F_7$ | 209 |
| 246 | $CH(CH_3)CH_2SOCH_3$ | 3-Cl | 2-$CH_3$-4-i-$C_3F_7$ | 110–112 |
| 247 | $C(CH_3)_2CH_2SC_2H_5$ | 3-I | 2-$CH_3$-4-$C_2F_5$ | 188–189 |
| 248 | $C(CH_3)_2CH_2SO_2C_2H_5$ | 3-I | 2-$CH_3$-4-$C_2F_5$ | 120–122 |
| 249 | $C(CH_3)_2CH_2SOC_2H_5$ | 3-I | 2-$CH_3$-4-$C_2F_5$ | 125–126 |
| 250 | $C(CH_3)_2CH_2SO_2C_2H_5$ | 3-I | 2-$CH_3$-4-$OCF_3$ | 125(Rf = great) |
| 251 | $C(CH_3)_2CH_2SO_2C_2H_5$ | 3-I | 2-$CH_3$-4-$OCF_3$ | 146(Rf = small) |
| 252 | $C(CH_3)_2CH_2SCH_3$ | 3-$OCH_2O$-4 | 2-$CH_3$-4-$OCF_3$ | 220 |
| 253 | $CH(CH_3)CH_2SOCH_3$ | 3-$OCF_3$ | 2-$CH_3$-4-i-$C_3F_7$ | 220 |
| 254 | $CH(CH_3)CH_2SOCH_3$ | 3-$CF_3$ | 2-$CH_3$-4-i-$C_3F_7$ | 223 |
| 255 | $CH(CH_3)CH_2SO_2CH_3$ | 3-$CF_3$ | 2-$CH_3$-4-i-$C_3F_7$ | 199–201 |
| 256 | $CH(CH_3)(CH_2)_2SC_2H_5$ | 3-Cl | 2-$CH_3$-4-i-$C_3F_7$ | 110–113 |
| 257 | $CH(CH_3)(CH_2)_2SC_2H_5$ | 3-I | 2-$CH_3$-4-i-$C_3F_7$ | 173–174 |
| 258 | $Q^5$ | 3-I | 2-$CH_3$-4-$OCF_3$ | 183 |

TABLE 1-continued ($R^2=R^3=H$)

| No | $T^1$ | (X)l | (Y)m | Property mp (° C.) |
|---|---|---|---|---|
| 259 | $Q^6$ | 3-I | 2-$CH_3$-4-i-$C_3F_7$ | 149 |
| 260 | $CH(CH_3)CH_2SOC_2H_5$ | 3-I | 2-$CH_3$-4-i-$C_3F_7$ | 96 |
| 261 | $CH(CH_3)CH_2SO_2C_2H_5$ | 3-I | 2-$CH_3$-4-i-$C_3F_7$ | 98 |
| 262 | $CH(CH_3)CH_2SC_2H_5$ | 3-Br | 2-$CH_3$-4-i-$C_3F_7$ | 155 |
| 263 | $CH(CH_3)CH_2SOC_2H_5$ | 3-Br | 2-$CH_3$-4-i-$C_3F_7$ | 96 |
| 264 | $CH(CH_3)CH_2SO_2C_2H_5$ | 3-Br | 2-$CH_3$-4-i-$C_3F_7$ | 135 |
| 265 | $CH(CH_3)CH_2SC_2H_5$ | 3-Cl | 2-$CH_3$-4-i-$C_3F_7$ | 145 |
| 266 | $CH(CH_3)CH_2SOC_2H_5$ | 3-Cl | 2-$CH_3$-4-i-$C_3F_7$ | 92 |
| 267 | $CH(CH_3)CH_2SO_2C_2H_5$ | 3-Cl | 2-$CH_3$-4-i-$C_3F_7$ | 135 |
| 268 | $CH(CH_3)CH_2SCH_3$ | 3-Br | 2-$CH_3$-4-$CF_3$ | 170–172 |
| 269 | $CH(CH_3)(CH_2)_2SOC_2H_5$ | 3-I | 2-$CH_3$-4-i-$C_3F_7$ | 132–134 |
| 270 | $CH(CH_3)(CH_2)_2SO_2C_2H_5$ | 3-I | 2-$CH_3$-4-i-$C_3F_7$ | 108–110 |
| 271 | $CH(CH_3)CH_2SC_3H_7$-n | 3-Cl | 2-$CH_3$-4-i-$C_3F_7$ | 174 |
| 272 | $C(CH_3)_2(CH_2)_2SC_2H_5$ | 3-I | 2-$CH_3$-4-i-$C_3F_7$ | 171 |
| 273 | $Q^7$ | 3-I | 2-$CH_3$-4-i-$C_3F_7$ | 184 |
| 274 | $CH(CH_3)(CH_2)_2SOC_2H_5$ | 3-Cl | 2-$CH_3$-4-i-$C_3F_7$ | 128–130 |
| 275 | $CH(CH_3)(CH_2)_2SO_2C_2H_5$ | 3-Cl | 2-$CH_3$-4-i-$C_3F_7$ | 105–106 |
| 276 | $CH(CH_3)CH_2SCH_3$ | 3-Cl | 2-$CH_3$-4-$CF_3$ | 158–160 |
| 277 | $CH(CH_3)CH_2SO_2CH_3$ | 3-Br | 2-$CH_3$-4-$CF_3$ | 118–120 |
| 278 | $C(CH_3)_2CH_2SCH_3$ | 3-$OCF_2$O-4 | 2-$CH_3$-4-i-$C_3F_7$ | 182 |
| 279 | $CH(CH_3)CH_2S$-Pyi | 3-I | 2-$CH_3$-4-i-$C_3F_7$ | 126 |
| 280 | $C(CH_3)_2(CH_2)_3SC_2H_5$ | 3-I | 2-$CH_3$-4-$OCF_3$ | 170 |
| 281 | $C(CH_3)_2(CH_2)_3SCH_3$ | 3-Br,6-Br | 2-$CH_3$-4-i-$C_3F_7$ | 111 Mixture |
| 282 | $C(CH_3)_2(CH_2)_3SC_2H_5$ | 3-Br,6-Br | 2-$CH_3$-4-i-$C_3F_7$ | 121 Mixture |
| 283 | $CH(CH_3)CH_2SO_2CH_3$ | 3-Cl | 2-$CH_3$-4-$CF_3$ | 179–181 |
| 284 | $CH(CH_3)CH_2SO_2CH_3$ | 3-I | 2-$CH_3$-4-$CF_3$ | 196–198 |
| 285 | $CH(CH_3)CH_2SCH_2CF_3$ | 3-I | 2-$CH_3$-4-i-$C_3F_7$ | 216 |
| 286 | $CH(CH_3)CH_2S(CH_2)_2$—$OCOCF_3$ | 3-I | 2-$CH_3$-4-i-$C_3F_7$ | 158–159 |
| 287 | $CH(CH_3)CH_2S$—$C_3H_7$-n | 3-Br | 2-$CH_3$-4-i-$C_3F_7$ | 111 |
| 288 | $CH(CH_3)CH_2SCH_3$ | 3-$OCF_2$O-4 | 2-$CH_3$-4-i-$C_3F_7$ | 196 |
| 289 | $CH(CH_3)CH_2SO_2CH_3$ | 3-$OCF_2$O-4 | 2-$CH_3$-4-i-$C_3F_7$ | 223 |
| 290 | $CH(CH_3)CH_2SCH_3$ | 3-$OCF_2$O-4 | 2-$CH_3$-4-$OCF_3$ | 191 |
| 291 | $CH(CH_3)CH_2SOCH_3$ | 3-$OCF_2$O-4 | 2-$CH_3$-4-$OCF_3$ | 187 |
| 292 | $C(CH_3)_2CH_2SCH_3$ | 3-$OCF_2$O-4 | 2-$CH_3$-4-$OCF_3$ | 205 |
| 293 | $C(CH_3)_2CH_2SO_2CH_3$ | 3-$OCF_2$O-4 | 2-$CH_3$-4-$OCF_3$ | 218 |
| 294 | $CH(CH_3)CH_2SOCH_2CF_3$ | 3-I | 2-$CH_3$-4-i-$C_3F_7$ | 207–209 |
| 295 | $CH(CH_3)CH_2SO_2CH_2CF_3$ | 3-I | 2-$CH_3$-4-i-$C_3F_7$ | 220–222 |
| 296 | $CH(CH_3)CH_2S(CH_2)_2OH$ | 3-I | 2-$CH_3$-4-i-$C_3F_7$ | 157–159 |
| 297 | $CH(CH_3)CH_2S(CH_2)_2$—$OC_2H_5$ | 3-I | 2-$CH_3$-4-i-$C_3F_7$ | 165–167 |
| 298 | .$CH_2SCH_3$ | H | 2-$CH_3$-4-i-$C_3F_7$ | 157–159 |
| 299 | $CH(CH_3)CH_2S$-2-(3,5—$(CH_3)_2$-Pym) | 3-I | 2-$CH_3$-4-i-$C_3F_7$ | 147–149 |
| 300 | $CH(CH_3)CH_2SO$-2-(3,5—$(CH_3)_2$-Pym) | 3-I | 2-$CH_3$-4-i-$C_3F_7$ | 126–128 |
| 301 | $CH(CH_3)CH_2SO_2$-2-(3,5—$(CH_3)_2$-Pym) | 3-I | 2-$CH_3$-4-i-$C_3F_7$ | 134–136 |
| 302 | $CH(CH_3)CH_2SC(=S)$—$N(CH_3)_2$ | 3-I | 2-$CH_3$-4-i-$C_3F_7$ | Paste |
| 303 | $CH(CH_3)CH_2SCH_3$ | 3-I | 2-$CH_3$-3-$C_2F_5$ | 223–225 |
| 304 | $CH(CH_3)CH_2SCH_3$ | 3-I | 2-$CH_3$-5-$C_2F_5$ | 215–218 |
| 305 | $CH(CH_3)CH_2SCH_3$ | 3-Cl | 2-$CH_3$-4-$CF_3$ | 179–181 |
| 306 | $CH(CH_3)CH_2SCH_3$ | 3-Br | 2-$CH_3$-4-$CF_3$ | 176–177 |
| 307 | $CH(CH_3)CH_2SCH_3$ | 3-I | 2-$CH_3$-4-$CF_3$ | 184–186 |
| 308 | $CH(CH_3)CH_2SCH_3$ | 3-N=C(t-$C_4H_9$)O-4 | 2-$CH_3$-4-i-$C_3F_7$ | 113 |
| 309 | $CH(CH_3)CH_2SC_2H_5$ | 3-I | 2-$CH_3$-4-$CF_3$ | 193–194 |
| 310 | $C(CH_3)_2CH_2SO_2CH_3$ | 3-Cl | 2-$CH_3$-4-$CF_3$ | 174–175 |
| 311 | $C(CH_3)_2CH_2SOCH_3$ | 3-Br | 2-$CH_3$-4-$CF_3$ | 85–88 |
| 312 | $C(CH_3)_2CH_2SO_2CH_3$ | 3-Br | 2-$CH_3$-4-$CF_3$ | 151–153 |
| 313 | $C(CH_3)_2CH_2SOCH_3$ | 3-I | 2-$CH_3$-4-$CF_3$ | 102–104 |
| 314 | $C(CH_3)_2CH_2SO_2CH_3$ | 3-I | 2-$CH_3$-4-$CF_3$ | 153–155 |
| 315 | $CH(CH_3)CH_2S(CH_2)_2$—$OCH_3$ | 3-I | 2-$CH_3$-4-i-$C_3F_7$ | 154–155 |
| 316 | $CH(CH_3)CH_2S(CH_2)_2$—$CO_2CH_3$ | 3-I | 2-$CH_3$-4-i-$C_3F_7$ | 160–162 |
| 317 | $CH(CH_3)CH_2SO(CH_2)_2$—$OC_2H_5$ | 3-I | 2-$CH_3$-4-i-$C_3F_7$ | 116–118 |
| 318 | $CH(CH_3)CH_2SO_2(CH_2)_2$—$OC_2H_5$ | 3-I | 2-$CH_3$-4-i-$C_3F_7$ | 138–140 |
| 319 | $CH(CH_3)CH_2S$-Bzt | 3-I | 2-$CH_3$-4-i-$C_3F_7$ | 179–181 |

TABLE 1-continued ($R^2=R^3=H$)

| No | $T^1$ | $(X)1$ | $(Y)m$ | Property mp (° C.) |
|---|---|---|---|---|
| 320 | $C(CH_3)_2CH_2SO_2CH_3$ | 3-Br | $2-CH_3-4-OCF_3$ | Crystal |
| 321 | $C(CH_3)_2CH_2SCH_3$ | 3-Br | $2-CH_3-4-OCF_3$ | 178 |
| 322 | $C(CH_3)_2CH_2SCH_3$ | $3-NO_2$ | $2-CH_3-4-OCF_3$ | 189 |
| 323 | $C(CH_3)_2CH_2SCH_3$ | $3-NO_2$ | $2-Cl-4-CH_3$ | 204 |
| 324 | $C(CH_3)_2CH_2SCH_3$ | $3-NO_2$ | $2-CH_3-4-Br$ | 208 |
| 325 | $C(CH_3)_2CH_2SCH_3$ | $3-NO_2$ | $2-CH_3-4-i-C_3F_7$ | 234 |
| 326 | $C(CH_3)_2CH_2SCH_3$ | $3-NO_2$ | $2,4-Cl_2$ | 178 |
| 327 | $C(CH_3)_2CH_2SOCH_3$ | $3-NO_2$ | $2-CH_3-4-i-C_3F_7$ | 143 |
| 328 | $C(CH_3)_2CH_2SO_2CH_3$ | $3-NO_2$ | $2-CH_3-4-i-C_3F_7$ | 197 |
| 329 | $Q^8$ | 3-I | $2-CH_3-4-i-C_3F_7$ | 183 |
| 330 | $CH(CH_3)CH_2SOCH_3$ | 3-Br | $2-CH_3-4-i-C_3F_7$ | 118 |
| 331 | $(CH_2)_2SH$ | H | $2-CH_3-4-i-C_3F_7$ | 170 |
| 332 | $CH(CH_3)CH_2SCH_3$ | 4-CH=CH—CH=CH-5 | $2-CH_3-4-i-C_3F_7$ | 158 |
| 333 | $CH(CH_3)CH_2SCH_3$ | 3-CH=CH—CH=CH-4 | $2-CH_3-4-i-C_3F_7$ | 194 |
| 334 | $CH(CH_3)CH_2SOCH_3$ | 3-CH=CH—CH=CH-4 | $2-CH_3-4-i-C_3F_7$ | 115 |
| 335 | $CH(CH_3)CH_2SO_2CH_3$ | 3-CH=CH—CH=CH-4 | $2-CH_3-4-i-C_3F_7$ | 121 |
| 336 | $CH(CH_3)CH_2SCH_3$ | 3-CH=CH—CH=CH-4 | $2-CH_3-4-OCF_3$ | 186 |
| 337 | $CH(CH_3)CH_2SCH_3$ | 3-Br | $2-Cl-4-OCF_3$ | 155 |
| 338 | $CH(CH_3)CH_2SOCH_3$ | 3-Br | $2-Cl-4-OCF_3$ | 174 |
| 339 | $CH(CH_3)CH_2SO_2CH_3$ | 3-Br | $2-Cl-4-OCF_3$ | 164 |
| 340 | $CH(CH_3)CH_2SO(CH_2)_2—OCH_3$ | 3-I | $2-CH_3-4-i-C_3F_7$ | 90–93 |
| 341 | $CH(CH_3)CH_2SO_2(CH_2)_2—OCH_3$ | 3-I | $2-CH_3-4-i-C_3F_7$ | 177–178 |
| 342 | $CH(CH_3)CH_2SO(CH_2)_2—CO_2CH_3$ | 3-I | $2-CH_3-4-i-C_3F_7$ | 144–147 |
| 343 | $CH(CH_3)CH_2SO_2(CH_2)_2—CO_2CH_3$ | 3-I | $2-CH_3-4-i-C_3F_7$ | 201–202 |
| 344 | $CH(CH_3)CH_2SO-2-Bzt$ | 3-I | $2-CH_3-4-i-C_3F_7$ | 133–135 |
| 345 | $CH(CH_3)CH_2SO_2-2-Bzt$ | 3-I | $2-CH_3-4-i-C_3F_7$ | 147–149 |
| 346 | $CH(CH_3)CH_2SC_2H_5$ | $3-OCF_3$ | $2-CH_3-4-i-C_3F_7$ | 189–190 |
| 347 | $CH(CH_3)CH_2SC_2H_5$ | $5-OCF_3$ | $2-CH_3-4-i-C_3F_7$ | 190–192 |
| 348 | $CH(CH_3)CH_2SCH_3$ | $3-CF_3$ | $2-CH_3-4-i-C_3F_7$ | 220–221 |
| 349 | $CH(CH_3)CH_2SC_2H_5$ | $3-CF_3$ | $2-CH_3-4-i-C_3F_7$ | 200–202 |
| 350 | $(CH_2)_2SC(=S)NHC_2H_5$ | H | $2-CH_3-4-i-C_3F_7$ | 129 |
| 351 | $CH(CH_3)CH_2SCH_3$ | $3-OCF_2CF_2O-4$ | $2-CH_3-4-i-C_3F_7$ | 216 |
| 352 | $CH(CH_3)CH_2S-2-Thz$ | 3-I | $2-CH_3-4-i-C_3F_7$ | 180 |
| 353 | $CH(CH_3)CH_2S-2-(5-CH_3-1,3,4-Thd)$ | 3-I | $2-CH_3-4-i-C_3F_7$ | 122–124 |
| 354 | $CH(CH_3)CH_2S-2-(5-CH_3-1,3,4-Thd)$ | 6-I | $2-CH_3-4-i-C_3F_7$ | 148–150 |
| 355 | $C(CH_3)_2CH_2SCH_3$ | $3-OCF_3$ | $2-CH_3-4-i-C_3F_7$ | 208–209 |
| 356 | $C(CH_3)_2CH_2SCH_3$ | $5-OCF_3$ | $2-CH_3-4-i-C_3F_7$ | 225 |
| 357 | $CH(CH_3)CH_2SO_2C_2H_5$ | $3-OCF_3$ | $2-CH_3-4-i-C_3F_7$ | 219–220 |
| 358 | $C(CH_3)_2CH_2SO_2CH_3$ | $3-CF_3$ | $2-CH_3-4-i-C_3F_7$ | 159–161 |
| 359 | $CH(CH_3)CH_2SO_2C_2H_5$ | $3-CF_3$ | $2-CH_3-4-i-C_3F_7$ | 218–219 |
| 360 | $C(CH_3)_2CH_2SO_2CH_3$ | $3-OCF_3$ | $2-CH_3-4-i-C_3F_7$ | 168–170 |
| 361 | $CH(CH_3)CH_2SCH_2CO—N(C_2H_5)_2$ | 3-I | $2-CH_3-4-i-C_3F_7$ | 130–131 |
| 362 | $CH(CH_3)CH_2SOCH_2CO—N(C_2H_5)_2$ | 3-I | $2-CH_3-4-i-C_3F_7$ | 95–98 |
| 363 | $CH(CH_3)CH_2SO_2CH_2CO—N(C_2H_5)_2$ | 3-I | $2-CH_3-4-i-C_3F_7$ | 197–199 |
| 364 | $CH(CH_3)CH_2SO_2-2-Thz$ | 3-I | $2-CH_3-4-i-C_3F_7$ | 153–155 |
| 365 | $C(CH_3)_2CH_2SCH_3$ | 3-I | $2-CH_2OH-4-i-C_3F_7$ | 188–191 |
| 366 | $C(CH_3)_2CH_2SCH_3$ | 3-I | $2-CH_3-3-F-4-i-C_3F_7$ | 218–221 |
| 367 | $C(CH_3)_2CH_2SCH_3$ | 3-I | $2-CH_3-4-n-C_4F_9$ | 170–174 |
| 368 | $CH(CH_3)CH_2SCH_3$ | 3-I | $2-CH_3-4-Si(CH_3)_3$ | 203–207 |
| 369 | $C(CH_3)_2CH_2SCH_3$ | 3-Cl | $2-Cl-4-OCF_3$ | 154 |
| 370 | $C(CH_3)_2CH_2SOCH_3$ | 3-Cl | $2-Cl-4-OCF_3$ | 73 |
| 371 | $C(CH_3)_2CH_2SO_2CH_3$ | 3-Cl | $2-Cl-4-OCF_3$ | 149 |
| 372 | $CH(CH_3)CH_2SCH_3$ | $3-Cl-4-CH_3$ | $2-CH_3-4-i-C_3F_7$ | 189 |
| 373 | $C(CH_3)_2CH_2SCH_3$ | $3-NO_2$ | $2-CH_3-4-C_2F_5$ | 218 |
| 374 | $C(CH_3)_2CH_2SOCH_3$ | $3-NO_2$ | $2-CH_3-4-C_2F_5$ | 194 |
| 375 | $C(CH_3)_2CH_2SO_2CH_3$ | $3-NO_2$ | $2-CH_3-4-C_2F_5$ | 210 |

TABLE 1-continued ($R^2$=$R^3$=H)

| No | $T^1$ | $(X)_l$ | $(Y)_m$ | Property mp (° C.) |
|---|---|---|---|---|
| 376 | $C(CH_3)_2CH_2SCH_3$ | 3-$NO_2$ | 2-Cl-4-$OCF_3$ | 181 |
| 377 | $C(CH_3)_2CH_2SOCH_3$ | 3-$NO_2$ | 2-Cl-4-$OCF_3$ | 185 |
| 378 | $C(CH_3)_2CH_2SO_2CH_3$ | 3-$NO_2$ | 2-Cl-4-$OCF_3$ | 186 |
| 379 | $CH(CH_3)CH_2SO_2CH_3$ | 3-Cl-4-$CH_3$ | 2-$CH_3$-4-i-$C_3F_7$ | 158–159 |
| 380 | $CH(CH_3)CH_2SCH_3$ | 3-Cl | 2-Cl-4-$OCF_3$ | 164 |
| 381 | $CH(CH_3)CH_2SOCH_3$ | 3-Cl | 2-Cl-4-$OCF_3$ | 172 |
| 382 | $CH(CH_3)CH_2SO_2CH_3$ | 3-Cl | 2-Cl-4-$OCF_3$ | 153 |
| 383 | $CH(CH_3)CH_2SSCH_3$ | 3-Cl | 2-$CH_3$-4-i-$C_3F_7$ | 92 |
| 384 | $CH(CH_3)CH_2SS$-(2-$NO_2$—Ph) | 3-Cl | 2-$CH_3$-4-i-$C_3F_7$ | 91 |
| 385 | $C(CH_3)_2CH_2SCH_3$ | 3-F | 2-Cl-4-$OCF_3$ | 148 |
| 386 | $C(CH_3)_2CH_2SOCH_3$ | 3-F | 2-Cl-4-$OCF_3$ | 102 |
| 387 | $C(CH_3)_2CH_2SO_2CH_3$ | 3-F | 2-Cl-4-$OCF_3$ | 163 |
| 388 | $CH(CH_3)CH_2SOCH_3$ | 3-$NO_2$ | 2-$CH_3$-4-i-$C_3F_7$ | 218 |
| 389 | $CH(CH_3)CH_2SOCH_3$ | 3-$NO_2$ | 2-$CH_3$-4-$OCF_3$ | 218 |
| 390 | $CH(CH_3)CH_2SOCH_3$ | 3-$NO_2$ | 2-$CH_3$-4-$CF_3$ | 243 |
| 391 | $CH(CH_3)CH_2SOCH_3$ | 3-$NO_2$ | 2-$CH_3$-4-$C_2F_5$ | 210 |
| 392 | $CH(CH_3)CH_2SH$ | 3-I | 2-$CH_3$-4-i-$C_3F_7$ | 226 |
| 393 | $CH(CH_3)CH_2SCH_3$ | 3-I | 2-$CH_3$-4-$OCF_2$—$CHFOCF_3$ | 192–193 |
| 394 | $CH(CH_3)CH_2SOCH_3$ | 3-I | 2-$CH_3$-4-$OCF_2$—$CHFOCF_3$ | 206–208 |
| 395 | $CH(CH_3)CH_2SO_2CH_3$ | 3-I | 2-$CH_3$-4-$OCF_2$—$CHFOCF_3$ | 166–167 |
| 396 | $CH(CH_3)CH_2SCH_3$ | 3-I | 2-$CH_3$-4-$OCF_2$—$CHFOC_3F_7$-n | 175–176 |
| 397 | $CH(CH_3)CH_2SCH_3$ | 3-I | 2-$CH_3$-4-O-(3-Cl-5-$CF_3$-2-Pyi) | 195–197 |
| 398 | $C(CH_3)_2CH_2SCH_3$ | 3-I | 2-$CH_3$-4-O-(3-Cl-5-$CF_3$-2-Pyi) | 180–181 |
| 399 | $C(CH_3)_2CH_2SC_3H_7$-i | 3-I | 2-$CH_3$-4-i-$C_3F_7$ | 85–88 |
| 400 | $C(CH_3)_2CH_2SC_4H_9$-t | 3-I | 2-$CH_3$-4-i-$C_3F_7$ | 95–98 |
| 401 | $C(CH_3)_2CH_2SOC_4H_9$-t | 3-I | 2-$CH_3$-4-i-$C_3F_7$ | 100–104 |
| 402 | $C(CH_3)_2CH_2SOC_3H_7$-i | 3-I | 2-$CH_3$-4-i-$C_3F_7$ | 100–104 |
| 403 | $CH(CH_3)CH_2S$-2-Pyi | 3-Br | 2-$CH_3$-4-i-$C_3F_7$ | 93 |
| 404 | $CH(CH_3)CH_2SO$-2-Pyi | 3-Br | 2-$CH_3$-4-i-$C_3F_7$ | 137 |
| 405 | $CH(CH_3)CH_2SO_2$-2-Pyi | 3-Br | 2-$CH_3$-4-i-$C_3F_7$ | 96 |
| 406 | $C(CH_3)_2CH_2SOCH_3$ | 3-I | 2-$CH_3$-4-O-(3-Cl-5-$CF_3$-2-Pyi) | 105–108 |
| 407 | $C(CH_3)_2CH_2SO_2CH_3$ | 3-I | 2-$CH_3$-4-O-(3-Cl-5-$CF_3$-2-Pyi) | 135–136 |
| 408 | $CH(CH_3)CH_2SOCH_3$ | 3-I | 2-$CH_3$-4-$OCF_2$—$CHFOC_3F_7$-n | 179–181 |
| 409 | $CH(CH_3)CH_2SO_2CH_3$ | 3-I | 2-$CH_3$-4-$OCF_2$—$CHFOC_3F_7$-n | 196–198 |
| 410 | $CH(CH_3)CH_2SOCH_3$ | 3-I | 2-$CH_3$-4-O-(3-Cl-5-$CF_3$-2-Pyi) | 176–179 |
| 411 | $CH(CH_3)CH_2SO_2CH_3$ | 3-I | 2-$CH_3$-4-O-(3-Cl-5-$CF_3$-2-Pyi) | 199–201 |
| 412 | $C(CH_3)_2CH_2SOCH_3$ | 3-I | 2-$CH_3$-3-F-4-i-$C_3F_7$ | 120–125 |
| 413 | $C(CH_3)_2CH_2SO_2CH_3$ | 3-I | 2-$CH_3$-3-F-4-i-$C_3F_7$ | 206–210 |
| 414 | $CH(CH_3)CH_2SCH_3$ | 3-Br | 2-$C_2H_5$-4-i-$C_3F_7$ | 175 |
| 415 | $CH(CH_3)CH_2SCH_3$ | 3-Br | 2-Cl-4-$C_2F_5$ | 180 |
| 416 | $CH(CH_3)CH_2SCH_3$ | 3-Br | 3-I-$C_3H_7$ | 135 |
| 417 | $C(CH_3)_2CH_2SCH_3$ | 3-I | 2-$CH_3$-4-$OSO_2CF_3$ | 187 Decomposed |
| 418 | $C(CH_3)_2CH_2SCH_3$ | 6-I | 2-$CH_3$-4-$OSO_2CF_3$ | |
| 419 | $C(CH_3)_2CH_2SOCH_3$ | 3-I | 2-$CH_3$-4-$OSO_2CF_3$ | Amorphous |
| 420 | $C(CH_3)_2CH_2SCH_3$ | 3-I | 2-$CH_3$-4-$OCF_2$—$CHFOC_3F_7$-n | 170–172 |
| 421 | $C(CH_3)_2CH_2SOCH_3$ | 3-I | 2-$CH_3$-4-$OCF_2$—$CHFOC_3F_7$-n | 68–75 |
| 422 | $C(CH_3)_2CH_2SO_2CH_3$ | 3-I | 2-$CH_3$-4-$OCF_2$—$CHFOC_3F_7$-n | 170–172 |
| 423 | $C(CH_3)_2CH_2SC_3H_7$-i | 3-Br | 2-$CH_3$-4-$C_2F_5$ | 162–163 |
| 424 | $C(CH_3)_2CH_2SO_2C_3H_7$-i | 3-I | 2-$CH_3$-4-i-$C_3F_7$ | 70–75 |
| 425 | $CH(CH_3)CH_2SC(=S)NH$—$CH_3$ | 3-I | 2-$CH_3$-4-i-$C_3F_7$ | 142 |
| 426 | $CH(CH_3)CH_2SC(=S)NH$—$C_2H_5$ | 3-I | 2-$CH_3$-4-i-$C_3F_7$ | 123 |
| 427 | $CH(CH_3)CH_2SCONHC_2H_5$ | 3-I | 2-$CH_3$-4-i-$C_3F_7$ | 178 |
| 428 | $CH(CH_3)CH_2SCOCH_3$ | 3-I | 2-$CH_3$-4-i-$C_3F_7$ | 117 |
| 429 | $CH(CH_3)CH_2SCH_2C\equiv CH$ | 3-I | 2-$CH_3$-4-i-$C_3F_7$ | 111 |
| 430 | $CH(CH_3)CH_2SCH_2$ | 3-I | 2-$CH_3$-4-i-$C_3F_7$ | 140 |

TABLE 1-continued ($R^2=R^3=H$)

| No | $T^1$ | $(X)l$ | $(Y)m$ | Property mp (° C.) |
|---|---|---|---|---|
| | -(2,4-$Cl_2$-Ph) | | | |
| 431 | $C(CH_3)_2CH_2S^* OCH_3$ (−)isomer | 3-I | 2-$CH_3$-4-i-$C_3F_7$ | Amorphous $[\alpha] = -20.4$ |
| 432 | $C(CH_3)_2CH_2S^* OCH_3$ (+)isomer | 3-I | 2-$CH_3$-4-i-$C_3F_7$ | Amorphous $[\alpha] = 20.6$ |
| 433 | $C(CH_3)_2CH_2SCH_3$ | 3-I | 3-$CF_2OCF_2O$-4 | 205 |
| 434 | $C(CH_3)_2CH_2SCH_3$ | 3-I | 2-Cl-3-$CF_2OCF_2O$-4 | 173 |
| 435 | $C(CH_3)_2CH_2SCH_3$ | 3-I | 2-$C_2H_5$-4-i-$C_3F_7$ | 188 |
| 436 | $C(CH_3)_2CH_2SOCH_3$ | 3-I | 2-$C_2H_5$-4-i-$C_3F_7$ | 125 |
| 437 | $C(CH_3)_2CH_2SO_2CH_3$ | 3-I | 2-$C_2H_5$-4-i-$C_3F_7$ | 166–167 |
| 438 | $C(CH_3)_2CH_2S$—Ph | 3-I | 2-$CH_3$-4-i-$C_3F_7$ | 167–168 |
| 439 | $C(CH_3)_2CH_2SO$—Ph | 3-I | 2-$CH_3$-4-i-$C_3F_7$ | 107 |
| 440 | $C(CH_3)_2CH_2SO_2$—Ph | 3-I | 2-$CH_3$-4-i-$C_3F_7$ | 200 |
| 441 | $C(CH_3)_2CH_2S$-2-Pyi | 3-I | 2-$CH_3$-4-i-$C_3F_7$ | 120–122 |
| 442 | $C(CH_3)_2CH_2SO$-2-Pyi | 3-I | 2-$CH_3$-4-i-$C_3F_7$ | 90–95 |
| 443 | $C(CH_3)_2CH_2SO_2$-2-Pyi | 3-I | 2-$CH_3$-4-i-$C_3F_7$ | 138 |
| 444 | $C(CH_3)_2CH_2SO_2$-2-Pyi | 6-I | 2-$CH_3$-4-i-$C_3F_7$ | 219 |
| 445 | $Q^{10}$ | 3-I | 2-$CH_3$-4-i-$C_3F_7$ | 212–213 |
| 446 | $Q^{11}$ | 3-I | 2-$CH_3$-4-i-$C_3F_7$ | 193–213 |
| 447 | $Q^{12}$ | 3-I | 2-$CH_3$-4-i-$C_3F_7$ | 203–205 |
| 448 | $C(CH_3)_2CH_2SCH_3$ | 3-I | 2-Cl-4-i-$C_3F_7$ | 184 |
| 449 | $C(CH_3)_2CH_2SOCH_3$ | 3-I | 2-Cl-4-i-$C_3F_7$ | 102–105 |
| 450 | $C(CH_3)_2CH_2SO_2CH_3$ | 3-I | 2-Cl-4-i-$C_3F_7$ | 200–201 |
| 451 | $C(CH_3)_2CH_2SCH_2$-(4-Cl—Ph) | 3-I | 2-$CH_3$-4-i-$C_3F_7$ | 163–164 |
| 452 | $CH(CH_2OH)(CH_2)_2S$—$CH_3$ | 3-I | 2-$CH_3$-4-i-$C_3F_7$ | 102 |
| 453 | $C(CH_3)_2CH_2SCH_3$ | 3-I | 2-$CH_3$-4-(4-Cl—Ph) | 172 |
| 454 | $C(CH_3)_2CH_2SO_2CH_3$ | 3-I | 2-$CH_3$-4-(4-Cl—Ph) | 128 |
| 455 | $C(CH_3)_2CH_2SCH_3$ | 3-$NO_2$ | 2-$CH_3$-4-S(2-Cl—Ph) | 188 |
| 456 | $C(CH_3)_2CH_2SCH_3$ | 3-$NO_2$ | 2-$CH_3$-4-S(3-Cl—Ph) | 181 |
| 457 | $C(CH_3)_2CH_2SCH_3$ | 3-$NO_2$ | 2-$CH_3$-4-S(4-Cl—Ph) | 201 |
| 458 | $C(CH_3)_2CH_2SCH_3$ | 3-I | 2-$CH_3$-4-S(2-Cl—Ph) | 159 |
| 459 | $C(CH_3)_2CH_2SCH_3$ | 3-I | 2-$CH_3$-4-S(3-Cl—Ph) | 156 |
| 460 | $C(CH_3)_2CH_2SCH_3$ | 3-I | 2-$CH_3$-4-S(3-Cl—Ph) | 156 |
| 461 | $CH(CH_3)CH_2SCON$—$(CH_3)_2$ | 3-I | 2-$CH_3$-4-i-$C_3F_7$ | 117 |
| 462 | $CH(CH_3)CH_2SCON$—$(C_2H_5)_2$ | 3-I | 2-$CH_3$-4-i-$C_3F_7$ | 75 |
| 463 | $CH(CH_3)CH_2SCH_2CO$—$CH_3$ | 3-I | 2-$CH_3$-4-i-$C_3F_7$ | 86 |
| 464 | $C(CH_3)_2CH_2SCH_3$ | 3-I | 2-$CH(CH_3)CH_2CH$—$(CH_3)_2$-4-i-$C_3F_7$ | 178 |
| 465 | $C(CH_3)_2CH_2SOCH_3$ | 3-I | 2-$CH(CH_3)CH_2CH$—$(CH_3)_2$-4-i-$C_3F_7$ | 100–105 |
| 466 | $C(CH_3)_2CH_2SO_2CH_3$ | 3-I | 2-$CH(CH_3)CH_2CH$—$(CH_3)_2$-4-i-$C_3F_7$ | 157–158 |
| 467 | (S)-$C^* H(CH_3)CH_2S$—$C_2H_5$ | 3-I | 2-$CH_3$-4-i-$C_3F_7$ | 197 |
| 468 | $C(CH_3)_2CH_2SCH_3$ | 3-I | 2-$CH_3$-4-(CO-(4-$CH_3$—Ph)) | 138 |
| 469 | $C(CH_3)_2CH_2SCH_3$ | 3-I | 2-$CH_3$-4-(CO-(4-Cl—Ph)) | 171 |
| 470 | $C(CH_3)_2CH_2SCH_3$ | 3-I | 2-$CH_3$-4-(C(=$NOCH_3$)—(4-Cl—Ph)) | Paste |
| 471 | $C(CH_3)_2CH_2SCH_3$ | 3-I | 2-$CH_3$-4-$CH_2$(4-Cl—Ph) | 162 |
| 472 | $C(CH_3)_2CH_2SCH_3$ | 3-I | 2-$CH_3$-4-CH(OH)(4-Cl—Ph) | Paste |
| 473 | $C(CH_3)_2CH_2SCH_3$ | 3-I | 2-$CH_3$-4-O(4-Cl—Ph) | 179 |
| 474 | $C(CH_3)_2CH_2SCH_3$ | 3-I | 2-$CH_3$-4-O(3-Cl—Ph) | 170 |
| 475 | $C(CH_3)_2CH_2SCH_3$ | 3-I | 2-$CH_3$-4-O(3-CN—Ph) | 176 |
| 476 | $CH(CH_3)CH_2SCH_3$ | 3-O(3-$CF_3$—Ph) | 2-$CH_3$-4-i-$C_3F_7$ | 169–170 |
| 477 | $CH(CH_3)CH_2SCH_3$ | 6-O(3-$CF_3$—Ph) | 2-$CH_3$-4-i-$C_3F_7$ | 167–169 |

TABLE 1-continued ($R^2 = R^3 = H$)

| No | $T^1$ | $(X)l$ | $(Y)m$ | Property mp (° C.) |
|---|---|---|---|---|
| 478 | $C(CH_3)_2CH_2SCH_3$ | 3-I | $4-SO_2N(C_2H_5)_2$ | 207–208 |
| 479 | $C(CH_3)_2CH_2SCH_3$ | 3-I | $2-CH_3-4-(CONH(4-Cl-Ph))$ | 236 |
| 480 | $C(CH_3)_2CH_2SCH_3$ | 3-I | $2-CH_3-4-(CON(CH_3)-(4-Cl-Ph)$ | 149 |
| 481 | $C(CH_3)_2CH_2SCH_3$ | 3-I | $2-CH_3-4-C(CF_3)_2OCH_3$ | 195–196 |
| 482 | $C(CH_3)_2CH_2SOCH_3$ | 3-I | $2-CH_3-4-C(CF_3)_2OCH_3$ | 178–180 |
| 483 | $C(CH_3)_2CH_2SO_2CH_3$ | 3-I | $2-CH_3-4-C(CF_3)_2OCH_3$ | 205–206 |
| 484 | $C(CH_3)_2CH_2SCH_3$ | 3-I | $2-CH_3-4-C(CF_3)_2-OCH_2-Ph$ | 149–151 |
| 485 | $C(CH_3)_2CH_2SCH_3$ | H | $4-CF_3$ | 185–188 |
| 486 | $C(CH_3)_2CH_2SCH_3$ | 3-I | $2-CH_3-4-C(CF_3)_2OH$ | 143–145 |
| 487 | $C(CH_3)_2CH_2SCH_3$ | 3-I | $4-NHSO_2CF_3$ | 207–209 |
| 488 | $CH(CH_3)CH_2SOCH_3$ | H | $4-CF_3$ | 226–227 |
| 489 | $CH(CH_3)CH_2SO_2CH_3$ | H | $4-CF_3$ | 192–194 |
| 490 | $C(CH_3)_2CH_2SCH_3$ | 3-I | $2-CH_3-4-(C(=NOH)-(4-Cl-Ph))$ | 112 |
| 491 | $C(CH_3)_2CH_2SCH_3$ | 3-I | $2-CH_3-4-C(CF_3)_2S-CH_3$ | 163–164 |
| 492 | $C(CH_3)_2CH_2SOCH_3$ | 3-I | $2-CH_3-4-C(CF_3)_2O-CH_2Ph$ | 150–152 |
| 493 | $C(CH_3)_2CH_2SO_2CH_3$ | 3-I | $2-CH_3-4-C(CF_3)_2O-CH_2Ph$ | 125–126 |
| 494 | $C(CH_3)_2CH_2SCH_3$ | 3-I | $2-CH_3-4-(CON-(C_2H_5)_2)$ | 187 |
| 495 | $C(CH_3)_2CH_2SCH_3$ | 3-I | $2-CH_3-4-(CON-(CH_3)_2)$ | Amorphous |
| 496 | $C(CH_3)_2CH_2SCH_3$ | 3-I | $2-CH_3-4-(CF_3)_2O-C_2H_5$ | 185–186 |
| 497 | $C(CH_3)_2CH_2SCH_3$ | $3,4-Cl_2$ | $2-CH_3-4-i-C_3F_7$ | |
| 498 | $C(CH_3)_2CH_2SOCH_3$ | $3,4-Cl_2$ | $2-CH_3-4-i-C_3F_7$ | |
| 499 | $C(CH_3)_2CH_2SO_2CH_3$ | $3,4-Cl_2$ | $2-CH_3-4-i-C_3F_7$ | |
| 500 | $CH(CH_2OCH_3)CH_2S-CH_3$ | 3-I | $2-CH_3-4-i-C_3F_7$ | |
| 501 | $CH(CH_2OCH_3)CH_2-SOCH_3$ | 3-I | $2-CH_3-4-i-C_3F_7$ | |
| 502 | $CH(CH_2OCH_3)CH_2-SO_2CH_3$ | 3-I | $2-CH_3-4-i-C_3F_7$ | |
| 503 | $CH(CF_3)CH_2SCH_3$ | 3-I | $2-CH_3-4-i-C_3F_7$ | |
| 504 | $CH(CH_2SCH_3)CH_2-COOCH_3$ | 3-I | $2-CH_3-4-i-C_3F_7$ | |
| 505 | $CH(CH_2SCH_3)CH_2-CONHCH_3$ | 3-I | $2-CH_3-4-i-C_3F_7$ | |
| 506 | $CH(CH_2SCH_3)CH_2-CON(CH_3)_2$ | 3-I | $2-CH_3-4-i-C_3F_7$ | |
| 507 | $C(CH_3)_2CH_2S-C_3H_5-c$ | 3-I | $2-CH_3-4-i-C_3F_7$ | |
| 508 | $C(CH_3)_2CH_2SO-C_3H_5-c$ | 3-I | $2-CH_3-4-i-C_3F_7$ | |
| 509 | $C(CH_3)_2CH_2SO_2-C_3H_5-c$ | 3-I | $2-CH_3-4-i-C_3F_7$ | |
| 510 | $Q^{13}$ | 3-I | $2-CH_3-4-i-C_3F_7$ | |
| 511 | $Q^{16}$ | 3-I | $2-CH_3-4-i-C_3F_7$ | |
| 512 | $Q^{14}$ | 3-I | $2-CH_3-4-i-C_3F_7$ | |
| 513 | $Q^{15}$ | 3-I | $2-CH_3-4-i-C_3F_7$ | |
| 514 | $C(CH_3)_2CH_2SCH_3$ | 3-I | $2-CH_3-4-(4-CF_3-Ph)$ | |
| 515 | $C(CH_3)_2CH_2SOCH_3$ | 3-I | $2-CH_3-4-(4-CF_3-Ph)$ | |
| 516 | $C(CH_3)_2CH_2SO_2CH_3$ | 3-I | $2-CH_3-4-(4-CF_3-Ph)$ | |
| 517 | $C(CH_3)_2CH_2SCH_3$ | 3-I | $2-CH_3-4-OCF_2CF_3$ | |
| 518 | $C(CH_3)_2CH_2SOCH_3$ | 3-I | $2-CH_3-4-OCF_2CF_3$ | |
| 519 | $C(CH_3)_2CH_2SO_2CH_3$ | 3-I | $2-CH_3-4-OCF_2CF_3$ | |
| 520 | $C(CH_3)_2CH_2S(=O)-OCH_3$ | 3-I | $2-CH_3-4-i-C_3F_7$ | |
| 521 | $C(CH_3)_2CH_2SO_3CH_3$ | 3-I | $2-CH_3-4-i-C_3F_7$ | |
| 522 | $C(CH_3)_2CH_2SO_2-NHCH_3$ | 3-I | $2-CH_3-4-i-C_3F_7$ | |
| 523 | $C(CH_3)_2CH_2SO_2-NHC_2H_5$ | 3-I | $2-CH_3-4-i-C_3F_7$ | |
| 524 | $C(CH_3)_2CH_2SO_2-N(CH_3)_2$ | 3-I | $2-CH_3-4-i-C_3F_7$ | |
| 523 | $C(CH_3)_2CH_2SO_2-N(C_2H_5)_2$ | 3-I | $2-CH_3-4-i-C_3F_7$ | |

TABLE 2

($R^3$ = H)

| No | $T^1$ | R2 | (X)l | (Y)m | Property mp (° C.) |
|---|---|---|---|---|---|
| 2-1 | $(CH_2)_2SC_2H_5$ | n-$C_3H_7$ | H | 2-$CH_3$-4-i-$C_3F_7$ | Paste |
| 2-2 | $(CH_2)_2SCH_3$ | n-$C_3H_7$ | H | 2-$CH_3$-4-i-$C_3F_7$ | 122 |
| 2-3 | $(CH_2)_2SCH_3$ | n-$C_3H_7$ | 3-F | 2-$CH_3$-4-i-$C_3F_7$ | 124 |
| 2-4 | $(CH_2)_2SO_2CH_3$ | n-$C_3H_7$ | 3-F | 2-$CH_3$-4-i-$C_3F_7$ | 81 |
| 2-5 | $(CH_2)_2SCH_3$ | $C_2H_5$ | 3-F | 2-$CH_3$-4-i-$C_3F_7$ | 132–137 |
| 2-6 | $(CH_2)_3SCH_3$ | $C_2H_5$ | 3-F | 2-$CH_3$-4-i-$C_3F_7$ | 120–122 |
| 2-7 | $(CH_2)_2SCH_3$ | $CH_3$ | 3-F | 2-$CH_3$-4-i-$C_3F_7$ | 127–132 |
| 2-8 | $CH_2SCH_3$ | $C_2H_5$ | 3-Cl | 2-$CH_3$-4-i-$C_3F_7$ | 155–159 |
| 2-9 | $(CH_2)_2SOCH_3$ | $CH_3$ | 3-F | 2-$CH_3$-4-i-$C_3F_7$ | Paste |
| 2-10 | $(CH_2)_2SO_2CH_3$ | $CH_3$ | 3-F | 2-$CH_3$-4-i-$C_3F_7$ | 160–164 |
| 2-11 | $(CH_2)_2SOCH_3$ | $C_2H_5$ | 3-F | 2-$CH_3$-4-i-$C_3F_7$ | Paste |
| 2-12 | $(CH_2)_2SO_2CH_3$ | $C_2H_5$ | 3-F | 2-$CH_3$-4-i-$C_3F_7$ | Paste |
| 2-13 | $(CH_2)_3SOCH_3$ | $C_2H_5$ | 3-F | 2-$CH_3$-4-i-$C_3F_7$ | Paste |
| 2-14 | $(CH_2)_3SO_2CH_3$ | $C_2H_5$ | 3-F | 2-$CH_3$-4-i-$C_3F_7$ | 173 |
| 2-15 | $CH(CH_3)CH_2SCH_3$ | $C_2H_5$ | 3-F | 2-$CH_3$-4-i-$C_3F_7$ | 114 |
| 2-16 | $CH_2SCH_3$ | $C_2H_5$ | 3-Cl | 2-$CH_3$-4-OCF_3$ | Refr.Index nD1.5440 (21.0° C.) |
| 2-17 | $CH_2SCH_3$ | $C_2H_5$ | 3-Cl | 2-$CH_3$-4-$OC_2F_5$ | Refr.Index nD1.5365 (21.0° C.) |

General formula (1)

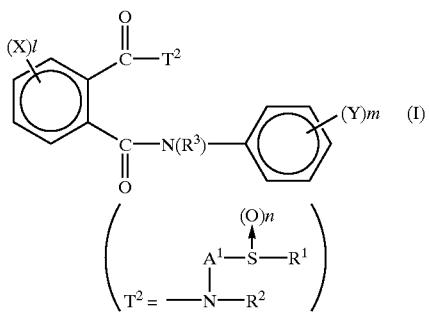

TABLE 3

($R^2$ = $R^3$ = H)

| No | $T^2$ | (X)l | (Y)m | Property mp (° C.) |
|---|---|---|---|---|
| 3-1 | $Q^3$ | 3-I | 2-$CH_3$-4-$C_2F_5$ | 163 |
| 3-2 | $Q^3$ | 3-I | 2-$CH_3$-4-i-$C_3F_7$ | 144 |
| 3-3 | $Q^4$ | 3-I | 2-$CH_3$-4-$OCF_3$ | 173–175 |
| 3-4 | $Q^4$ | 3-I | 2-$CH_3$-4-$C_2F_5$ | 158–160 |
| 3-5 | $Q^4$ | 3-I | 2-$CH_3$-4-i-$C_3F_7$ | 186–188 |
| 3-6 | $Q^9$ | 3-I | 2-$CH_3$-4-i-$C_3F_7$ | 195–197 |

In Tables 1 to 3, "Ph" means phenyl group; "Pyi" means pyridyl group; "Pym" means pyrimidyl group; "Thz" means thiazolyl group; "Thd" means thiadiazolyl group; "Bzt" means benzothiazolyl group; "c-" means an alicyclic hydrocarbon group; and $Q^1$, $Q^2$, $Q^3$, $Q^4$, $Q^5$, $Q^6$, Q7, $Q^8$, $Q^9$, $Q^{10}$, $Q^{11}$, $Q^{12}$, $Q^{13}$, $Q^{14}$, $Q^{15}$ and $Q^{16}$ represent the following compounds:

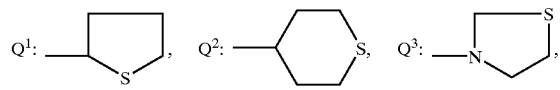

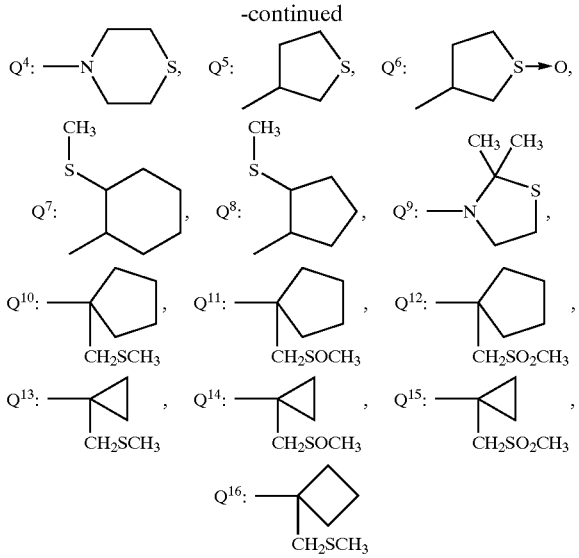

In Tables 1, 2 and 3, some compounds show a property of paste. The $^1$H-NMR data of such compounds are shown in Table 4.

TABLE 4

| No | $^1$H-NMR[CDCl$_3$/TMS, δ value (ppm)] |
|---|---|
| 2 | 0.8–1.4(m. 9H), 2.4(s. 3H), 2.5–2.8(m. 3H), 4.3(m. 1H), 6.2(d. 1H), 7.2–7.5(m. 3H), 7.8(d. 1H), 8.0(d. 1H), 8.4(d. 1H), 8.5(s. 1H). |

The agrohorticultural insecticides containing the phthalamide derivative of the general formula (I) or salt thereof of the present invention as an active ingredient are suitable for controlling various insect pests such as agricultural insect pests, forest insect pests, horticultural insect pests, stored grain insect pests, sanitary insect pests, nematodes, etc., which are injurious to paddy rice, fruit trees, vegetables, other crops, flowers and ornamental plants, etc. They have a marked insecticidal effect, for example, on LEPIDOPTERA including summer fruit tortrix (*Adoxophyes orana fasciata*), smaller tea tortrix (Adoxophyes sp.), Manchurian fruit moth (*Grapholita inopinata*), oriental fruit moth (*Grapholita molesta*), soybean pod border (*Leguminivora glycinivorella*), mulberry leafroller (*Olethreutes mori*), tea leafroller (*Caloptilia thevivora*), Caloptilia sp. (*Calopilia zachrysa*), apple leafminer (*Phyllonorycter ringoniella*), pear barkminer (*Spulerrina astaurota*), common white (*Piers rapae crucivora*), tabacco budworm (Heliothis sp.) codling moth (*Laspey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tabacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticeps*), brown rice planthopper (*Nilaparvata lugens*), whitebacked rice planthopper (*Sogatella furcifera*), citrus psylla (*Diaphorina citri*), grape whitefly (*Aleurolobus taonabae*), sweetpotato whitefly (*Bemisia tabaci*), greenhouse whitefly (*Trialeurodes*

*vaporariorum*), turnip aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), san Jose scale (*Comstockaspis perniciosa*), arrowhead scale (*Unaspis yanonensis*), etc.; TYLENCHIDA including root-lesion namatode (Pratylenchus sp.), soybean beetle (*Anomala rufocuprea*), Japanese beetle (*Popillia japonica*), tabacco beetle (*Lasioderma serricorne*), powderpost beetle (*Lyctus brunneus*), twenty-eight-spotted ladybird (*Epilachna vigintiotopunctata*), azuki bean weevile (*Callosobruchus chinensis*), vegetable weevile (*Listroderes costirostris*), maize weevile (*Sitophilus zeamais*), boll weevile (*Authonomus gradis gradis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (Diabrotica sp.), etc.; DIPTERA including melon fly (*Dacus(Zeugodacus) cucurbitae*), oriental fruit fly (*Dacus(Bactrocera) dorsalis*), rice leafminer (*Agnomyza oryzae*), onion maggot (*Delia antigua*), seedcorn maggot (*Delia platura*), soybean pod gall midge (Asphondylia sp.), muscid fly (*Musca domestica*), house mosquito (*Culex pipiens pipiens*), etc.; and TYLENCHIDA including coffer root-lesion nematode (*Pratylenchus coffeae*), potato cyst nematode (*Globodera rostochiensis*), root-knot nematode (Meloidogyne sp.), citrus nematode (*Tylenchulus semipenetrans*), Aphelenchus sp. (*Aphelenchus avenae*), chrysanthemum foliar (*Aphelenchoides ritzemabosi*), etc.

The agricultural and horticultural insecticide containing the phthalamide derivative of the general formula (I) or salt thereof of the present invention as an active ingredient has a marked insecticidal effect on the above-exemplified insect pests, sanitary insect pests, and/or nematodes, which are injurious to paddy field crops, upland crops, fruit trees, vegetables, other crops, flowers and ornament plants, and the like. Therefore, the desired effect of the agricultural and horticultural insecticide of the present invention can be obtained by applying the insecticide to paddy field; upland field; crops such as fruits, vegetables, ornament plants and the like; seeds, flowers, stalks, leaves, etc. of plants itself; environments of plant growth such as paddy field water, soil, etc. at a season at which the insect pests, sanitary pests or nematodes are expected to appear, before their appearance or at the time when their appearance is confirmed.

In general, the agricultural and horticultural insecticide of the present invention is used after being prepared into conveniently usable forms according to an ordinary manner for preparation of agrochemicals.

That is, the phthalamide derivative of the general formula (I) or salt thereof and, optionally, an adjuvant are blended with a suitable inert carrier in a proper proportion and prepared into a suitable preparation form such as a suspension, emulsifiable concentrate, soluble concentrate, wettable powder, granules, dust or tablets through dissolution, dispersion, suspension, mixing, impregnation, adsorption or sticking.

The inert carrier used in this invention may be either solid or liquid. As the solid carrier, there can be exemplified soybean flour, cereal flour, wood flour, bark flour, saw dust, powdered tobacco stalks, powdered walnut shells, bran, powdered cellulose, extraction residues of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon, i.e. synthetic, high-dispersion silicic acid, also called finely divided hydrated silica or hydrated silicic acid, some of commercially available products contain calcium silicate as the major component), activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea and ammonium chloride), and compost. These carriers may be used alone or as a mixture thereof.

The liquid carrier is that which itself has solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, Cellosolve, dipropyl ether and tetrahydrofuran; aliphatic hydrocarbons such as kerosene and mineral oils; aromatic hydrocarbons such as benzene, toluene, xylene, solvent naphtha and alkylnaphthalenes; halogenated hydrocarbons such as dichloroethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan mono-laurate, polyoxyethylene sorbitan monooleate, alkylarylsulfonates, naphthalenesulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates.

To improve the flowabililty of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicon oils may also be used as a defoaming agent.

The content of the active ingredient may be varied as required and may be chosen in a range of 0.01 to 80% by weight as an active ingredient. In dusts or granules, the suitable content thereof is from 0.01 to 50% by weight. In emulsifiable concentrates or flowable wettable powders, it is also from 0.01 to 50% by weight.

The agricultural and horticultural insecticide of the present invention is used to control a variety of insect pests in the following manner. That is, it is applied to a crop on which the insect pests are expected to appear or a site where the appearance of the insect pests is undesirable, as it is or after being properly diluted with or suspended inwater or the like, in an amount effective for control of the insect pests.

The applying dosage of the agricultural and horticultural insecticide of the present invention is varied depending upon various factors such as a purpose, insect pests to be controlled, a growth state of a plant, tendency of insect pests appearance, weather, environmental conditions, a preparation form, an application method, an application site and an application time. It may be properly chosen in a range of 0.1 g to 10 kg (in terms of the active ingredient) per 10 ares depending upon purposes.

The agricultural and horticultural insecticide of the present invention may be used in admixture with other agricultural and horticultural disease or pest controllers, acaricides, nematicides, bioagrochemicals, etc.; and herbicides, plant growth regulators, manures, etc. depending upon scenes using the present agricultural and horticultural insecticides, in order to expand both spectrum of controllable diseases and insect pest species and the period of time when effective applications are possible or to reduce the dosage.

The agrohorticultural insecticide of the present invention may be applied to the plant seeds or the cultivation mediums for seeding such as soil to be seeded, the mat for raising seedlings, water, etc. by the method of application to rice nursery box, seed powdering, etc. or by the method of seed disinfection. For controlling the pest insects generated on fruit trees, cereals, upland field for vegetables, etc., it is also possible to make a plant absorb the agrohorticultural agent of the present invention by a seed treatment such as powder coating, dipping, etc., irrigation into seedling-raising carrier such as seedling-raising vessel, planting hole, etc. or by treatment of the culture solution for water culture.

EXAMPLES

Next, typical examples of the present invention are presented below. The present invention is by no means limited by these examples.

Example 1

(1-1) Production of N-[4-(1,1,2,3,3,3-Hexafluoropropoxy)-1-methylphenyl]-3-nitrophthalimide In 30 ml of acetic acid were dissolved 1.93 g of 3-nitrophthalic anhydride and 2.73 g of 4-(1,1,2,3,3,3-hexafluoropropoxy)-1-methylaniline. A reaction was carried out for 3 hours with heating under reflux. After completion of the reaction, the solvent was distilled off under reduced pressure, and the residue was washed with a mixture of ether and hexane, whereby 4.4 g of the objective compound was obtained.

Property: m.p. 121° C.; Yield: 98%.

(1-2) Production of $N^1$-[4-(1,1,2,3,3,3-Hexafluoropropoxy)-1-methylphenyl]-$N^2$-(1-methyl-2-methylthioethyl)-3-nitrophthalamide (Compound No. 223)

In 10 ml of dioxane was dissolved 0.54 g of N-[4-(1,1,2,3,3,3-hexafluoropropoxy)-1-methylphenyl]-3-nitrophthalimide. Then, 0.25 g of 1-methyl-2-methylthioethylamine and 0.01 g of acetic acid were added to the solution obtained above, and a reaction was carried out for 3 hours with heating under reflux. After completion of the reaction, the solvent was distilled off under reduced pressure, and the residue was purified by column chromatography using 1/1 mixture of hexane and ethyl acetate as an eluent. Thus, 0.45 g of the objective compound having an Rf value of 0.4 to 0.5 was obtained.

Property: m.p. 218° C.; Yield: 68%.

Example 2

(2-1) Production of 3-Fluoro-N-(4-heptafluoroisopropyl-2-methylphenyl)phthalimide In 10 ml of acetic acid were dissolved 1.33 g of 3-fluorophthalic anhydride and 4-heptafluoroisopropyl-2-methylaniline. A reaction was carried out for 3 hours with heating under reflux. After completion of the reaction, the solvent was distilled off under reduced pressure, and the residue was washed with a mixture of ether and hexane to obtain 3.1 g of the objective compound.

Property: m.p. 155–157° C.; Yield: 97%.

(2-2) Production of N-(Heptafluoroisopropyl-2-methylphenyl)phthalimide

In 20 ml of dimethylformamide was dissolved 2.54 g of 3-fluoro-N-(4-heptafluoroisopropyl-2-methylphenyl)-phthalimide. After adding 2.8 g of a 15% aqueous solution of methylmercaptan to the solution obtained above, a reaction was carried out at room temperature for 3 hours with stirring. After completion of the reaction, the reaction solution was poured into water, and the objective product was extracted with ethyl acetate. The extract solution was dried on anhydrous magnesium, the solvent was distilled off under reduced pressure, and the residue was washed with a mixture of ether and hexane. Thus, 2.2 g of the objective compound was obtained.

Property: m.p. 163–165° C.; Yield: 81%.

(2-3) Production of N-(4-Heptafluoroisopropyl-2-methylphenyl)-3-methylsulfonylphthalimide In 20 ml of dichloromethane was dissolved 0.63 g of N-(4-heptafluoroisopropyl-2-methylphenyl)-3-methylthiophthalimide. While cooling the solution with ice, 0.58 g of m-chloroperbenzoic acid was added and reacted at room temperature. After completion of the reaction, the reaction solution was poured into water, and the objective product was extracted with chloroform. The organic layer was washed with an aqueous solution of sodium thiosulfate and an aqueous solution of potassium carbonate and dried on anhydrous magnesium, the solvent was distilled off under reduced pressure, and the residue was washed with a mixture of ether and hexane. Thus, 0.63 g of the objective compound was obtained.

Property: m.p. 185–187° C.; Yield: 93%.

(2-4) Production of $N^1$-(4-Heptafluoroisopropyl-2-methylphenyl)-$N^2$-(1-methyl-2-methylthioethyl)-3-methylsulfonylphthalamide (Compound No. 191) and $N^1$-(4-Heptafluoroisopropyl-2-methylphenyl)-$N^2$-(1-methyl-2-methylthioethyl)-6-methylsulfonylphthalamide (Compound No. 192)

In 10 ml of dioxane was dissolved 0.63 g of N-(4-heptafluoroisopropyl-2-methylphenyl)-3-methylsulfonyl-phthalimide. After adding 0.25 g of 1-methyl-2-methylthioethylamine and 0.01 g of acetic acid to the solution obtained above, a reaction was carried out for 3 hours with heating under reflux. After completion of the reaction, the solvent was distilled off under reduced pressure, and the residue was purified by silica gel column chromatography using 1/1 mixture of hexane and ethyl acetate as an eluent. Thus, 0.42 g of the first objective compound having an Rf value of 0.5 to 0.7 (Compound No. 191) and 0.18 g of the second objective compound having an Rf value of 0.2 to 0.3 (Compound No. 192) were obtained.

Compound No. 191: Property: m.p. 205–206° C.; Yield: 55%.

Compound No. 192: Property: m.p. 210–212° C.; Yield: 24%.

Example 3

(3-1) Production of 3-Iodo-N-(1-methyl-3-methylthiopropyl)-phthalamic Acid

To a suspension of 2.74 g of 3-iodophthalic anhydride in 8 ml of acetonitrile cooled with ice was slowly added dropwise a solution of 1.19 g of 1-methyl-3-methylthiopropylamine in 3 ml of acetonitrile. After completion of the dropping, a reaction was carried out at room temperature for 3 hours with stirring. After completion of the reaction, the deposited crystal was collected by filtration and washed with a small quantity of acetonitrile. Thus, 3.5 g of the objective compound was obtained.

Property: m.p. 148–150° C.; Yield: 89%.

(3-2) Production of 6-Iodo-N-(1-methyl-3-methylthiopropyl)-phthalisoimide

To a suspension of 0.79 g of 3-iodo-N-(1-methyl-3-methylthiopropyl)phthalamic acid in 10 ml of toluene was added 0.63 g of trifluoroacetic anhydride. A reaction was carried out at room temperature for 30 minutes with stirring. After completion of the reaction, the solvent was distilled off under reduced pressure to obtain 0.75 g of a crude objective product, which was used in the subsequent reaction without purification.

(3-3) Production of 6-Iodo-$N^1$-(4-heptafluoroisopropyl-2-methylphenyl)-$N^2$-(1-methyl-3-methylthiopropyl) phthalamide (Compound No. 162)

In 10 ml of acetonitrile was dissolved 0.75 g of 6-iodo-N-(1-methyl-3-methylthiopropyl)phthalisoimide. After adding 0.55 g of 4-heptafluoroisopropyl-2-methylaniline and 0.01 g of trifluoroacetic acid to the solution obtained above, a reaction was carried out for 3 hours with stirring. After completion of the reaction, the deposited crystal was collected by filtration and washed with a small quantity of cold acetonitrile. Thus, 1.17 g of the objective compound was obtained.

Property: m.p. 192–194° C.; Yield: 90%.

(3-4) Production of 3-Iodo-$N^1$-(4-heptafluoroisopropyl-2-methylphenyl)-$N^2$-(1-methyl-3-methylsulfenylpropyl)-phthalamide (Compound No. 195)

In 10 ml of dichloromethane was dissolved 0.65 g of 6-iodo-$N^1$-(4-heptafluoroisopropyl-2-methylphenyl)-$N^2$-(1-methyl-3-methylthiopropyl)phthalamide. After adding 0.18 g of m-chloroperbenzoic acid to the solution obtained above, a reaction was carried out at room temperature for 3 hours. After completion of the reaction, the reaction solution was poured into water, and the objective product was extracted with chloroform. The organic layer was washed with an aqueous solution of sodium thiosulfate and an aqueous solution of potassium carbonate and dried on anhydrous magnesium sulfate, the solvent was distilled off under reduced pressure, and the residue was washed with a mixture of ether and hexane. Thus, 0.61 g of the objective compound was obtained.

Property: m.p. 123–125° C.; Yield: 92%.

(3-5) Production of 3-Iodo-$N^1$-(4-heptafluoroisopropyl-2-methylphenyl)-$N^2$-(1-methyl-3-methylsulfonylpropyl)-phthalamide (Compound No. 196)

3-Iodo-$N^1$-(4-heptafluoroisopropyl-2-methylphenyl)-$N^2$-(1-methyl-3-methylsulfenylpropyl)phthalamide (0.4 g) was treated in the same manner as in Example (3-4). Thus, 0.39 g of the objective compound was obtained.

Property: m.p. 128–130° C.; Yield: 95%.

Example 4

(4-1) Production of N-(4-Heptafluoroisopropyl-2-methylphenyl)-3-trifluoromethoxybenzamide In 50 ml of tetrahydrofuran was dissolved 2.24 g of 3-trifluoromethoxybenzoyl chloride, to which were slowly added dropwise 2.75 g of 4-heptafluoroisopropyl-2-methylaniline and 1.2 g of triethylamine. After completion of the dropping, a reaction was carried out at room temperature for 1 hour. After completion of the reaction, the reaction solution was poured into water, the objective product was extracted with ethyl acetate and dried on anhydrous magnesium sulfate, the solvent was distilled off under reduced pressure, and the residue was washed with a mixture of ether and hexane. Thus, 4.6 g of the objective compound was obtained.

Property: Oily product; Yield: 99%.

(4-2) Production of N-(4-Heptafluoroisopropyl-2-methylphenyl)-3-trifluoromethoxyphthalamic Acid In 20 ml of tetrahydrofuran was dissolved 2.2 g of N-(4-heptafluoroisopropyl-2-methylphenyl)-3-trifluoromethoxybenzamide. At −70° C., 10 ml of s-butyllithium (0.96 M/L) was slowly added to the above solution and reacted at that temperature for 30 minutes. Then, the cooling bath was removed, and an excessive amount of carbon dioxide was introduced into the reaction solution and reacted at room temperature for 30 minutes. After completion of the reaction, the reaction solution was poured into water and acidified with dilute hydrochloric acid, the objective product was extracted with ethyl acetate and dried on anhydrous magnesium sulfate, the solvent was distilled off under reduced pressure, and the residue was washed with a mixture of ether and hexane. Thus, 2.1 g of the objective compound was obtained.

Property: m.p. 168–172° C.; Yield: 87%.

(4-3) Production of N-(4-Heptafluoroisopropyl-2-methylphenyl)-3-trifluoromethoxyphthalisoimide To a suspension of 0.46 g of N-(4-heptafluoroisopropyl-2-methylphenyl)-3-trifluoromethoxyphthalamic acid in 10 ml of toluene was added 0.51 g of trifluoroacetic anhydride, and a reaction was carried out at room temperature for 30 minutes. After completion of the reaction, the solvent was distilled off under reduced pressure to obtain 0.49 g of a crude objective product. The product thus obtained was used in the subsequent reaction without purification.

(4-4) Production of $N^1$-(4-Heptafluoroisopropyl-2-methylphenyl)-$N^2$-3-(1-methyl-2-methylthioethyl)-3-trifluoromethoxyphthalamide (Compound No. 210)

In 10 ml of acetonitrile was dissolved 0.44 g of N-(4-heptafluoroisopropyl-2-methylphenyl)-3-trifluoromethoxyphthalisoimide. Then, 0.10 g of 1-methyl-2-methylthioethylaniline and 0.01 g of trifluoroacetic acid were added to the solution obtained above, and reacted for 3 hours. After completion of the reaction, the reaction solution was cooled to 0° C., the deposited crystal was collected by filtration, and washed with hexane. Thus, 0.46 g of the objective compound was obtained.

Property: m.p. 184-185° C.; Yield: 77%.

Next, typical formulation examples of the present invention and test examples are presented below. The present invention is by no means limited by these examples.

In the formulation examples, the term "parts" means "parts by weight".

Formulation Example 1

| | |
|---|---|
| Each compound listed in Table 1, 2 or 3 | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound listed in Table 1, 2 or 3 | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound listed Table 1, 2 or 3 | 5 parts |
| Mixed powder of bentonite and clay | 90 parts |
| Calcium lignin sulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound listed in Table 1, 2 or 3 | 20 parts |
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Insecticidal Effect on Diamond Back Moth (*Plutella xylostella*)

Adult diamondback moths were released and allowed to oviposit on a Chinese cabbage seedling. Two days after the release, the seedling having the eggs deposited thereon was immersed for about 30 seconds in a liquid chemical prepared by diluting a preparation containing each compound listed in Table 1, 2 or 3 as an active ingredient to adjust the concentration to 50 ppm. After air-dryness, it was allowed to stand in a room thermostatted at 25° C. Six days after the immersion, the hatched insects were counted. The mortality was calculated according to the following equation and the insecticidal effect was judged according to the criterion shown below. The test was carried out with triplicate groups of 10 insects.

$$\text{Corrected mortality (\%)} = \frac{\begin{bmatrix}\text{Number of}\\\text{hatched insects in}\\\text{untreated group}\end{bmatrix} - \begin{bmatrix}\text{Number of}\\\text{hatched insects}\\\text{in treated group}\end{bmatrix}}{\begin{bmatrix}\text{Number of}\\\text{hatched insects in}\\\text{untreated group}\end{bmatrix}} \times 100$$

Criterion:

| Effect | Mortality (%) |
|---|---|
| A | 100 |
| B | 99–90 |
| C | 89–80 |
| D | 79–50 |

The results obtained are shown in Table 5.

Test Example 2

Insecticidal Effect on Common Cutworm (*Spodoptera Litura*)

A piece of cabbage leaf (cultivar; Shikidori) was immersed for about 30 seconds in a liquid chemical prepared by diluting a preparation containing each compound listed in Table 1, 2 or 3 as an active ingredient to adjust the concentration to 50 ppm. After air-dryness, it was placed in a plastic Petri dish with a diameter of 9 cm and inoculated with second-instar larvae of common cutworm, after which the dish was closed and then allowed to stand in a room thermostatted at 25° C. Eight days after the inoculation, the dead and alive were counted. The mortality was calculated according to the following equation and the insecticidal effect was judged according to the criterion shown in Test Example 1. The test was carried out with triplicate groups of 10 insects.

$$\text{Corrected mortality (\%)} = \frac{\begin{bmatrix}\text{Number of alive}\\\text{larvae in}\\\text{untreated group}\end{bmatrix} - \begin{bmatrix}\text{Number of alive}\\\text{larvae in}\\\text{treated group}\end{bmatrix}}{\begin{bmatrix}\text{Number of alive larvae}\\\text{in untreated group}\end{bmatrix}} \times 100$$

The results are shown in Table 5.

Test Example 3

Insecticidal Effect on Smaller tea Tortrix (Adoxophyes sp.)

A leaf of tea tree was immersed for 30 seconds in a liquid chemical containing each compound listed in Table 1, 2 or 3 as an active ingredient to adjust the concentration to 50 ppm. After air-dryness, the leaf was transferred to a plastic dish with a diameter of 9 cm and inoculated with larval smaller tea tortrix. Then, the leaf was allowed to stand in a room thermostatted at 25° C. at a humidity of 70%. Eight days after the inoculation, the dead and alive were counted, and the insecticidal effect was judged according to the same criterion as mentioned in Test Example 1. The test was carried out with triplicate groups of 10 insects.

The results are shown in Table 5.

TABLE 5

| No | Test Example 1 | Test Example 2 | Test Example 3 |
|---|---|---|---|
| 1 | A | A | A |
| 2 | A | A | A |
| 3 | A | A | A |
| 4 | A | | |
| 5 | A | A | |
| 6 | A | A | A |
| 7 | A | A | A |
| 8 | A | | C |
| 9 | A | | |
| 10 | A | A | A |
| 11 | A | A | A |
| 12 | A | | |
| 13 | A | | |
| 14 | A | | |
| 15 | A | | |
| 16 | A | | A |
| 17 | A | A | A |
| 18 | A | A | A |
| 19 | A | A | A |
| 20 | A | A | A |
| 21 | A | A | A |
| 22 | A | A | A |
| 23 | A | A | A |
| 24 | A | | A |
| 25 | A | A | A |
| 26 | A | A | A |
| 27 | A | | |
| 28 | A | A | A |
| 29 | A | A | A |
| 30 | A | A | A |
| 31 | A | A | A |
| 32 | A | A | A |
| 33 | A | A | A |
| 34 | A | A | A |
| 35 | A | A | A |
| 36 | A | | |
| 37 | A | A | A |
| 38 | A | | A |
| 39 | A | A | A |
| 41 | A | A | A |
| 42 | A | | |
| 43 | A | | A |
| 44 | A | | A |
| 46 | A | | A |
| 47 | A | | |
| 48 | A | A | A |
| 49 | A | A | A |
| 50 | A | A | A |
| 51 | A | | |
| 52 | A | | |
| 53 | A | | A |
| 54 | A | C | A |
| 55 | A | | |
| 56 | A | A | A |
| 57 | A | | A |
| 58 | A | | |
| 59 | A | | A |
| 60 | A | | A |
| 61 | A | A | A |
| 62 | A | A | A |
| 63 | A | | A |
| 64 | A | | A |
| 65 | A | A | A |
| 66 | A | A | A |
| 67 | A | A | A |
| 71 | A | | |
| 72 | A | | A |
| 73 | A | C | A |
| 74 | A | D | |
| 75 | A | A | A |
| 76 | A | A | A |
| 77 | A | | |
| 78 | A | | |
| 79 | A | A | A |
| 80 | A | A | A |
| 81 | A | A | A |
| 82 | A | | A |
| 83 | A | A | A |
| 84 | A | A | A |
| 85 | A | | A |
| 86 | A | A | A |
| 87 | A | C | |
| 88 | A | C | |
| 89 | A | | A |
| 90 | A | | A |
| 92 | A | A | A |
| 93 | A | A | A |
| 94 | A | A | A |
| 95 | A | A | A |
| 96 | A | A | A |
| 97 | A | A | A |
| 98 | A | A | A |
| 99 | A | A | A |
| 100 | A | C | A |
| 101 | A | A | A |
| 102 | A | A | |
| 103 | A | | |
| 104 | A | | |
| 105 | A | | A |
| 106 | A | A | A |
| 107 | A | | |
| 108 | A | A | |
| 109 | A | A | A |
| 110 | A | | |
| 111 | A | | B |
| 112 | A | A | A |
| 113 | A | A | A |
| 114 | A | A | A |
| 115 | A | A | |
| 116 | A | | |
| 117 | A | | A |
| 118 | A | A | A |
| 119 | A | A | A |
| 120 | A | | |
| 121 | A | A | A |
| 122 | A | A | A |
| 123 | A | A | A |
| 124 | A | A | A |
| 125 | A | A | A |
| 126 | A | A | A |
| 127 | A | A | A |
| 129 | A | | |
| 130 | A | A | A |
| 132 | A | | |
| 133 | A | A | |
| 134 | A | A | A |
| 135 | A | A | A |
| 136 | A | A | A |
| 137 | A | | |
| 139 | A | A | |
| 140 | A | A | A |
| 141 | A | A | |
| 142 | A | A | A |
| 143 | A | D | |
| 144 | A | A | |
| 145 | A | A | A |
| 146 | A | A | A |
| 147 | A | | |
| 148 | A | C | |
| 149 | A | A | |
| 150 | A | A | A |
| 151 | A | | |
| 152 | A | | |
| 153 | A | A | A |
| 154 | A | A | A |
| 155 | A | | |
| 156 | A | A | A |
| 157 | A | A | A |
| 158 | A | | |
| 159 | A | A | A |

TABLE 5-continued

| No | Test Example 1 | Test Example 2 | Test Example 3 |
|---|---|---|---|
| 160 | A | A | A |
| 161 | A | A | A |
| 162 | A | A | A |
| 163 | A | A | A |
| 164 | A | | A |
| 165 | A | A | A |
| 166 | A | A | A |
| 167 | A | A | A |
| 168 | A | A | A |
| 169 | A | A | A |
| 170 | A | A | A |
| 171 | A | | A |
| 172 | A | | |
| 173 | A | A | A |
| 174 | A | C | A |
| 175 | A | D | A |
| 176 | A | A | A |
| 177 | A | | |
| 178 | A | D | A |
| 179 | A | | A |
| 180 | A | | A |
| 181 | A | A | A |
| 182 | A | A | A |
| 183 | A | A | A |
| 184 | A | A | A |
| 185 | A | A | A |
| 186 | A | A | A |
| 187 | A | A | A |
| 188 | A | A | A |
| 189 | A | A | A |
| 190 | A | | A |
| 191 | A | A | |
| 192 | A | | |
| 193 | A | D | |
| 194 | A | | |
| 195 | A | A | A |
| 196 | A | A | A |
| 197 | A | C | A |
| 198 | A | A | A |
| 199 | A | A | A |
| 200 | A | A | A |
| 201 | A | A | A |
| 202 | A | | A |
| 203 | A | A | A |
| 204 | A | A | A |
| 205 | A | A | A |
| 206 | A | A | A |
| 207 | A | A | A |
| 208 | A | A | A |
| 209 | A | | |
| 210 | A | A | A |
| 211 | A | A | A |
| 212 | A | A | A |
| 213 | A | A | A |
| 214 | A | | |
| 215 | A | | A |
| 216 | A | A | A |
| 217 | A | A | A |
| 218 | A | A | A |
| 219 | A | A | A |
| 220 | A | A | A |
| 221 | A | A | A |
| 222 | A | | |
| 223 | A | | |
| 224 | A | | A |
| 225 | A | A | A |
| 226 | A | A | A |
| 227 | A | A | |
| 228 | A | A | |
| 229 | A | A | A |
| 230 | A | A | A |
| 231 | A | A | A |
| 232 | A | A | |
| 233 | A | A | |
| 234 | A | A | A |
| 235 | A | A | A |
| 236 | A | A | A |
| 237 | A | A | A |
| 238 | A | A | A |
| 239 | A | A | A |
| 240 | A | A | A |
| 241 | A | A | A |
| 242 | A | A | A |
| 243 | A | A | A |
| 244 | A | A | A |
| 245 | A | A | A |
| 246 | A | A | A |
| 247 | A | A | A |
| 248 | A | A | A |
| 249 | A | A | A |
| 250 | A | A | |
| 251 | A | | A |
| 252 | A | | A |
| 253 | A | A | A |
| 254 | A | A | A |
| 255 | A | A | A |
| 256 | A | A | A |
| 257 | A | A | A |
| 258 | A | | |
| 259 | A | A | A |
| 260 | A | A | A |
| 261 | A | A | A |
| 262 | A | A | A |
| 263 | A | A | A |
| 264 | A | A | A |
| 265 | A | A | A |
| 266 | A | A | A |
| 267 | A | A | A |
| 268 | A | A | A |
| 269 | A | A | A |
| 270 | A | A | A |
| 271 | A | C | A |
| 272 | A | A | A |
| 273 | A | | C |
| 274 | A | C | A |
| 275 | A | | |
| 276 | A | A | A |
| 277 | A | | |
| 278 | A | A | A |
| 279 | A | | C |
| 280 | A | C | A |
| 281 | A | A | A |
| 282 | A | A | A |
| 283 | A | A | A |
| 284 | A | A | A |
| 285 | A | A | A |
| 286 | A | C | A |
| 287 | A | A | A |
| 288 | A | A | A |
| 289 | A | | |
| 290 | A | D | |
| 292 | A | | |
| 293 | A | | A |
| 294 | A | A | A |
| 295 | A | A | A |
| 296 | A | A | A |
| 297 | A | A | A |
| 298 | A | | A |
| 299 | A | D | A |
| 300 | A | | |
| 301 | A | | A |
| 302 | A | | A |
| 303 | A | A | A |
| 305 | A | A | A |
| 306 | A | A | A |
| 307 | A | A | |
| 309 | A | A | A |
| 310 | A | A | A |
| 311 | A | A | |
| 312 | A | A | A |
| 313 | A | A | A |
| 314 | A | A | A |

TABLE 5-continued

| No | Test Example 1 | Test Example 2 | Test Example 3 |
|---|---|---|---|
| 315 | A | A | A |
| 316 | A | A | A |
| 317 | A | A | A |
| 318 | A | A | A |
| 319 | A |   | A |
| 320 | A | C | D |
| 321 | A | A | A |
| 322 | A |   |   |
| 324 | A |   |   |
| 325 | A | A | A |
| 326 | A |   | A |
| 327 | A |   | A |
| 328 | A | A | A |
| 329 | A |   | A |
| 330 | A | A | A |
| 332 | A |   | A |
| 333 | A | A | A |
| 334 | A |   | A |
| 335 | A |   | D |
| 336 | A | C | A |
| 337 | A | A |   |
| 338 | A | A |   |
| 339 | A | A | A |
| 340 | A | A |   |
| 341 | A | A | A |
| 342 | A |   |   |
| 343 | A |   |   |
| 344 | A |   | A |
| 345 | A |   |   |
| 346 | A | A | A |
| 347 | A |   |   |
| 348 | A | A | A |
| 349 | A | A | A |
| 351 | A | A | A |
| 352 | A |   | A |
| 353 | A |   | A |
| 355 | A | A | A |
| 356 | A |   |   |
| 357 | A | A | A |
| 358 | A | A | A |
| 359 | A | A | A |
| 360 | A | A | A |
| 361 | A | A | A |
| 362 | A | A | A |
| 363 | A | A | A |
| 364 | A | A | A |
| 365 | A | A | A |
| 366 | A | A | A |
| 367 | A | A | A |
| 368 | A |   | A |
| 369 | A | A | A |
| 370 | A | A |   |
| 371 | A | A | A |
| 372 | A | A | A |
| 373 | A | A | A |
| 374 | A | A | A |
| 375 | A | A |   |
| 376 | A | C | A |
| 377 | A |   |   |
| 378 | A |   |   |
| 379 | A |   |   |
| 380 | A | A | A |
| 381 | A | A |   |
| 382 | A | A | A |
| 383 | A | A | A |
| 384 | A | D | A |
| 385 | A | C |   |
| 386 | A |   |   |
| 387 | A |   |   |
| 388 | A | A | A |
| 389 | A |   |   |
| 390 | A |   |   |
| 391 | A |   |   |
| 392 | A | D | A |
| 393 | A | A | A |
| 394 | A | A |   |
| 395 | A | A | A |
| 396 | A | A | A |
| 397 | A | A | A |
| 398 | A | A | A |
| 399 | A | A | A |
| 400 | A | A | A |
| 401 | A | A | A |
| 402 | A | A | A |
| 403 | A | A | A |
| 404 | A | A | A |
| 405 | A | A | A |
| 406 | A | A | A |
| 407 | A | A | A |
| 408 | A | A | A |
| 409 | A | A | A |
| 410 | A | A |   |
| 411 | A | A | A |
| 412 | A | A | A |
| 413 | A | A | A |
| 414 | A | A | A |
| 415 | A | A | A |
| 417 | A | A | A |
| 419 | A | A | A |
| 420 | A | A | A |
| 421 | A | A | A |
| 422 | A | A | A |
| 423 | A | A | A |
| 424 | A | A | B |
| 425 | A | A |   |
| 426 | A | D | C |
| 427 | A | A | C |
| 428 | A | D | A |
| 429 | A | A | A |
| 430 | A | A | A |
| 431 | A | A | A |
| 432 | A | A | A |
| 433 | A | A | A |
| 434 | A | A | A |
| 435 | A | A | A |
| 436 | A | A | A |
| 437 | A | A | A |
| 438 | A | A | A |
| 439 | A | A | A |
| 440 | A | A | A |
| 441 | A | A | A |
| 442 | A | A | A |
| 443 | A | A | A |
| 444 | A | D | A |
| 445 | A |   | A |
| 446 | A |   |   |
| 447 | A |   |   |
| 448 | A | A | A |
| 449 | A | A | A |
| 450 | A | A | A |
| 451 | A |   | A |
| 452 | A |   |   |
| 453 | A | A | A |
| 454 | A | A | A |
| 459 | A |   |   |
| 460 | A | A | D |
| 461 | A |   | D |
| 462 | A | D | A |
| 463 | A | A | A |
| 465 | A |   |   |
| 467 | A | A | A |
| 469 | A |   |   |
| 470 | A | C | A |
| 471 | A |   | A |
| 472 | A |   | A |
| 473 | A |   | B |
| 474 | A |   | D |
| 475 | A |   | A |
| 478 | A |   |   |
| 480 | A |   | A |
| 481 | A | A | A |
| 482 | A | A | A |

TABLE 5-continued

| No | Test Example 1 | Test Example 2 | Test Example 3 |
| --- | --- | --- | --- |
| 483 | A | A | A |
| 484 | A | A | A |
| 486 | A | A | A |
| 490 | A | C | A |
| 491 | — | — | — |
| 492 | — | — | — |
| 493 | — | — | — |
| 494 | — | — | — |
| 495 | — | — | — |
| 496 | — | — | — |
| 2-3 | A | | A |
| 2-5 | A | C | |
| 2-6 | A | D | |
| 2-7 | A | | |
| 2-8 | A | A | |
| 2-9 | A | | |
| 2-10 | A | D | A |
| 2-11 | A | | |
| 2-12 | A | | A |
| 2-13 | A | | A |
| 2-14 | A | C | A |
| 2-15 | A | A | A |
| 2-16 | A | | |
| 2-17 | A | A | |
| 3-1 | A | A | |
| 3-2 | A | | |

What is claimed is:

1. A phthalamide derivative represented by the following general formula (I) or salt thereof:

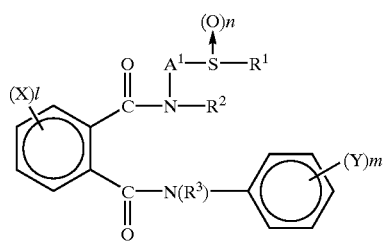

wherein $A^1$ represents $C_1$–$C_8$ alkylene group, substituted $C_1$–$C_8$ alkylene group having at least one, same or different substituents selected from the group consisting of halogen atom, cyano group, nitro group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, hydroxy $C_1$–$C_6$ alkyl group, $C_1$–$C_6$ alkoxy $C_1$–$C_6$ alkyl group, $C_1$–$C_6$ alkylthio $C_1$–$C_6$ alkyl group, $C_1$–$C_6$ alkoxycarbonyl group, phenyl group and substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, $C_3$–$C_8$ alkenylene group, substituted $C_3$–$C_8$ alkenylene group having at least one, same or different substituents selected from the group consisting of halogen atom, cyano group, nitro group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, halo $C_1$–$C_6$ alkylsulfonyl group, $C_1$–$C_6$ alkylthio $C_1$–$C_6$ alkyl group, $C_1$–$C_6$ alkoxycarbonyl group, phenyl group and substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, $C_3$–$C_8$ alkynylene group, or substituted $C_3$–$C_8$ alkynylene group having at least one, same or different substituents selected from the group consisting of halogen atom, cyano group, nitro group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, $C_1$–$C_6$ alkylthio $C_1$–$C_6$ alkyl group, $C_1$–$C_6$ alkoxycarbonyl group, phenyl group and substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, further, an arbitrary saturated carbon atom in said $C_1$–$C_8$ alkylene group, substituted $C_1$–$C_8$ alkylene group, $C_3$–$C_8$ alkenylene group, substituted $C_3$–$C_8$ alkenylene group, $C_3$–$C_8$ alkynylene group and substituted $C_3$–$C_8$ alkynylene group may be substituted with a $C_2$–$C_5$ alkylene group to form a $C_3$–$C_6$ cycloalkane ring, and arbitrary two carbon atoms in said $C_1$–$C_8$ alkylene group, substituted $C_1$–$C_8$ alkylene group, $C_3$–$C_8$ alkenylene group and substituted $C_3$–$C_8$ alkenylene group may be taken conjointly with an alkylene group or an alkenylene group to form a $C_3$–$C_6$ cycloalkane ring or $C_3$–$C_6$ cycloalkene ring;

$R^1$ represents hydrogen atom, mercapto group, $C_1$–$C_6$ alkylthio group, halo $C_1$–$C_6$ alkylthio group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^2$—$R^4$ [wherein $A^2$ represents —C(=O)—, —C(=S)—, or —C(=N$R^5$)— (in which $R^5$ represents hydrogen atom, $C_1$–$C_6$ alkyl group, $C_1$–$C_6$ alkoxy group, mono $C_1$–$C_6$ alkylamino group, di $C_1$–$C_6$ alkylamino group in which $C_1$–$C_6$ alkyl groups may be same or different, $C_1$–$C_6$ alkoxycarbonyl group, phenyl group or substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group), $C_1$–$C_8$ alkylene group, halo $C_1$–$C_8$ alkylene group, $C_3$–$C_6$ alkenylene group, halo $C_3$–$C_6$ alkenylene group, $C_3$–$C_6$ alkynylene group or halo $C_3$–$C_6$ alkynylene group; and (1) in cases where $A^2$ represents —C(=O)—, —C(=S)— or —C(=N$R^5$)— wherein $R^5$ is as defined above, $R^4$ represents hydrogen atom, $C_1$–$C_6$ alkyl group, halo $C_1$–$C_6$ alkyl group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$Z^1$—$R^6$ wherein $Z^1$ represents —O—, —S— or —N($R^7$)— (wherein $R^7$ represents hydrogen atom, $C_1$–$C_6$ alkyl group, $C_1$–$C_6$ alkylcarbonyl group, halo $C_1$–$C_6$ alkylcarbonyl group or $C_1$–$C_6$ alkoxycarbonyl group), and $R^6$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenyl $C_1$–$C_4$ alkyl group, substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, and (2) in cases where $A^2$ represents $C_1$–$C_8$ alkylene group, halo $C_1$–$C_8$ alkylene group, $C_3$–$C_6$ alkenylene group, halo $C_3$–$C_6$ alkenylene group, $C_3$–$C_6$ alkynylene group or halo $C_3$–$C_6$ alkynylene group, $R^4$ represents hydrogen atom, halogen atom, cyano group, nitro group, $C_3$–$C_6$ cycloalkyl group, halo $C_3$–$C_6$ cycloalkyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$Z^2$—$R^8$ wherein $Z^2$ represents —O—, —S—, —SO—, —SO$_2$—, —N($R^9$)— (wherein $R^9$ represents hydrogen atom, $C_1$–$C_6$ alkyl group, $C_1$–$C_6$ alkylcarbonyl group, halo $C_1$–$C_6$ alkylcarbonyl group, $C_1$–$C_6$ alkoxycarbonyl group, phenylcarbonyl group, or substituted phenylcarbonyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group), —C(=O)— or —C(=NOR$^{10}$)— (wherein R$^{10}$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, phenyl $C_1$–$C_4$ alkyl group or substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group) and R$^8$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, $C_1$–$C_6$ alkylcarbonyl group, halo $C_1$–$C_6$ alkylcarbonyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenyl $C_1$–$C_4$ alkyl group, substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group], or alternatively, R$^1$ may be combined with A$^1$ to form a 5- to 8-membered ring which may be intercepted by 1 or 2, same or different oxygen atoms, sulfur atoms or nitrogen atoms;

R$^2$ and R$^3$ which may be same or different, represent hydrogen atom, $C_3$–$C_6$ cycloalkyl group or —A$^2$—R$^4$ wherein A$^2$ and R$^4$ are as defined above; or alternatively, R$^2$ may be combined with A$^1$ or R$^1$ to form a 5- to 7-membered ring which may be intercepted by 1 or 2, same or different oxygen atoms, sulfur atoms or nitrogen atoms;

X which may be same or different, represents halogen atom, cyano group, nitro group, $C_3$–$C_6$ cycloalkyl group, halo $C_3$–$C_6$ cycloalkyl group, $C_1$–$C_6$ alkoxycarbonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkyl sulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —A$^3$—R$^{11}$ [wherein A$^3$ represents —O—, —S—, —SO—, —SO$_2$—, —C(=O)—, —C(=NOR$^{12}$)— (in which R$^{12}$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, $C_3$–$C_6$ cycloalkyl group, phenyl $C_1$–$C_4$ alkyl group or substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group), $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group; and (1) in cases where A$^3$ represents —O—, —S—, —SO— or —SO$_2$—, R$^{11}$ represents halo $C_3$–$C_6$ cycloalkyl group, halo $C_3$–$C_6$ cycloalkenyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^4$—$R^{13}$ (wherein $A^4$ represents $C_1$–$C_6$ alkylene group, halo $C_1$–$C_6$ alkylene group, $C_3$–$C_6$ alkenylene group, halo $C_3$–$C_6$ alkenylene group, $C_3$–$C_6$ alkynylene group or halo $C_3$–$C_6$ alkynylene group, and $R^{13}$ represents hydrogen atom, halogen atom, $C_3$–$C_6$ cycloalkyl group, halo $C_3$–$C_6$ cycloalkyl group, $C_1$–$C_6$ alkoxycarbonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^5$—$R^{14}$ (wherein $A^5$ represents —O—, —S—, —SO—, —$SO_2$— or —C(=O)—, and $R^{14}$ represents $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group)), and (2) in cases where $A^3$ represents —C(=O)— or —C(=$NOR^{12}$)— wherein $R^{12}$ is as defined above, $R^{11}$ represents hydrogen atom, $C_1$–$C_6$ alkyl group, halo $C_1$–$C_6$ alkyl group, $C_2$–$C_6$ alkenyl group, halo $C_2$–$C_6$ alkenyl group, $C_3$–$C_6$ cycloalkyl group, halo $C_3$–$C_6$ cycloalkyl group, $C_1$–$C_6$ alkoxy group, $C_1$–$C_6$ alkylthio group, mono $C_1$–$C_6$ alkylamino group, di $C_1$–$C_6$ alkylamino group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylamino group, substituted phenylamino group having on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, and (3) in cases where $A^3$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group, $R^{11}$ represents hydrogen atom, hydroxy group, halogen atom, $C_3$–$C_6$ cycloalkyl group, halo $C_3$–$C_6$ cycloalkyl group, $C_1$–$C_6$ alkoxycarbonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^6$—$R^{15}$ (wherein $A^6$ represents —O—, —S—, —SO— or —$SO_2$—, and $R^{15}$ represents $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^7$—$R^{16}$ (wherein $A^7$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group, and $R^{16}$ represents hydrogen atom, halogen atom, $C_3$–$C_6$ cycloalkyl group, halo $C_3$–$C_6$ cycloalkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenoxy group, substituted phenoxy group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group))]; and 1 represents an integer of 0 to 4; and alternatively, X may be taken conjointly with the adjacent carbon atom on the phenyl ring to form a fused ring, and said fused ring may have at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group; and Y may be same or different and represents halogen atom, cyano group, nitro group, halo $C_3$–$C_6$ cycloalkyl group, tri $C_1$–$C_6$ alkylsilyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^3$—$R^{11}$ wherein $A^3$ and $R^{11}$ are as defined above; and m represents an integer of 0 to 5; and Y may be taken conjointly with an adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, and substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group; and n represents an integer of 0 to 2;

provided that when X, $R^2$ and $R^3$ simultaneously represent hydrogen atom, m represents an integer of 2, Y of the 2-position represents fluorine atom and Y of the 3-position represents chlorine atom, then $A^1$ is not propylene group, $R^1$ is not methyl group and n is not an integer of 0.

2. A phthalamide derivative or salt thereof according to claim 1, wherein $A^1$ represents $C_1$–$C_8$ alkylene group, substituted $C_1$–$C_8$ alkylene group having at least one, same or different substituents selected from the group consisting of halogen atom, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, $C_1$–$C_6$ alkylthio $C_1$–$C_6$ alkyl group, phenyl group and substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, $C_3$–$C_8$ alkenylene group, substituted $C_3$–$C_8$ alkenylene group having at least one, same or different substituents selected from the group consisting of halogen atom, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, and $C_1$–$C_6$ alkylthio $C_1$–$C_6$ alkyl group, $C_3$–$C_8$ alkynylene group, or substituted $C_3$–$C_8$ alkynylene group having at least one, same or different substituents selected from the group consisting of halogen atom, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group and $C_1$–$C_6$ alkylthio $C_1$–$C_6$ alkyl group, further, an arbitrary saturated carbon atom in said $C_1$–$C_8$ alkylene group, substituted $C_1$–$C_8$ alkylene group, $C_3$–$C_8$ alkenylene group, substituted $C_3$–$C_8$ alkenylene group, $C_3$–$C_8$ alkynylene group and substituted $C_3$–$C_8$ alkynylene group may be substituted with a $C_2$–$C_5$ alkylene group to form a $C_3$–$C_6$ cycloalkane ring, and arbitrary two carbon atoms in said $C_1$–$C_8$ alkylene group, substituted $C_1$–$C_8$ alkylene group, $C_3$–$C_8$ alkenylene group and substituted $C_3$–$C_8$ alkenylene group may be taken conjointly with an alkylene group or an alkenylene group to form a $C_3$–$C_6$ cycloalkane ring or $C_3$–$C_6$ cycloalkene ring;

$R^1$ represents hydrogen atom, mercapto group, $C_1$–$C_6$ alkylthio group, halo $C_1$–$C_6$ alkylthio group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^2$—$R^4$ [wherein $A^2$ represents —C(=O)—, —C(=S)—, or —C(=NR^5)— (in which $R^5$ represents hydrogen atom, $C_1$–$C_6$ alkyl group, $C_1$–$C_6$ alkoxy group, mono $C_1$–$C_6$ alkylamino group, di $C_1$–$C_6$ alkylamino group in which $C_1$–$C_6$ alkyl groups may be same or different, $C_1$–$C_6$ alkoxycarbonyl group, phenyl group or substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group), $C_1$–$C_8$ alkylene group, halo $C_1$–$C_8$ alkylene group, $C_3$–$C_6$ alkenylene group, halo $C_3$–$C_6$ alkenylene group, $C_3$–$C_6$ alkynylene group or halo $C_3$–$C_6$ alkynylene group; and (1) in cases where $A^2$ represents —C(=O)—, —C(=S)— or —C(=NR^5)— wherein $R^5$ is as defined above, $R^4$ represents hydrogen atom, $C_1$–$C_6$ alkyl group, halo $C_1$–$C_6$ alkyl group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$Z^1$—$R^6$ wherein $Z^1$ represents —O—, —S— or —N($R^7$)— (wherein $R^7$ represents hydrogen atom, $C_1$–$C_6$ alkyl group, $C_1$–$C_6$ alkylcarbonyl group, halo $C_1$–$C_6$ alkylcarbonyl group or $C_1$–$C_6$ alkoxycarbonyl group), and $R^6$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkyl group, substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, and (2) in cases where $A^2$ represents $C_1$–$C_8$ alkylene group, halo $C_1$–$C_8$ alkylene group, $C_3$–$C_6$ alkenylene group, halo $C_3$–$C_6$ alkenylene group, $C_3$–$C_6$ alkynylene group or halo $C_3$–$C_6$ alkynylene group, $R^4$ represents hydrogen atom, halogen atom, cyano group, nitro group, $C_3$–$C_6$ cycloalkyl group, halo $C_3$–$C_6$ cycloalkyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, and halo $C_1$–$C_6$ alkylsulfonyl group, or —$Z^2$—$R^8$ wherein $Z^2$ represents —O—, —S—, —SO—, —$SO_2$—, —N($R^9$)— (wherein $R^9$ represents hydrogen atom, $C_1$–$C_6$ alkyl group, $C_1$–$C_6$ alkylcarbonyl group, halo $C_1$–$C_6$ alkylcarbonyl group, $C_1$–$C_6$ alkoxycarbonyl group, phenylcarbonyl group, or substituted phenylcarbonyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfonyl group, halo $C_1$–$C_6$ alkylsulfonyl group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group), —C(=O)— or —C(=NO$R^{10}$)— (wherein $R^{10}$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, phenyl $C_1$–$C_4$ alkyl group or substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, and halo $C_1$–$C_6$ alkylsulfonyl group) and $R^8$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, $C_1$–$C_6$ alkylcarbonyl group, halo $C_1$–$C_6$ alkylcarbonyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkyl group, substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group], or alternatively, $R^1$ may be combined with $A^1$ to form a 5- to 8-membered ring which may be intercepted by 1 or 2, same or different oxygen atoms, sulfur atoms or nitrogen atoms;

$R^2$ and $R^3$ which may be same or different, represent hydrogen atom, $C_1$–$C_6$ cycloalkyl group or —$A^2$—$R^4$ wherein $A^2$ and $R^4$ are as defined above; or alternatively, $R^2$ may be combined with $A^1$ or $R^1$ to form a 5- to 7-membered ring which may be intercepted by 1 or 2, same or different oxygen atoms, sulfur atoms or nitrogen atoms;

X which may be same or different, represents halogen atom, cyano group, nitro group, $C_1$–$C_6$ alkyl group, halo $C_1$–$C_6$ alkyl group, $C_2$–$C_6$ alkenyl group, halo $C_1$–$C_6$ alkenyl group, $C_2$–$C_6$ alkynyl group, halo $C_2$–$C_6$ alkynyl group, $C_3$–$C_6$ cycloalkyl group, halo $C_3$–$C_6$ cycloalkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, or $C_1$–$C_6$ alkoxycarbonyl group and 1 represents an integer of 0 to 4; and alternatively, X may be taken conjointly with the adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and Y may be same or different and represents halogen atom, cyano group, nitro group, halo $C_3$–$C_6$ cycloalkyl group, tri $C_1$–$C_6$ alkylsilyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$A^3$—$R^{11}$ [wherein $A^3$ represents —O—, —S—, —SO—, —$SO_2$—, —C(=O)—, —C(=$NOR^{12}$)— (in which $R^{12}$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, $C_3$–$C_6$ cycloalkyl group, phenyl $C_1$–$C_4$ alkyl group or substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, and halo $C_1$–$C_6$ alkylsulfonyl group), $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group; and (1) in cases where $A^3$ represents —O—, —S—, —SO— or —$SO_2$—, $R^{11}$ represents phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$A^4$—$R^{13}$ (wherein $A^4$ represents $C_1$–$C_6$ alkylene group, halo $C_1$–$C_6$ alkylene group, $C_3$–$C_6$ alkenylene group, halo $C_3$–$C_6$ alkenylene group, $C_3$–$C_6$ alkynylene group or halo $C_3$–$C_6$ alkynylene group, and $R^{13}$ represents hydrogen atom, halogen atom, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, and halo $C_1$–$C_6$ alkylsulfonyl group, or —$A^5$—$R^{14}$ (wherein $A^5$ represents —O—, —S—, —SO—, —$SO_2$— or —C(=O)—, and $R^{14}$ represents $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group)), and (2) in cases where $A^3$ represents —C(=O)— or —C(=$NOR^{12}$)— wherein $R^{12}$ is as defined above, $R^{11}$ represents hydrogen atom, $C_1$–$C_6$ alkyl group, halo $C_1$–$C_6$ alkyl group, $C_2$–$C_6$ alkenyl group, halo $C_2$–$C_6$ alkenyl group, $C_3$–$C_6$ cycloalkyl group, halo $C_3$–$C_6$ cycloalkyl group, $C_1$–$C_6$ alkoxy group, $C_1$–$C_6$ alkylthio group, mono $C_1$–$C_6$ alkylamino group, di $C_1$–$C_6$ alkylamino group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenylamino group, substituted phenylamino group having on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, and (3) in cases where $A^3$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group, $R^{11}$ represents hydrogen atom, hydroxy group, halogen atom, $C_3$–$C_6$ cycloalkyl group, halo $C_3$–$C_6$ cycloalkyl group, $C_1$–$C_6$ alkoxycarbonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$A^6$—$R^{15}$ (wherein $A^6$ represents —O—, —S—, —SO— or —$SO_2$—, and $R^{15}$ represents $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$A^7$—$R^{16}$ (wherein $A^7$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group, and $R^{16}$ represents hydrogen atom, halogen atom, $C_3$–$C_6$ cycloalkyl group, halo $C_3$–$C_6$ cycloalkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenoxy group, substituted phenoxy group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group))] and m represents an integer of 1 to 5; and Y may be taken conjointly with an adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and n represents an integer of 0 to 2.

3. A phthalamide derivative or salt thereof according to claim 2, wherein $A^1$ represents $C_1$–$C_8$ alkylene group, substituted $C_1$–$C_8$ alkylene group having at least one, same or different substituents selected from the group consisting of halogen atom, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group and $C_1$–$C_6$ alkylthio $C_1$–$C_6$ alkyl group and further, an arbitrary saturated carbon atom in said $C_1$–$C_8$ alkylene group and substituted $C_1$–$C_8$ alkylene group may be substituted with a $C_2$–$C_5$ alkylene group to form a $C_3$–$C_6$ cycloalkane ring, and arbitrary two carbon atoms in said $C_1$–$C_8$ alkylene group and substituted $C_1$–$C_8$ alkylene group may be taken conjointly with an alkylene group or an alkenylene group to form a $C_3$–$C_6$ cycloalkane ring;

$R^1$ represents hydrogen atom, mercapto group, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, halo $C_3$–$C_6$ cycloalkyl group, $C_1$–$C_6$ alkylthio group, halo $C_1$–$C_6$ alkylthio group, $C_1$–$C_6$ alkoxy $C_1$–$C_6$ alkyl group, $C_1$–$C_6$ alkylthio $C_1$–$C_6$ alkyl group, mono $C_1$–$C_6$ alkylamino $C_1$–$C_6$ alkyl group, di $C_1$–$C_6$ alkylamino $C_1$–$C_6$ alkyl group in which $C_1$–$C_6$ alkyl groups may be same or different, $C_1$–$C_6$ alkylcarbonyl group, halo $C_1$–$C_6$ alkylcarbonyl group, $C_1$–$C_6$ alkylthiocarbonyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, mono $C_1$–$C_6$ alkylamino thiocarbonyl group, di $C_1$–$C_6$ alkylamino thiocarbonyl group in which $C_1$–$C_6$ alkyl groups may be same or different, $C_1$–$C_6$ alkylcarbonyl $C_1$–$C_6$ alkyl group, $C_1$–$C_6$ alkoxyimino $C_1$–$C_6$ alkyl group, $C_1$–$C_6$ alkoxycarbonyl $C_1$–$C_6$ alkyl group, mono $C_1$–$C_6$ alkylaminocarbonyl $C_1$–$C_6$ alkyl group, di $C_1$–$C_6$ alkylaminocarbonyl $C_1$–$C_6$ alkyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different and $C_1$–$C_6$ alkoxycarbonyl group, phenyl $C_1$–$C_6$ alkyl group, substituted phenyl $C_1$–$C_6$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylcarbonyl group, substituted phenylcarbonyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different and $C_1$–$C_6$ alkoxycarbonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different and $C_1$–$C_6$ alkoxycarbonyl group, or alternatively, $R^1$ may be combined with $A^1$ to form a 5- to 8-membered ring which may be intercepted by 1 or 2, same or different oxygen atoms, sulfur atoms or nitrogen atoms;

$R^2$ and $R^3$ which may be same or different, represent hydrogen atom, $C_1$–$C_6$ alkyl group; or alternatively, $R^2$ may be combined with $A^1$ or $R^1$ to form a 5- to 7-membered ring which may be intercepted by 1 or 2, same or different oxygen atoms, sulfur atoms or nitrogen atoms;

X which may be same or different, represents halogen atom, nitro group, $C_1$–$C_6$ alkyl group, halo $C_1$–$C_6$ alkyl group, $C_2$–$C_6$ alkenyl group, halo $C_2$–$C_6$ alkenyl group, $C_2$–$C_6$ alkynyl group, halo $C_2$–$C_6$ alkynyl group, $C_3$–$C_6$ cycloalkyl group, halo $C_3$–$C_6$ cycloalkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group or halo $C_1$–$C_6$ alkylsulfonyl group and l represents an integer of 0 to 4; and alternatively, X may be taken conjointly with the adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and Y may be same or different and represents halogen atom, $C_1$–$C_6$ alkyl group, halo $C_1$–$C_6$ alkyl group, hydroxy halo $C_1$–$C_6$ alkyl group, $C_1$–$C_6$ alkoxy halo $C_1$–$C_6$ alkyl group, $C_1$–$C_6$ alkylthio halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_1$–$C_6$ alkoxy group, halo $C_1$–$C_6$ alkoxy group, $C_1$–$C_6$ alkoxy halo $C_1$–$C_6$ alkoxy group, $C_1$–$C_6$ alkylthio halo $C_1$–$C_6$ alkoxy group, halo $C_1$–$C_6$ alkoxy halo $C_1$–$C_6$ alkoxy group, halo $C_3$–$C_6$ alkenyloxy group, $C_1$–$C_6$ alkylthio group, halo $C_1$–$C_6$ alkylthio group, halo $C_1$–$C_6$ alkoxy halo $C_1$–$C_6$ alkylthio group, halo $C_1$–$C_6$ alkenylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, $C_1$–$C_6$ alkoxycarbonyl group, $C_3$–$C_6$ cycloalkyl group, halo $C_3$–$C_6$ cycloalkyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group, and halo $C_1$–$C_6$ alkylsulfonyl group, phenoxy group, substituted phenoxy group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group, and halo $C_1$–$C_6$ alkylsulfonyl group, phenylthio group, substituted phenylthio group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group, pyridyloxy group, substituted pyridyloxy group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group, pyridylthio group, substituted pyridylthio group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group; and m represents an integer of 1 to 5; and Y may be taken conjointly with an adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and n represents an integer of 0 to 2.

4. A phthalamide derivative or salt thereof according to claim 3, wherein $A^1$ represents $C_1$–$C_8$ alkylene group;

$R^1$ represents hydrogen atom, $C_1$–$C_6$ alkyl group, halo $C_1$–$C_6$ alkyl group, $C_3$–$C_6$ alkenyl group, $C_3$–$C_6$ alkynyl group, $C_3$–$C_6$ cycloalkyl group, $C_1$–$C_6$ alkylthio group, $C_1$–$C_6$ alkoxy $C_1$–$C_6$ alkyl group, $C_1$–$C_6$ alkylthio $C_1$–$C_6$ alkyl group, $C_1$–$C_6$ alkylcarbonyl group, mono $C_1$–$C_6$ alkylaminocarbonyl group, di $C_1$–$C_6$ alkylaminocarbonyl group in which $C_1$–$C_6$ alkyl groups may be same or different, mono $C_1$–$C_6$ alkylaminothiocarbonyl group, di $C_1$–$C_6$ alkylaminothiocarbonyl group in which $C_1$–$C_6$ alkyl groups may be same or different, $C_1$–$C_6$ alkylcarbonyl $C_1$–$C_6$ alkyl group, $C_1$–$C_6$ alkoxyimino $C_1$–$C_6$ alkyl group, $C_1$–$C_6$ alkoxycarbonyl $C_1$–$C_6$ alkyl group, mono $C_1$–$C_6$ alkylaminocarbonyl $C_1$–$C_6$ alkyl group or di $C_1$–$C_6$ alkylaminocarbonyl $C_1$–$C_6$ alkyl group in which $C_1$–$C_6$ alkyl groups may be same or different;

$R^2$ and $R^3$ which may be same or different, represent hydrogen atom or $C_1$–$C_6$ alkyl group;

X which may be same or different, represents halogen atom, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group or halo $C_1$–$C_6$ alkylsulfonyl group; and l represents an integer of 0 to 4; and alternatively, X may be taken conjointly with the adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group;

Y may be same or different and represents halogen atom, $C_1$–$C_6$ alkyl group, halo $C_1$–$C_6$ alkyl group, $C_1$–$C_6$ alkoxy halo $C_1$–$C_6$ alkyl group, $C_1$–$C_6$ alkoxy group, halo $C_1$–$C_6$ alkoxy group, halo $C_1$–$C_6$ alkoxy halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group, substituted phenoxy group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group, or substituted pyridyloxy group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group; and m represents an integer of 1 to 5; and Y may be taken conjointly with an adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group; and n represents an integer of 0 to 2.

5. An agrohorticultural insecticide characterized by containing, as an active ingredient thereof, a phthalamide derivative represented by the following general formula (I) or salt thereof:

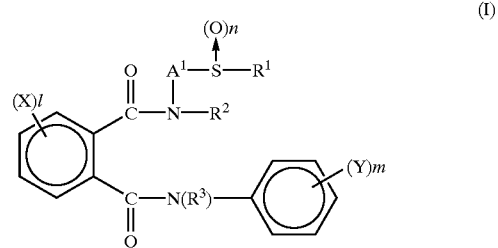

(I)

wherein $A^1$ represents $C_1$–$C_8$ alkylene group, substituted $C_1$–$C_8$ alkylene group having at least one, same or different substituents selected from the group consisting of halogen atom, cyano group, nitro group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, hydroxy $C_1$–$C_6$ alkyl group, $C_1$–$C_6$ alkoxy $C_1$–$C_6$ alkyl group, $C_1$–$C_6$ alkylthio $C_1$–$C_6$ alkyl group, $C_1$–$C_6$ alkoxycarbonyl group, phenyl group and substituted phenyl group having at least one, same or different substituents selected from the group consisting of halogen atom, cyano group, nitro group, $C_1$–$C_6$, alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, $C_3$–$C_8$ alkenylene group, substituted $C_3$–$C_8$ alkenylene group having at least one, same or different substituents selected from the group consisting of halogen atom, cyano group, nitro group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, $C_1$–$C_6$ alkylthio $C_1$–$C_6$ alkyl group, $C_1$–$C_6$ alkoxycarbonyl group, phenyl group and substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, $C_3$–$C_8$ alkynylene group, or substituted $C_3$–$C_8$ alkynylene group having at least one, same or different substituents selected from the group consisting of halogen atom, cyano group, nitro group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, $C_1$–$C_6$ alkylthio $C_1$–$C_6$ alkyl group, $C_1$–$C_6$ alkoxycarbonyl group, phenyl group and substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, further, an arbitrary saturated carbon atom in said $C_1$–$C_8$ alkylene group, substituted $C_1$–$C_8$ alkylene group, $C_3$–$C_8$ alkenylene group, substituted $C_3$–$C_8$ alkenylene group, $C_3$–$C_8$ alkynylene group and substituted $C_3$–$C_8$ alkynylene group may be substituted with a $C_2$–$C_5$ alkylene group to form a $C_3$–$C_6$ cycloalkane ring, and arbitrary two carbon atoms in said $C_1$–$C_8$ alkylene group, substituted $C_1$–$C_8$ alkylene group, $C_3$–$C_8$ alkenylene group and substituted $C_3$–$C_8$ alkenylene group may be taken conjointly with an alkylene group or an alkenylene group to form a $C_3$–$C_6$ cycloalkane ring or $C_3$–$C_6$ cycloalkene ring;

$R^1$ represents hydrogen atom, mercapto group, $C_1$–$C_6$ alkylthio group, halo $C_1$–$C_6$ alkylthio group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^2$—$R^4$ [wherein $A^2$ represents —C(=O)—, —C(=S)—, or —C(=NR$^5$)— (in which $R^5$ represents hydrogen atom, $C_1$–$C_6$ alkyl group, $C_1$–$C_6$ alkoxy group, mono $C_1$–$C_6$ alkylamino group, di $C_1$–$C_6$ alkylamino group in which $C_1$–$C_6$ alkyl groups may be same or different, $C_1$–$C_6$ alkoxycarbonyl group, phenyl group or substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group), $C_1$–$C_8$ alkylene group, halo $C_1$–$C_8$ alkylene group, $C_3$–$C_6$ alkenylene group, halo $C_3$–$C_6$ alkenylene group, $C_3$–$C_6$ alkynylene group or halo $C_3$–$C_6$ alkynylene group; and (1) in cases where $A^2$ represents —C(=O)—, —C(=S)— or —C(=NR$^5$)— wherein $R^5$ is as defined above, $R^4$ represents hydrogen atom, $C_1$–$C_6$ alkyl group, halo $C_1$–$C_6$ alkyl group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$Z^1$—$R^6$ wherein $Z^1$ represents —O—, —S— or —N($R^7$)— (wherein $R^7$ represents hydrogen atom, $C_1$–$C_6$ alkyl group, $C_1$–$C_6$ alkylcarbonyl group, halo $C_1$–$C_6$ alkylcarbonyl group or $C_1$–$C_6$ alkoxycarbonyl group), and $R^6$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenyl $C_1$–$C_4$ alkyl group, substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, and (2) in cases where $A^2$ represents $C_1$–$C_8$ alkylene group, halo $C_1$–$C_8$ alkylene group, $C_3$–$C_6$ alkenylene group, halo $C_3$–$C_6$ alkenylene group, $C_3$–$C_6$ alkynylene group or halo $C_3$–$C_6$ alkynylene group, $R^4$ represents hydrogen atom, halogen atom, cyano group, nitro group, $C_3$–$C_6$ cycloalkyl group, halo $C_3$–$C_6$ cycloalkyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, phenyl group, substituted phenyl group having at least one, same or different substituents consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$Z^2$—$R^8$ wherein $Z^2$ represents —O—, —S—, —SO—, —$SO_2$—, —N($R^9$)— (wherein $R^9$ represents hydrogen atom, $C_1$–$C_6$ alkyl group, $C_1$–$C_6$ alkylcarbonyl group, halo $C_1$–$C_6$ alkylcarbonyl group, $C_1$–$C_6$ alkoxycarbonyl group, phenylcarbonyl group, or substituted phenylcarbonyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group), —C(=O)— or —C(=$NOR^{10}$)— (wherein $R^{10}$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, phenyl $C_1$–$C_4$ alkyl group or substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group) and $R^8$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, $C_1$–$C_6$ alkylcarbonyl group, halo $C_1$–$C_6$ alkylcarbonyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenyl $C_1$–$C_4$ alkyl group, substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group], or alternatively, $R^1$ may be combined with $A^1$ to form a 5- to 8-membered ring which may be intercepted by 1 or 2, same or different oxygen atoms, sulfur atoms or nitrogen atoms;

$R^2$ and $R^3$ which may be same or different, represent hydrogen atom, $C_3$–$C_6$ cycloalkyl group or —$A^2$—$R^4$ wherein $A^2$ and $R^4$ are as defined above; or alternatively, $R^2$ may be combined with $A^1$ or $R^1$ to form a 5- to 7-membered ring which may be intercepted by 1 or 2, same or different oxygen atoms, sulfur atoms or nitrogen atoms;

X which may be same or different, represents halogen atom, cyano group, nitro group, $C_3$–$C_6$ cycloalkyl group, halo $C_3$–$C_6$ cycloalkyl group, $C_1$–$C_6$ alkoxycarbonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^3$—$R^{11}$ [wherein $A^3$ represents —O—, —S—, —SO—, —$SO_2$—, —C(=O)—, —C(=$NOR^{12}$)— (in which $R^{12}$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, $C_3$–$C_6$ cycloalkyl group, phenyl $C_1$–$C_4$ alkyl group or substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group), $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or, halo $C_3$–$C_6$ alkynylene group; and (1) in cases where $A^3$ represents —O—, —S—, —SO— or —$SO_2$—, $R^{11}$ represents halo $C_3$–$C_6$ cycloalkyl group, halo $C_3$–$C_6$ cycloalkenyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^4$—$R^{13}$ (wherein $A^4$ represents $C_1$–$C_6$ alkylene group, halo $C_1$–$C_6$ alkylene group, $C_3$–$C_6$ alkenylene group, halo $C_3$–$C_6$ alkenylene group, $C_3$–$C_6$ alkynylene group or halo $C_3$–$C_6$ alkynylene group, and $R^{13}$ represents hydrogen atom, halogen atom, $C_3$–$C_6$ cycloalkyl group, halo $C_3$–$C_6$ cycloalkyl group, $C_1$–$C_6$ alkoxycarbonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^5$—$R^{14}$ (wherein $A^5$ represents —O—, —S—, —SO—, —$SO_2$— or —C(=O)—, and $R^{14}$ represents $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group)), and (2) in cases where $A^3$ represents —C(=O)— or —C(=NOR$^{12}$)— wherein R$^{12}$ is as defined above, R$^{11}$ represents hydrogen atom, $C_1$–$C_6$ alkyl group, halo $C_1$–$C_6$ alkyl group, $C_2$–$C_6$ alkenyl group, halo $C_2$–$C_6$ alkenyl group, $C_3$–$C_6$ cycloalkyl group, halo $C_3$–$C_6$ cycloalkyl group, $C_1$–$C_6$ alkoxy group, $C_1$–$C_6$ alkylthio group, mono $C_1$–$C_6$ alkylamino group, di $C_1$–$C_6$ alkylamino group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylamino group, substituted phenylamino group having on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, and (3) in cases where $A^3$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group, R$^{11}$ represents hydrogen atom, hydroxy group, halogen atom, $C_3$–$C_6$ cycloalkyl group, halo $C_3$–$C_6$ cycloalkyl group, $C_1$–$C_6$ alkoxycarbonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^6$—R$^{15}$ (wherein $A^6$ represents —O—, —S—, —SO— or —SO$_2$—, and R$^{15}$ represents $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^7$—R$^{16}$ (wherein $A^7$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group, and R$^{16}$ represents hydrogen atom, halogen atom, $C_3$–$C_6$ cycloalkyl group, halo $C_3$–$C_6$ cycloalkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenoxy group, substituted phenoxy group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group))]; and l represents an integer of 0 to 4; and alternatively, X may be taken conjointly with the adjacent carbon atom on the phenyl ring to form a fused ring, and said fused ring may have at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group; and Y may be same or different and represents halogen atom, cyano group, nitro group, halo $C_3$–$C_6$ cycloalkyl group, tri $C_1$–$C_6$ alkylsilyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^3$—$R^{11}$ wherein $A^3$ and $R^{11}$ are as defined above; and m represents an integer of 0 to 5; and Y may be taken conjointly with an adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, and substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group; and n represents an integer of 0 to 2.

6. An agrohorticultural insecticide according to claim 5, wherein $A^1$ represents $C_1$–$C_8$ alkylene group, substituted $C_1$–$C_8$ alkylene group having at least one, same or different substituents selected from the group consisting of halogen atom, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, $C_1$–$C_6$ alkylthio $C_1$–$C_6$ alkyl group, phenyl group and substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, $C_3$–$C_8$ alkenylene group, substituted $C_3$–$C_8$ alkenylene group having at least one, same or different substituents selected from the group consisting of halogen atom, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, and $C_1$–$C_6$ alkylthio $C_1$–$C_6$ alkyl group, $C_3$–$C_8$ alkynylene group, or substituted $C_3$–$C_8$ alkynylene group having at least one, same or different substituents selected from the group consisting of halogen atom, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group and $C_1$–$C_6$ alkylthio $C_1$–$C_6$ alkyl group, further, an arbitrary saturated carbon atom in said $C_1$–$C_8$ alkylene group, substituted $C_1$–$C_8$ alkylene group, $C_3$–$C_8$ alkenylene group, substituted $C_3$–$C_8$ alkenylene group, $C_3$–$C_8$ alkynylene group and substituted $C_3$–$C_8$ alkynylene group may be substituted with a $C_2$–$C_5$ alkylene group to form a $C_3$–$C_6$ cycloalkane ring, and arbitrary two carbon atoms in said $C_1$–$C_8$ alkylene group, substituted $C_1$–$C_8$ alkylene group, $C_3$–$C_8$ alkenylene group and substituted $C_3$–$C_8$ alkenylene group may be taken conjointly with an alkylene group or an alkenylene group to form a $C_3$–$C_6$ cycloalkane ring or cycloalkene ring;

$R^1$ represents hydrogen atom, mercapto group, $C_1$–$C_6$ alkylthio group, halo $C_1$–$C_6$ alkylthio group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, or —$A^2$—$R^4$ [wherein $A^2$ represents —C(=O)—, —C(=S)—, or —C(=NR$^5$)— (in which $R^5$ represents hydrogen atom, $C_1$–$C_6$ alkyl group, $C_1$–$C_6$ alkoxy group, mono $C_1$–$C_6$ alkylamino group, di $C_1$–$C_6$ alkylamino group in which $C_1$–$C_6$ alkyl groups may be same or different, $C_1$–$C_6$ alkoxycarbonyl group, phenyl group or substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group), $C_1$–$C_8$ alkylene group, halo $C_1$–$C_8$ alkylene group, $C_3$–$C_6$ alkenylene group, halo $C_3$–$C_6$ alkenylene group, $C_3$–$C_6$ alkynylene group or halo $C_3$–$C_6$ alkynylene group; and (1) in cases where $A^2$ represents —C(=O)—, —C(=S)— or —C(=NR$^5$)— wherein $R^5$ is as defined above, $R^4$ represents hydrogen atom, $C_1$–$C_6$ alkyl group, halo $C_1$–$C_6$ alkyl group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$Z^1$—$R^6$ wherein $Z^1$ represents —O—, —S— or —N($R^7$)— (wherein $R^7$ represents hydrogen atom, $C_1$–$C_6$ alkyl group, $C_1$–$C_6$ alkylcarbonyl group, halo $C_1$–$C_6$ alkylcarbonyl group or $C_1$–$C_6$ alkoxycarbonyl group), and $R^6$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkyl group, substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, cl–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, and (2) in cases where $A^2$ represents $C_1$–$C_8$ alkylene group, halo $C_1$–$C_8$ alkylene group, $C_3$–$C_6$ alkenylene group, halo $C_3$–$C_6$ alkenylene group, $C_3$–$C_6$ alkynylene group or halo $C_3$–$C_6$ alkynylene group, $R^4$ represents hydrogen atom, halogen atom, cyano group, nitro group, $C_3$–$C_6$ cycloalkyl group, halo $C_3$–$C_6$ cycloalkyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, and halo $C_1$–$C_6$ alkylsulfonyl group, or —$Z^2$—$R^8$ wherein $Z^2$ represents —O—, —S—, —SO—, —SO$_2$—, —N($R^9$)— (wherein $R^9$ represents hydrogen atom, $C_1$–$C_6$ alkyl group, $C_1$–$C_6$ alkylcarbonyl group, halo $C_1$–$C_6$ alkylcarbonyl group, $C_1$–$C_6$ alkoxycarbonyl group, phenylcarbonyl group, or substituted phenylcarbonyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group), —C(=O)— or —C(=NOR$^{10}$)— (wherein R$^{10}$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, phenyl $C_1$–$C_4$ alkyl group or substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, and halo $C_1$–$C_6$ alkylsulfonyl group) and R$^8$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, $C_1$–$C_6$ alkylcarbonyl group, halo $C_1$–$C_6$ alkylcarbonyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkyl group, substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group], or alternatively, R$^1$ may be combined with A$^1$ to form a 5- to 8-membered ring which may be intercepted by 1 or 2, same or different oxygen atoms, sulfur atoms or nitrogen atoms;

R$^2$ and R$^3$ which may be same or different, represent hydrogen atom, $C_3$–$C_6$ cycloalkyl group or —A$^2$—R$^4$ wherein A$^2$ and R$^4$ are as defined above; or alternatively, R$^2$ may be combined with A$^1$ or R$^1$ to form a 5- to 7-membered ring which may be intercepted by 1 or 2, same or different oxygen atoms, sulfur atoms or nitrogen atoms;

X which may be same or different, represents halogen atom, cyano group, nitro group, $C_1$–$C_6$ alkyl group, halo $C_1$–$C_6$ alkyl group, $C_2$–$C_6$ alkenyl group, halo $C_2$–$C_6$ alkenyl group, $C_2$–$C_6$ alkynyl group, halo $C_2$–$C_6$ alkynyl group, $C_3$–$C_6$ cycloalkyl group, halo $C_3$–$C_6$ cycloalkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, or $C_1$–$C_6$ alkoxycarbonyl group and l represents an integer of 0 to 4; and alternatively, X may be taken conjointly with the adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and Y may be same or different and represents halogen atom, cyano group, nitro group, halo $C_3$–$C_6$ cycloalkyl group, tri $C_1$–$C_6$ alkylsilyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —A$^3$—R$^{11}$ [wherein A$^3$ represents —O—, —S—, —SO—, —SO$_2$—, —C(=O)—, —C(=NOR$^{12}$)— (in which R$^{12}$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, $C_3$–$C_6$ cycloalkyl group, phenyl $C_1$–$C_4$ alkyl group or substituted phenyl $C_1$–$C_4$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, and halo $C_1$–$C_6$ alkylsulfonyl group), $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group; and (1) in cases where A$^3$ represents —O—, —S—, —SO— or —SO$_2$—, R$^{11}$ represents phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$A^4$—$R^{13}$ (wherein $A^4$ represents $C_1$–$C_6$ alkylene group, halo $C_1$–$C_6$ alkylene group, $C_3$–$C_6$ alkenylene group, halo $C_3$–$C_6$ alkenylene group, $C_3$–$C_6$ alkynylene group or halo $C_3$–$C_6$ alkynylene group, and $R^{13}$ represents hydrogen atom, halogen atom, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, and halo $C_1$–$C_6$ alkylsulfonyl group, or —$A^5$—$R^{14}$ (wherein $A^5$ represents —O—, —S—, —SO—, —$SO_2$— or —C(=O)—, and $R^{14}$ represents $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group)), and (2) in cases where $A^3$ represents —C(=O)— or —C(=NOR$^{12}$)— wherein $R^{12}$ is as defined above, $R^{11}$ represents hydrogen atom, $C_1$–$C_6$ alkyl group, halo $C_1$–$C_6$ alkyl group, $C_2$–$C_6$ alkenyl group, halo $C_2$–$C_6$ alkenyl group, $C_3$–$C_6$ cycloalkyl group, halo $C_3$–$C_6$ cycloalkyl group, $C_1$–$C_6$ alkoxy group, $C_1$–$C_6$ alkylthio group, mono $C_1$–$C_6$ alkylamino group, di $C_1$–$C_6$ alkylamino group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenylamino group, substituted phenylamino group having on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, and (3) in cases where $A^3$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group, $R^{11}$ represents hydrogen atom, hydroxy group, halogen atom, $C_3$–$C_6$ cycloalkyl group, halo $C_3$–$C_6$ cycloalkyl group, $C_1$–$C_6$ alkoxycarbonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$A^6$—$R^{15}$ (wherein $A^6$ represents —O—, —S—, —SO— or —$SO_2$—, and $R^{15}$ represents $C_3$–$C_6$ cycloalkyl group, halo $C_3$–$C_6$ cycloalkyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$A^7$—$R^{16}$ (wherein $A^7$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_1$–$C_6$ alkynylene group, and $R^{16}$ represents hydrogen atom, halogen atom, $C_3$–$C_6$ cycloalkyl group, halo $C_3$–$C_6$ cycloalkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenoxy group, substituted phenoxy group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group))] and m represents an integer of 1 to 5; and Y may be taken conjointly with an adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and n represents an integer of 0 to 2.

7. An agrohorticultural insecticide according to claim 6, wherein $A^1$ represents $C_1$–$C_8$ alkylene group, substituted $C_1$–$C_8$ alkylene group having at least one, same or different substituents selected from the group consisting of halogen atom, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group and $C_1$–$C_6$ alkylthio $C_1$–$C_6$ alkyl group and further, an arbitrary saturated carbon atom in said $C_1$–$C_8$ alkylene group and substituted $C_1$–$C_8$ alkylene group may be substituted with a $C_2$–$C_5$ alkylene group to form a $C_3$–$C_6$ cycloalkane ring, and arbitrary two carbon atoms in said $C_1$–$C_8$ alkylene group and substituted $C_1$–$C_8$ alkylene group may be taken conjointly with an alkylene group or an alkenylene group to form a $C_3$–$C_6$ cycloalkane ring;

$R^1$ represents hydrogen atom, mercapto group, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, halo $C_3$–$C_6$ cycloalkyl group, $C_1$–$C_6$ alkylthio group, halo $C_1$–$C_6$ alkylthio group, $C_1$–$C_6$ alkoxy $C_1$–$C_6$ alkyl group, $C_1$–$C_6$ alkylthio $C_1$–$C_6$ alkyl group, mono $C_1$–$C_6$ alkylamino $C_1$–$C_6$ alkyl group, di $C_1$–$C_6$ alkylamino $C_1$–$C_6$ alkyl group in which $C_1$–$C_6$ alkyl groups may be same or different, $C_1$–$C_6$ alkylcarbonyl group, halo $C_1$–$C_6$ alkylcarbonyl group, $C_1$–$C_6$ alkylthiocarbonyl group, $C_1$–$C_6$ alkoxycarbonyl group, mono $C_1$–$C_6$ alkylaminocarbonyl group, di $C_1$–$C_6$ alkylaminocarbonyl group in which $C_1$–$C_6$ alkyl groups may be same or different, mono $C_1$–$C_6$ alkylamino thiocarbonyl group, di $C_1$–$C_6$ alkylamino thiocarbonyl group in which $C_1$–$C_6$ alkyl groups may be same or different, $C_1$–$C_6$ alkylcarbonyl $C_1$–$C_6$ alkyl group, $C_1$–$C_6$ alkoxyimino $C_1$–$C_6$ alkyl group, $C_1$–$C_6$ alkoxycarbonyl $C_1$–$C_6$ alkyl group, mono $C_1$–$C_6$ alkylaminocarbonyl $C_1$–$C_6$ alkyl group, di $C_1$–$C_6$ alkylaminocarbonyl $C_1$–$C_6$ alkyl group in which $C_1$–$C_6$ alkyl groups may be same or different, phenyl group, substituted phenyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different and $C_1$–$C_6$ alkoxycarbonyl group, phenyl $C_1$–$C_6$ alkyl group, substituted phenyl $C_1$–$C_6$ alkyl group having, on the ring thereof, at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, and $C_1$–$C_6$ alkoxycarbonyl group, phenylcarbonyl group, substituted phenylcarbonyl group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different and $C_1$–$C_6$ alkoxycarbonyl group, phenylthio group, substituted phenylthio group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different and $C_1$–$C_6$ alkoxycarbonyl group, heterocyclic group, or substituted heterocyclic group having at least one, same or different substituents selected from the group consisting of halogen atom, cyano group, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different and $C_1$–$C_6$ alkoxycarbonyl group, or alternatively, $R^1$ may be combined with $A^1$ to form a 5- to 8-membered ring which may be intercepted by 1 or 2, same or different oxygen atoms, sulfur atoms or nitrogen atoms;

$R^2$ and $R^3$ which may be same or different, represent hydrogen atom, $C_1$–$C_6$ alkyl group; or alternatively, $R^2$ may be combined with $A^1$ or $R^1$ to form a 5- to 7-membered ring which may be intercepted by 1 or 2, same or different oxygen atoms, sulfur atoms or nitrogen atoms;

X which may be same or different, represents halogen atom, nitro group, $C_1$–$C_6$ alkyl group, halo $C_1$–$C_6$ alkyl group, $C_2$–$C_6$ alkenyl group, halo $C_2$–$C_6$ alkenyl group, $C_2$–$C_6$ alkynyl group, halo $C_2$–$C_6$ alkynyl group, $C_3$–$C_6$ cycloalkyl group, halo $C_3$–$C_6$ cycloalkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group or halo $C_1$–$C_6$ alkylsulfonyl group and l represents an integer of 0 to 4; and alternatively, X may be taken conjointly with the adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and Y may be same or different and represents halogen atom, $C_1$–$C_6$ alkyl group, halo $C_1$–$C_6$ alkyl group, hydroxy halo $C_1$–$C_6$ alkyl group, $C_1$–$C_6$ alkoxy halo $C_1$–$C_6$ alkyl group, $C_1$–$C_6$ alkylthio halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_1$–$C_6$ alkoxy group, halo $C_1$–$C_6$ alkoxy group, $C_1$–$C_6$ alkoxy halo $C_1$–$C_6$ alkoxy group, $C_1$–$C_6$ alkylthio halo $C_1$–$C_6$ alkoxy group, halo $C_1$–$C_6$ alkoxy halo $C_1$–$C_6$ alkoxy group, halo $C_3$–$C_6$ alkenyloxy group, $C_1$–$C_6$ alkylthio group, halo $C_1$–$C_6$ alkylthio group, halo $C_1$–$C_6$ alkoxy halo $C_1$–$C_6$ alkylthio group, halo $C_1$–$C_6$ alkenylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono $C_1$–$C_6$ alkylamino group, di $C_1$–$C_6$ alkylamino group in which $C_1$–$C_6$ alkyl groups may be same or different, $C_1$–$C_6$ alkoxycarbonyl group, $C_3$–$C_6$ cycloalkyl group, halo $C_3$–$C_6$ cycloalkyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group, and halo $C_1$–$C_6$ alkylsulfonyl group, phenoxy group, substituted phenoxy group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group, and halo $C_1$–$C_6$ alkylsulfonyl group, phenylthio group, substituted phenylthio group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group, pyridyloxy group, substituted pyridyloxy group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group, pyridylthio group, substituted pyridylthio group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group; and m represents an integer of 1 to 5; and Y may be taken conjointly with an adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and n represents an integer of 0 to 2.

8. An agrohorticultural insecticide according to claim 7, wherein $A^1$ represents $C_1$–$C_8$ alkylene group;

$R^1$ represents hydrogen atom, $C_1$–$C_6$ alkyl group, halo $C_1$–$C_6$ alkyl group, $C_3$–$C_6$ alkenyl group, $C_3$–$C_6$ alkynyl group, $C_3$–$C_6$ cycloalkyl group, $C_1$–$C_6$ alkylthio group, $C_1$–$C_6$ alkoxy $C_1$–$C_6$ alkyl group, $C_1$–$C_6$ alkylthio $C_1$–$C_6$ alkyl group, $C_1$–$C_6$ alkylcarbonyl group, mono $C_1$–$C_6$ alkylaminocarbonyl group, di $C_1$–$C_6$ alkylaminocarbonyl group in which $C_1$–$C_6$ alkyl groups may be same or different, mono $C_1$–$C_6$ alkylaminothiocarbonyl group, di $C_1$–$C_6$ alkylaminothiocarbonyl group in which $C_1$–$C_6$ alkyl groups may be same or different, $C_1$–$C_6$ alkylcarbonyl $C_1$–$C_6$ alkyl group, $C_1$–$C_6$ alkoxyimino $C_1$–$C_6$ alkyl group, $C_1$–$C_6$ alkoxycarbonyl $C_1$–$C_6$ alkyl group, mono $C_1$–$C_6$ alkylaminocarbonyl $C_1$–$C_6$ alkyl group or di $C_1$–$C_6$ alkylaminocarbonyl $C_1$–$C_6$ alkyl group in which $C_1$–$C_6$ alkyl groups may be same or different;

$R^2$ and $R^3$ which may be same or different, represent hydrogen atom or $C_1$–$C_6$ alkyl group;

X which may be same or different, represents halogen atom, nitro group, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group or halo $C_1$–$C_6$ alkylsulfonyl group; and l represents an integer of 0 to 4; and alternatively, X may be taken conjointly with the adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group;

Y may be same or different and represents halogen atom, $C_1$–$C_6$ alkyl group, halo $C_1$–$C_6$ alkyl group, $C_1$–$C_6$ alkoxy halo $C_1$–$C_6$ alkyl group, $C_1$–$C_6$ alkoxy group, halo $C_1$–$C_6$ alkoxy group, halo $C_1$–$C_6$ alkoxy halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group, substituted phenoxy group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group, or substituted pyridyloxy group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group; and m represents an integer of 1 to 5; and Y may be taken conjointly with an adjacent carbon atom on the phenyl ring to form a fused ring, and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, halo $C_1$–$C_6$ alkylsulfinyl group and halo $C_1$–$C_6$ alkylsulfonyl group; and n represents an integer of 0 to 2.

9. A method for using an agrohorticultural insecticide, characterized by treating an objective crop or applying to soil in an effective quantity of the agrohorticultural insecticide according to any one of claims 5 to 8 for the purpose of protecting a useful crop.

* * * * *